(12) United States Patent
Davis et al.

(10) Patent No.: US 11,559,581 B2
(45) Date of Patent: Jan. 24, 2023

(54) ANTIBODY CONJUGATES AND METHODS OF MAKING THE ANTIBODY CONJUGATES

(71) Applicant: Isis Innovation Limited, Oxford (GB)

(72) Inventors: Benjamin G. Davis, Oxford (GB); Keisuke Yamamoto, Oxford (GB); Thomas Taylor, Oxford (GB); Thomas B. Parsons, Oxford (GB); Jonathan Goodfellow, Oxford (GB)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 1156 days.

(21) Appl. No.: 14/991,281

(22) Filed: Jan. 8, 2016

(65) Prior Publication Data

US 2016/0361436 A1 Dec. 15, 2016

Related U.S. Application Data

(60) Provisional application No. 62/101,634, filed on Jan. 9, 2015.

(51) Int. Cl.
*A61K 47/48* (2006.01)
*A61K 47/68* (2017.01)
*C07K 16/32* (2006.01)

(52) U.S. Cl.
CPC ...... *A61K 47/6811* (2017.08); *A61K 47/6855* (2017.08); *A61K 47/6883* (2017.08); *C07K 16/32* (2013.01)

(58) Field of Classification Search
None
See application file for complete search history.

(56) References Cited

FOREIGN PATENT DOCUMENTS

WO WO-2014065661 A * 5/2014 ....... A61K 47/48715

OTHER PUBLICATIONS

Huang etal ("Huang", J. Am. Chem. Soc., 2012, 134, 12308-12318).*
Database Caplus Chemical Abstracts Service, Columbus, Ohio, US; Database Accession No. 2016:76138, Abstractor Parsons et al., Angewandte Chemie, International Edition (2016), 55(7), 2361-2367 (Year: 2016).*
Ohtsubo, K.; Marth, J. D. Cell 2006, 126, 855.
Apweiler, R.; Hermjakob, H.; Sharon, N. Biochim. Biophys. Acta 1999, 1473, 4.
Jung, E.; Veuthey, A.-L.; Gasteiger, E.; Bairoch, A. Proteomics 2001, 1, 262.
Sethuraman, N.; Stadheim, T. A. Curr. Opin. Biotechnol. 2006, 17, 341.
Rudd, P. M.; Joao, H. C.; Coghill, E.; Fiten, P.; Saunders, M. R.; Opdenakker, G.; Dwek, R. A. Biochemistry 1994, 33, 17.
Suzuki, T.; Kitajima, K.; Inoue, S.; Inoue, Y. Glycoconjugate J. 1995, 12, 183.
Jefferis, R. Nat. Rev. Drug Discov. 2009, 8, 226.
Anthony, R. M.; Nimmerjahn, F.; Ashline, D. J.; Reinhold, V. N.; Paulson, J. C.; Ravetch, J. V. Science 2008, 320, 373.
Gerngross, T. U. Nat. Biotechnol. 2004, 22, 1409.

(Continued)

*Primary Examiner* — Karl J Puttlitz
(74) *Attorney, Agent, or Firm* — Thomas|Horstemeyer, LLP

(57) ABSTRACT

Described herein are antibody conjugates and methods of making antibody conjugates.

11 Claims, 61 Drawing Sheets

(56) References Cited

OTHER PUBLICATIONS

Betenbaugh, M. J.; Tomiya, N.; Narang, S.; Hsu, J. T. A.; Lee, Y. C. Curr. Opin. Struct. Biol. 2004, 14, 601.
Kowarik, M.; Numao, S.; Feldman, M. F.; Schulz, B. L.; Callewaert, N.; Kiermaier, E.; Catrein, I.; Aebi, M. Science 2006, 314, 1148.
Bennett, C. S.; Wong, C.-H. Chem. Soc. Rev. 2007, 36, 1227.
Gamblin, D. P.; Scanlan, E. M.; Davis, B. G. Chem. Rev. 2009, 109, 131.
Witte, K.; Sears, P.; Martin, R.; Wong, C.-H. J. Am. Chem. Soc. 1997, 119, 2114.
Wang, L.-X. Carbohydr. Res. 2008, 343, 1509.
Rich, J. R.; Withers, S. G. Nat. Chem. Biol. 2009, 5, 206.
Schwarz, F.; Huang, W.; Li, C.; Schulz, B. L.; Lizak, C.; Palumbo, A.; Numao, S.; Neri, D.; Aebi, M.; Wang, L.-X. Nat. Chem. Biol. 2010, 6, 264.
Huang, W.; Yang, Q.; Umekawa, M.; Yamamoto, K.; Wang, L.-X. ChemBioChem 2010, 11, 1350.
Huang, W.; Li, J.; Wang, L.-X. ChemBioChem 2011, 12, 932.
Reeves, P. J.; Callewaert, N.; Contreras, R.; Khorana, H. G. Proc. Natl Acad. Sci. U.S.A. 2002, 99, 13419.
Chang, V. T.; Crispin, M.; Aricescu, A. R.; Harvey, D. J.; Nettleship, J. E.; Fennelly, J. A.; Yu, C.; Boles, K. S.; Evans, E. J.; Stuart, D. I.; Dwek, R. A.; Jones, E. Y.; Owens, R. J.; Davis, S. J. Structure 2007, 15, 267.
Harvey, D. J.; Merry, A. H.; Royle, L.; Campbell, M. P.; Dwek, R. A.; Rudd, P. M. Proteomics 2009, 3796.
Domon, B.; Costello, C. E. Glycoconjugate J. 1988, 5, 397.
Harvey, D. J. J. Am. Soc. Mass Spectrom. 2005, 16, 647.
Harvey, D. J. Rapid Commun. Mass Spectrom. 2005, 19, 484.
Collin, M.; Olsen, A. EMBO J. 2001, 20, 3046.
Allhorn, M.; Briceno, J. G.; Baudino, L.; Lood, C.; Olsson, M. L.; Izui, S.; Collin, M. Blood 2010, 115, 5080.
Robbins, P. W.; Trimble, R. B.; Wirth, D. F.; Hering, C.; Maley, F.; Maley, G. F.; Das, R.; Gibson, B. W.; Royal, N.; Biemann, K. J. Biol Chem. 1984, 259, 7577.
Jefferis, R. Biotechnol. Prog. 2005, 21, 11.
Goetze, A. M.; Zhang, Z.; Liu, L.; Jacobsen, F. W.; Flynn, G. C. Mol. Immunol. 2011, 49, 338.
Yamamoto, K. J.; Kadowaki, S.; Watanabe, J.; Kumagai, H. Biochem. Biophys. Res. Commun. 1994, 203, 244.
Fujita, K.; Yamamoto, K. Biochim. Biophys. Acta 2006, 1760, 1631.
Takegawa, K.; Tabuchi, M.; Yamaguchi, S.; Kondo, A.; Kato, I.; Iwahara, S. J. Biol. Chem. 1995, 270, 3094.
Li, B.; Song, H.; Hauser, S.; Wang, L.-X. Org. Lett. 2006, 8, 3081.
Heidecke, C. D.; Ling, Z.; Bruce, N. C.; Moir, J. W. B.; Parsons, T. B.; Fairbanks, A. J. ChemBioChem 2008, 9, 2045.
Rising, T. W.; Heidecke, C. D.; Moir, J. W.; Ling, Z; Fairbanks, A. J. Chem.—Eur. J. 2008, 14, 6444.
Ochiai, H.; Huang, W.; Wang, L.-X. J. Am. Chem. Soc. 2008, 130, 13790.
Huang, W.; Li, C.; Li, B.; Umekawa, M.; Yamamoto, K.; Zhang, X.; Wang, L.-X. J. Am. Chem. Soc. 2009, 131, 2214.
Fernandez-Gonzalez, M.; Boutureira, O.; Bernardes, G. J. L.; Chalker, J. M.; Young, M. A.; Errey, J. C.; Davis, B. G. Chem. Sci. 2010, 1, 709.
Wang, L. X.; Wei, Y. D.; Li, C. S.; Huang, W.; Li, B.; Strome, S. Biochemistry 2008, 47, 10294.
Zou, G.; Ochiai, H.; Huang, W.; Yang, Q.; Li, C.; Wang, L.-X. J. Am. Chem. Soc. 2011, 133,18975.
Mimura, Y.; Church, S.; Ghirlando, R.; Ashton, P. R.; Dong, S.; Goodall, M.; Lund, J.; Jefferis, R. Mol. Immunol. 2000, 37, 697.
Allhorn, M.; Collin, M. Ann. N.Y. Acad. Sci. 2009, 1173, 664.
Adams, G. P.; Weiner, L. M. Nat. Biotechnol. 2005, 23, 1147-1157.
Aggarwal, S. Nat. Biotechnol. 2011, 29, 1083-1089.
Nimmerjahn, F.; Ravetch, J. V. Nat. Rev. Immunol. 2008, 8, 34-47.
Takahashi, N.; Nakagawa, H.; Fujikawa, K.; Kawamura, Y.; Tomiya, N. Anal. Biochem. 1995, 226,139-146.
Wormald, M. R.; Rudd, P. M.; Harvey, D. J.; Chang, S. C.; Scragg, I. G.; Dwek, R. A. Biochemistry 1997, 36, 1370-1380.
Sondermann, P.; Huber, R.; Oosthuizen, V.; Jacob, U. Nature 2000, 406, 267-273.
Krapp, S.; Mimura, Y.; Jefferis, R.; Huber, R.; Sondermann, P. J. Mol. Biol. 2003, 325, 979-989.
Crispin, M.; Bowden, T. A.; Coles, C. H.; Harios, K.; Aricescu, A. R.; Harvey, D. J.; Stuart, D. I.; Jones, E. Y. J. Mol. Biol. 2009, 387, 1061-1066.
Ferrara, C.; Grau, S.; Jager, C.; Sondermann, P.; Brunker, P.; Waldhauer, I.; Hennig, M.; Ruf, A.; Rufer, A. C.; Stihle, M.; Umana, P.; Benz, J. Proc. Natl. Acad. Sci. U.S.A. 2011, 108, 12669-12674.
Yamaguchi, Y.; Nishimura, M.; Nagano, M.; Yagi, H.; Sasakawa, H.; Uchida, K.; Shitara, K.; Kato, K. Biochim. Biophys. Acta 2006, 1760, 693-700.
Matsumiya, S.; Yamaguchi, Y.; Saito, J.; Nagano, M.; Sasakawa, H.; Otaki, S.; Satoh, M.; Shitara, K.; Kato, K. J. Mol. Biol. 2007, 368, 767-779.
Barb, A. W.; Prestegard, J. H. Nat. Chem. Biol. 2011, 7, 147-153.
Shields, R. L.; Lai, J.; Keck, R.; O'Connell, L. Y.; Hong, K.; Meng, Y. G.; Weikert, S. H.; Presta, L. G. J. Biol. Chem. 2002, 277, 26733-26740.
Shinkawa, T.; Nakamura, K.; Yamane, N.; Shoji-Hosaka, E.; Kanda, Y.; Sakurada, M.; Uchida, K.; Anazawa, H.; Satoh, M.; Yamasaki, M.; Hanai, N.; Shitara, K. J. Biol. Chem. 2003, 278, 3466-3473.
Niwa, R.; Shoji-Hosaka, E.; Sakurada, M.; Shinkawa, T.; Uchida, K.; Nakamura, K.; Matsushima, K.; Ueda, R.; Hanai, N.; Shitara, K. Cancer Res. 2004, 64, 2127-2133.
Strome, S. E.; Sausville, E. A.; Mann, D. Oncologist 2007, 12, 1084-1095.
Jefferis, R. Methods Mol. Biol. 2009, 483, 223-238.
Kaneko, Y.; Nimmerjahn, F.; Ravetch, J. V. Science 2006, 313, 670-673.
Anthony, R. M.; Wermeling, F.; Karlsson, M. C.; Ravetch, J. V. Proc. Natl. Acad. Sci. U.S.A. 2008, 105, 19571-19578.
Umana, P.; Jean-Mairet, J.; Moudry, R.; Amstutz, H.; Bailey, J. E. Nat. Biotechnol. 1999, 17, 176-180.
Yamane-Ohnuki, N.; Kinoshita, S.; Inoue-Urakubo, M.; Kusunoki, M.; Iida, S.; Nakano, R.; Wakitani, M.; Niwa, R.; Sakurada, M.; Uchida, K.; Shitara, K.; Satoh, M. Biotechnol. Bioeng. 2004, 87, 614-622.
Stanley, P.; Sundaram, S.; Tang, J.; Shi, S. Glycobiology 2005, 15, 43-53.
Cox, K. M.; Sterling, J. D.; Regan, J. T.; Gasdaska, J. R.; Frantz, K. K.; Peele, C. G.; Black, A.; Passmore, D.; Moldovan-Loomis, C.; Srinivasan, M.; Cuison, S.; Cardarelli, P. M.; Dickey, L. F. Nat. Biotechnol. 2006,24, 1591-1597.
Strasser, R.; Castilho, A.; Stadlmann, J.; Kunert, R.; Quendler, H.; Gattinger, P.; Jez, J.; Rademacher, T.; Altmann, F. Mach, L.; Steinkellner, H. J. Biol. Chem. 2009, 284, 20479-20485.
Li, H.; et al. Nat. Biotechnol. 2006, 24, 210-215.
Zhou, Q.; Shankara, S.; Roy, A.; Qiu, H.; Estes, S.; McVie-Wylie, A.; Culm-Merdek, K.; Park, A.; Pan, C.; Edmunds, T. Biotechnol. Bioeng 2008, 99, 652-665.
Schiestl, M.; Stangler, T.; Torella, C.; Cepeljnik, T.; Toll, H.; Grau, R. Nat. Biotechnol. 2011, 29, 310-312.
Wang, L. X.; Lomino, J. V. ACS Chem. Biol. 2012, 7, 110-122.
Wang, L. X. Trends Glycosci. Glycotechnol. 2011, 23, 33-52.
Fan, S. Q.; Huang, W.; Wang, L. X. J. Biol. Chem. 2012, 287, 11272-11281.
Umekawa, M.; Li, C.; Higashiyama, T.; Huang, W.; Ashida, H.; Yamamoto, K.; Wang, L. X. J. Biol. Chem. 2010, 285, 511-521.
Umekawa, M.; Huang, W.; Li, B.; Fujita, K.; Ashida, H.; Wang, L. X.; Yamamoto, K. J. Biol. Chem. 2008, 283, 4469-4479.
Allhorn, M.; Olsen, A.; Collin, M. BMC Microbiol. 2008, 8, 3.
Goodfellow, J. J.; Baruah, K.; Yamamoto, K.; Bonomelli, C.; Krishna, B.; Harvey, D. J.; Crispin, M.; Scanlan, C. N.; Davis, B. G. J. Am. Chem. Soc. 2012, 134, 8030-8033.
Umekawa, M.; Higashiyama, T.; Koga, Y.; Tanaka, T.; Noguchi, M.; Kobayashi, A.; Shoda, S.; Huang, W.; Wang, L. X.; Ashida, H.; Yamamoto, K. Biochim. Biophys. Acta 2010, 1800, 1203-1209.
Waddling, C. A.; Plummer, T. H., Jr.; Tarentino, A. L.; Van Roey, P. Biochemistry 2000, 39, 7878-7885.

(56) References Cited

OTHER PUBLICATIONS

Wan, H. Z.; Kaneshiro, S.; Frenz, J.; Cacia, J. J. Chromatogr., A 2001, 913, 437-446.
Li, B.; Zeng, Y.; Hauser, S.; Song, H.; Wang, L. X. J. Am. Chem. Soc. 2005, 127, 9692-9693.
Sletten, E. M.; Bertozzi, C. R. Acc. Chem. Res. 2011, 44, 666-676.
Best, M. D. Biochemistry 2009,48, 6571-6584.
Cartron, G.; Dacheux, L.; Salles, G.; Solal-Celigny, P.; Bardos, P.; Colombat, P.; Watier, H. Blood 2002, 99, 754-758.
Sazinsky, S. L.; Ott, R. G.; Silver, N. W.; Tidor, B.; Ravetch, J. V.; Wittrup, K. D. Proc. Natl. Acad. Sci. U.S.A. 2008, 105, 20167-20172.
Anthony, R. M.; Kobayashi, T.; Wermeling, F.; Ravetch, J. V. Nature 2011,475, 110-113.
Huhn, C.; Selman, M. H.; Ruhaak, L. R.; Deelder, A. M.; Wuhrer, M. Proteomics 2009, 9, 882-913.
Barb, A. W.; Brady, E. K.; Prestegard, J. H. Biochemistry 2009,48, 9705-9707.
Guhr, T.; Bloem, J.; Derksen, N. I.; Wuhrer, M.; Koenderman, A. H.; Aalberse, R. C.; Rispens, T. PLoS One 2011, 6, e21246.
Raju, T. S.; Scallon, B. J. Biochem. Biophys. Res. Commun. 2006, 341, 797-803.
Guile, G. R.; Rudd, P. M.; Wing, D. R.; Prime, S. B.; Dwek, R. A. Anal. Biochem. 1996, 240, 210-226.
Johnson, P.; Glennie, M. Semin. Oncol. 2003, 30, 3-8.
Koene, H. R.; Kleijer, M.; Algra, J.; Roos, D.; von dem Borne, A. E.; de Haas, M. Blood 1997, 90, 1109-1114.
Hessell, A. J.; Hangartner, L.; Hunter, M.; Havenith, C. E.; Beurskens, F. J.; Bakker, J. M.; Lanigan, C. M.; Landucci, G.; Forthal, D. N.; Parren, P. W.; Marx, P. A.; Burton, D. R. Nature 2007, 449, 101-104.
Collin, M.; Olsen, A. Infect. Immun. 2001, 69, 7187-7189.
Goodfellow, et al., An Endoglycosidase with Alternative Glycan Specificity Allows Broadened Glycoprotein Remodeling, JACS 134,2012, pp. 8030-8033.
Huang, et al., Chemoenzymatic Glycoengineering of Intact IgG Antibodies for Gain of Functions, JACS 134 (2012), pp. 12308-12318.

\* cited by examiner

Scheme (I)

Scheme (II)

Scheme (III)

Scheme (IV)

Scheme (V)

Scheme (VI)

Scheme (VII)

Scheme (VIII)

Scheme (IX)  44%

Scheme (X)  69%

Scheme (XI)  41%

Scheme (XII)  56%

1: Protein marker
2: GlcNAc-mAb
3: Transglycosylation product
4: Glycosylated mAb after WT Endo S
5: Glycosylated mAb after PNGase F
6: GlcANc-mAb 1. Pre-stained protein marker
2. CuAAC reaction
3. CuAAc product after PNGase F
4. mAb after transglycosylation 1: Herceptin
2: CuAAC reaction mAb-azide
3: CuAAc product after PNGase F
4: CuAAC reaction mAb-alkyne
5: Pre-stained marker Around 95% conversion 1: Herceptin
2: CuAAC reaction mAb-azide
3: CuAAc product after PNGase F
4: CuAAC reaction mAb-alkyne
5: Pre-stained marker

| Kw | log mW | | retention vol |
|---|---|---|---|
| 4.8865 | 0.3249 | holotransferrin | 13.05 |
| 5.179 | 0.2398 | IgG | 11.67 |
| 5.322 | 0.225 | B-amylase | 11.6 |
| 4.1761 | 0.5543 | RNAse B | 16.77 |
| 4.823 | 0.3409 | BSA | 13.31 |
| | | blue dextran | 7.78 |

ANTIBODY CONJUGATES AND METHODS OF MAKING THE ANTIBODY CONJUGATES

CROSS-REFERENCE TO RELATED APPLICATION

This application claims the benefit of U.S. Provisional Application Ser. No. 62/101,634 filed on Jan. 9, 2015, having the title "Antibody Conjugates and Methods of Making the Antibody Conjugates", the entirety of which is incorporated herein by reference.

STATEMENT REGARDING GOVERNMENTAL SPONSORED RESEARCH OR DEVELOPMENT

This invention was made with government support from the Biotechnology and Biological Sciences Research Grant Number BB/F01709X/1. The government may have certain rights in the invention.

BACKGROUND

Targeted therapy is a modality of therapy for diseases, including cancer, in which a drug, molecule, or other compound is delivered to a specific location, cell, or cell type. Targeted therapy seeks to improve treatment of diseases, inter alia, by reducing side effects and toxicity due to interactions with non-diseased cells, increasing efficacy by increasing specificity, and reducing the necessary effective dose amounts.

Due to their ability to bind epitopes specifically, there have been attempts at utilizing antibodies or fragments thereof as a targeting moiety for targeted delivery of small molecules. However, these attempts often fail during development because of varying therapeutic efficacy and toxic side effects. Targeted antibody-based therapies that successfully make it to market often have to be recalled from the market for being unsafe or failing to comply with regulatory standards. As such, there is an urgent and unmet need for improved targeted therapies.

BRIEF DESCRIPTION OF THE DRAWINGS

Further aspects of the present disclosure will be readily appreciated upon review of the detailed description of its various embodiments, described below, when taken in conjunction with the accompanying drawings.

FIS. 25 one embodiment of remodeling of a trimmed antibody with an oxazoline oligosaccharide.

Figures 26A, 26B:
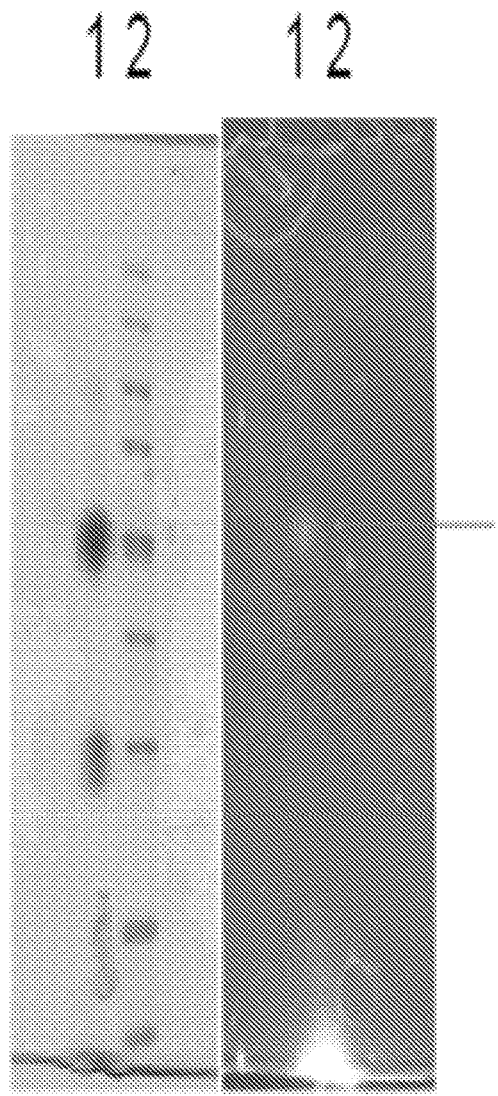

FIGS. 26A-26B demonstrate attachment of a payload molecule to a modified antibody.

Figures 27A, 27B, 27C, 27D:
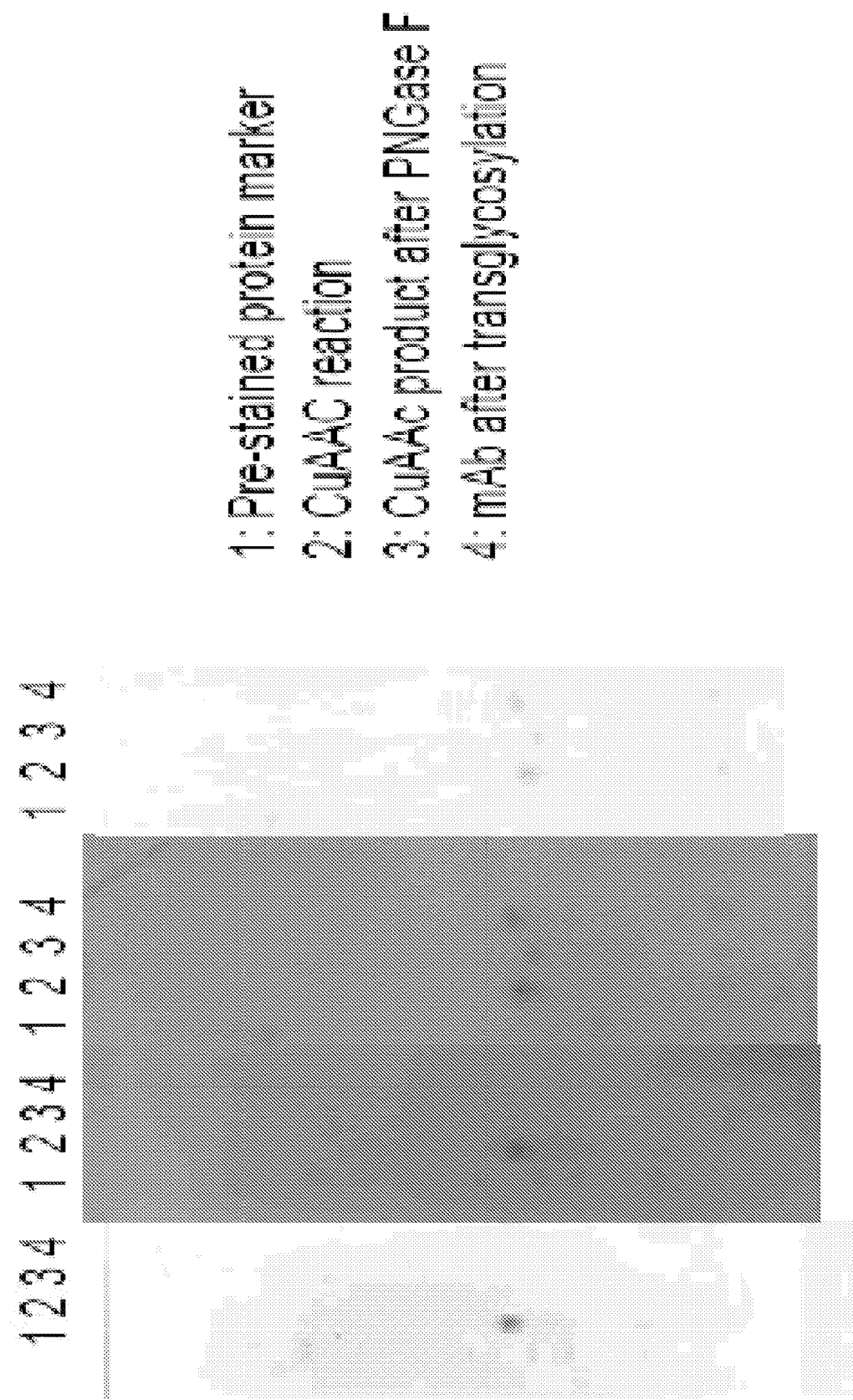

FIGS. 27A-27B demonstrate attachment of a payload molecule to a modified antibody.

Figures 28A, 28B:
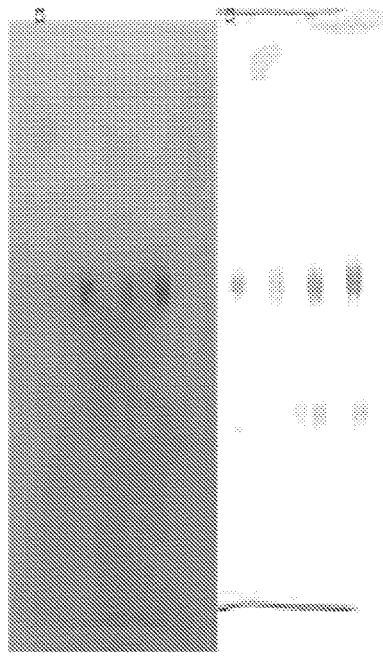
Figure 29:
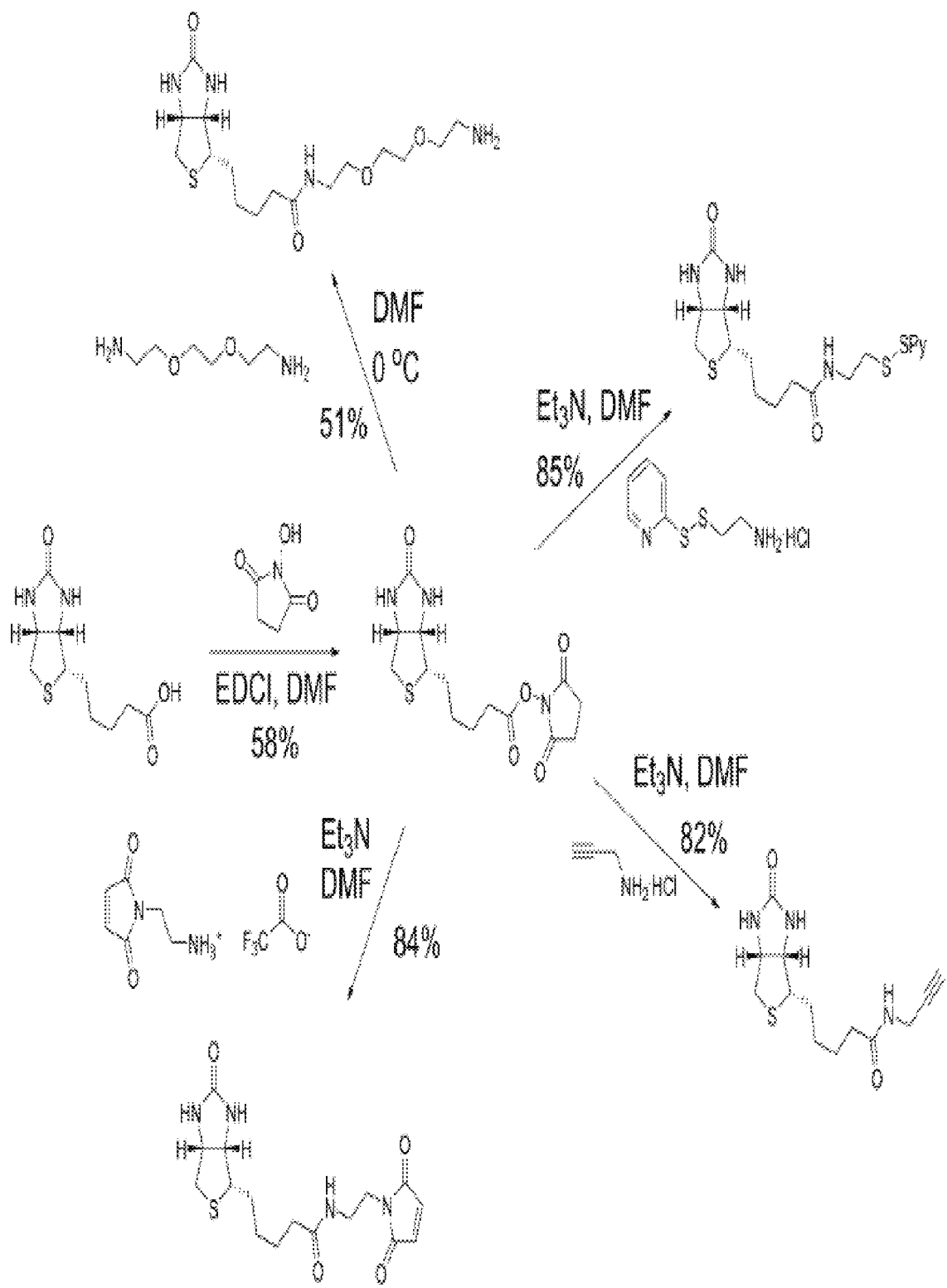
Figure 30A:
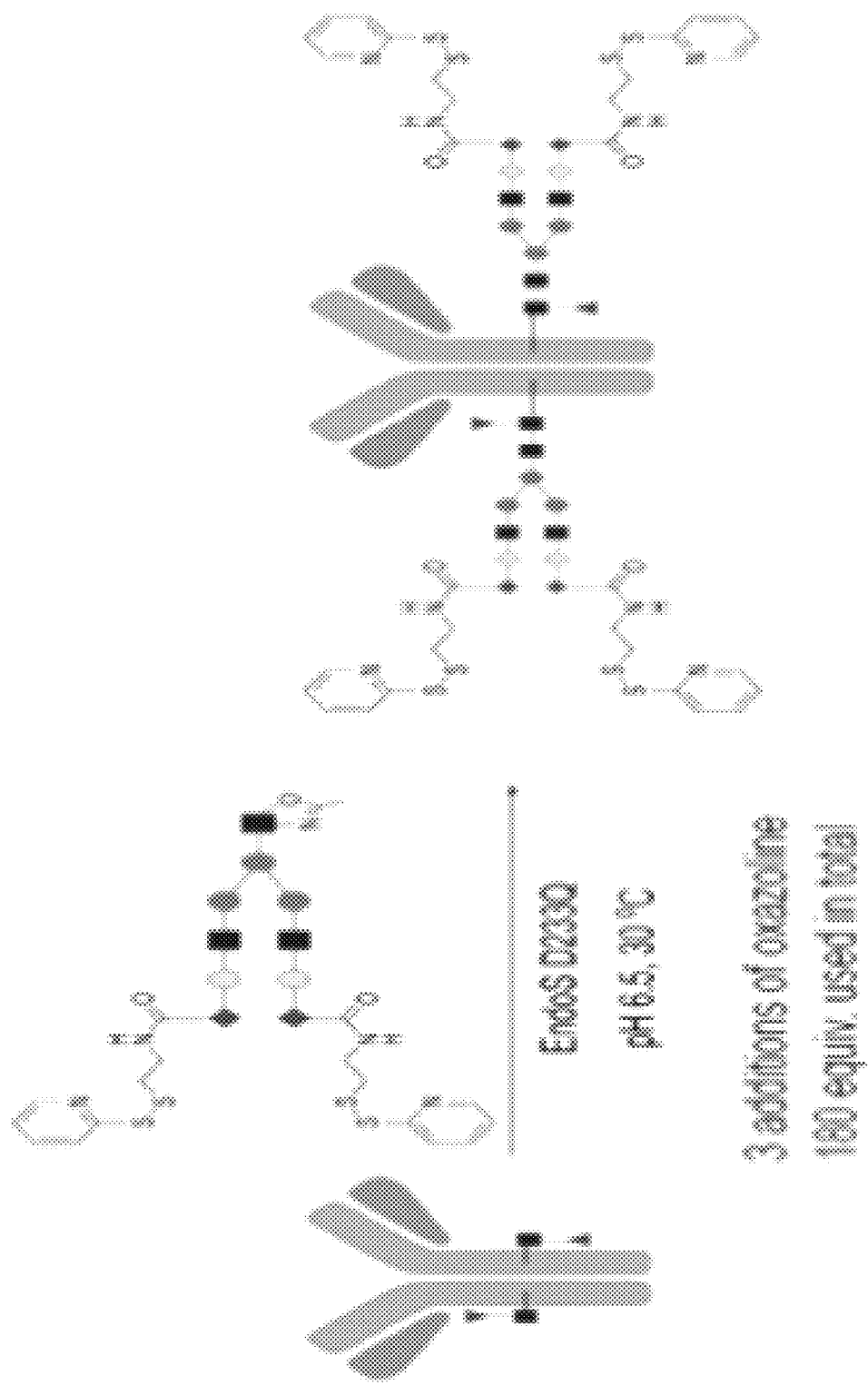
Figures 30B, 30C:
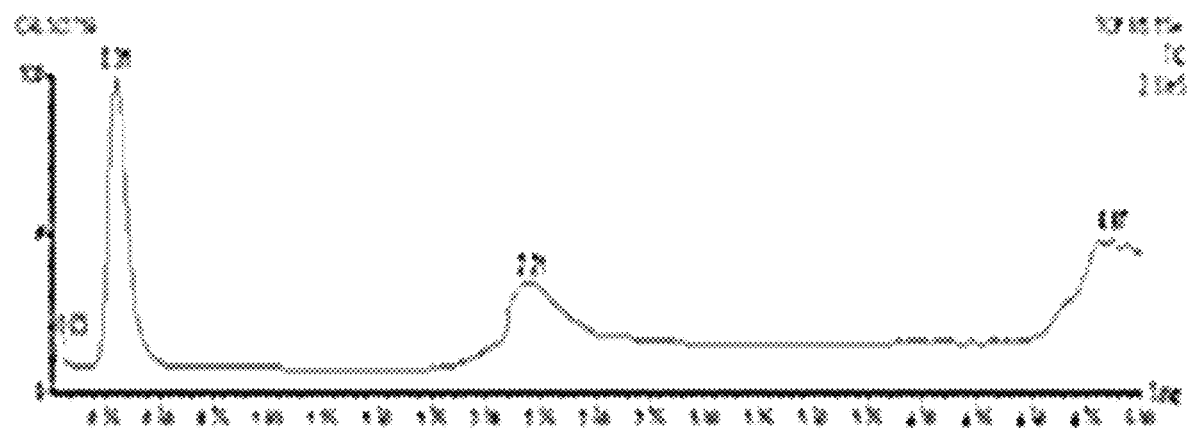
Figure 30D:
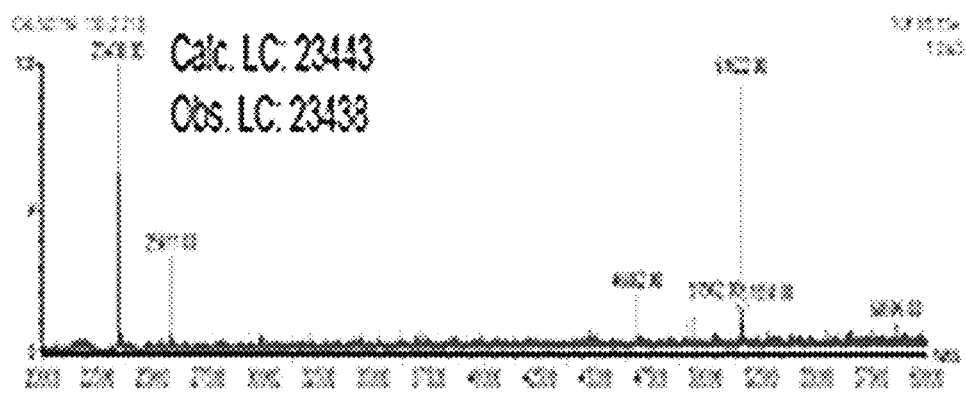
Figure 30E:
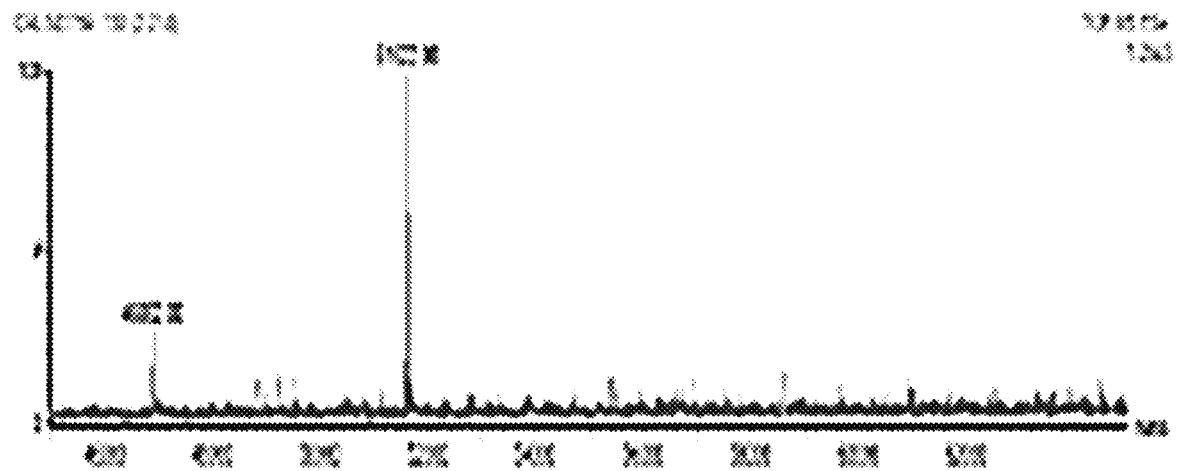
Figure 31A:
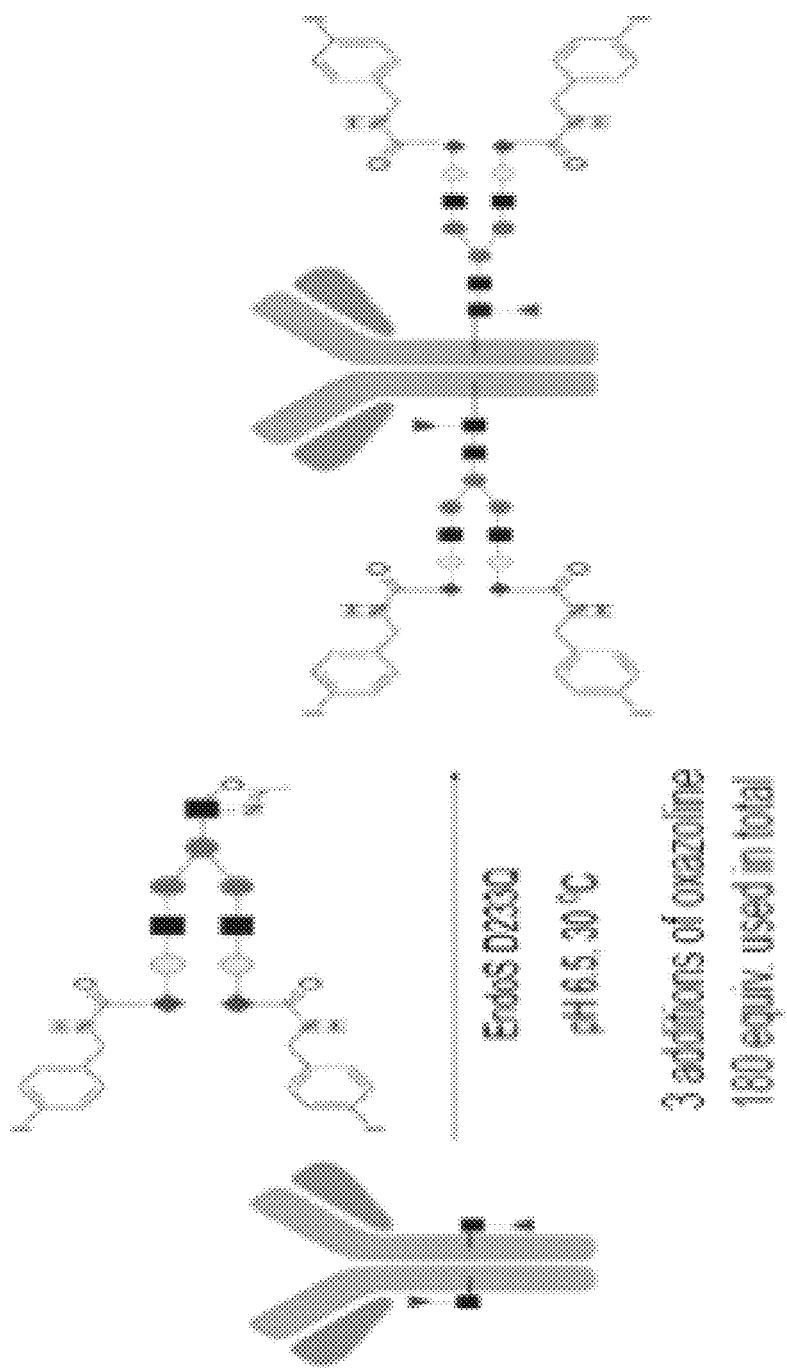
Figure 31B:
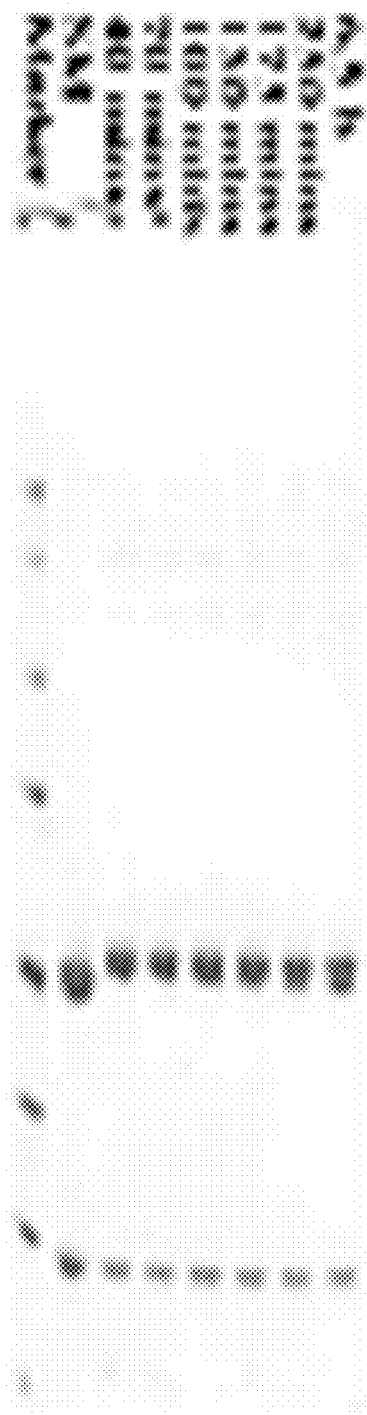
Figure 31C:
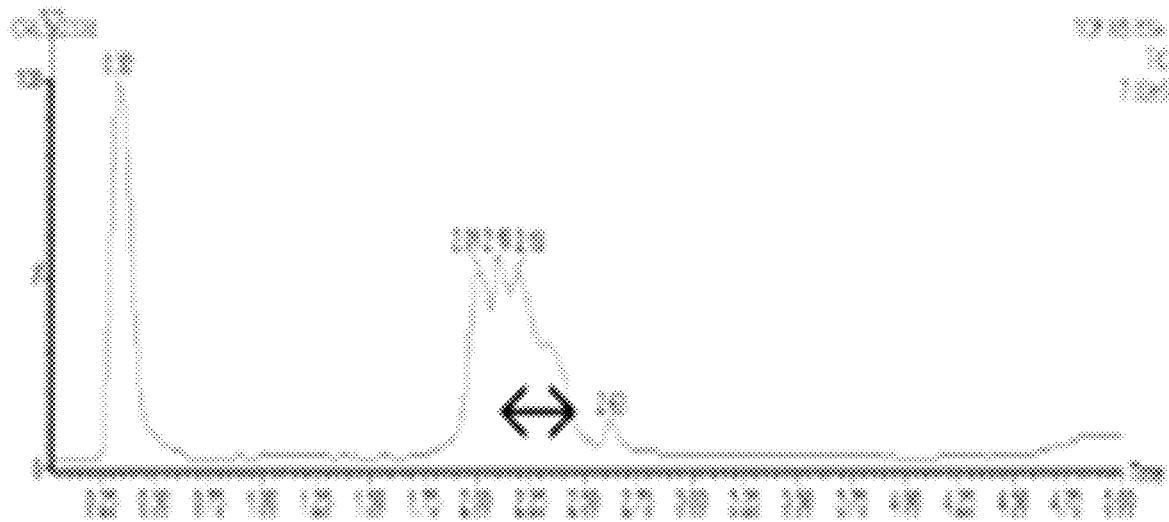
Figure 31D:
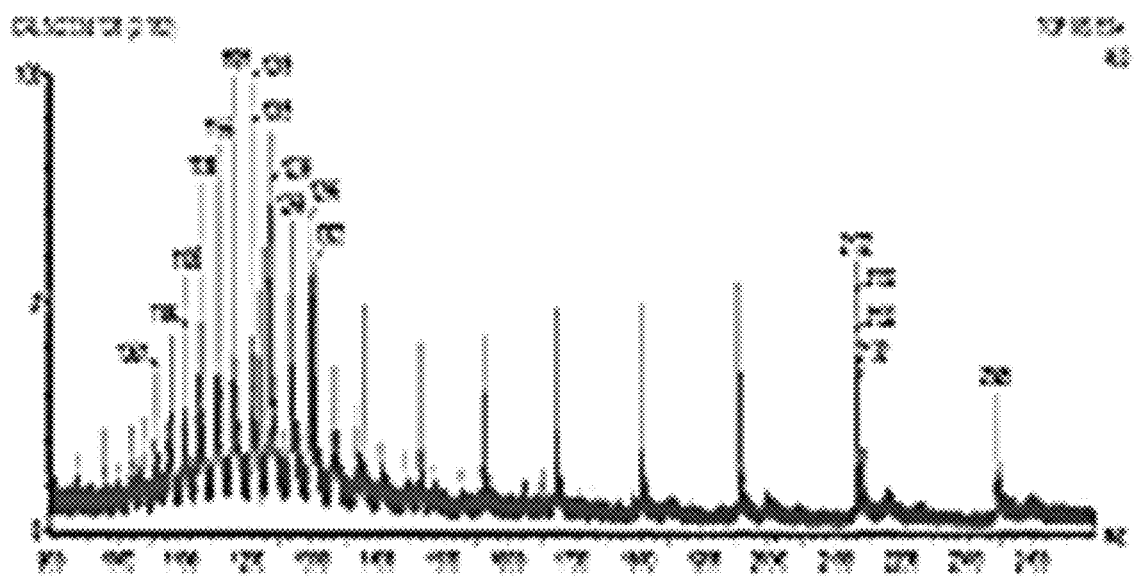
Figure 31E:
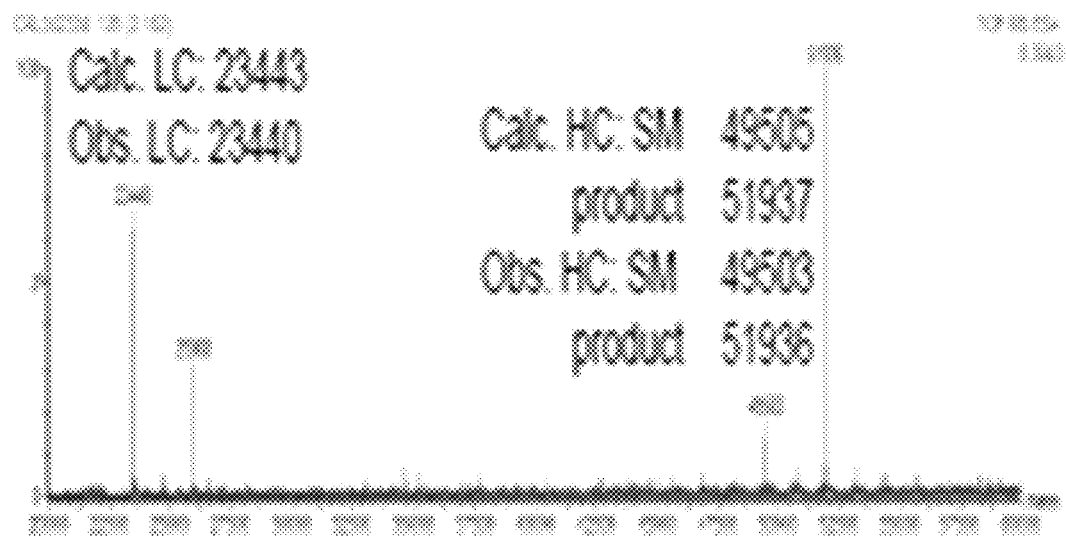
Figure 31F:
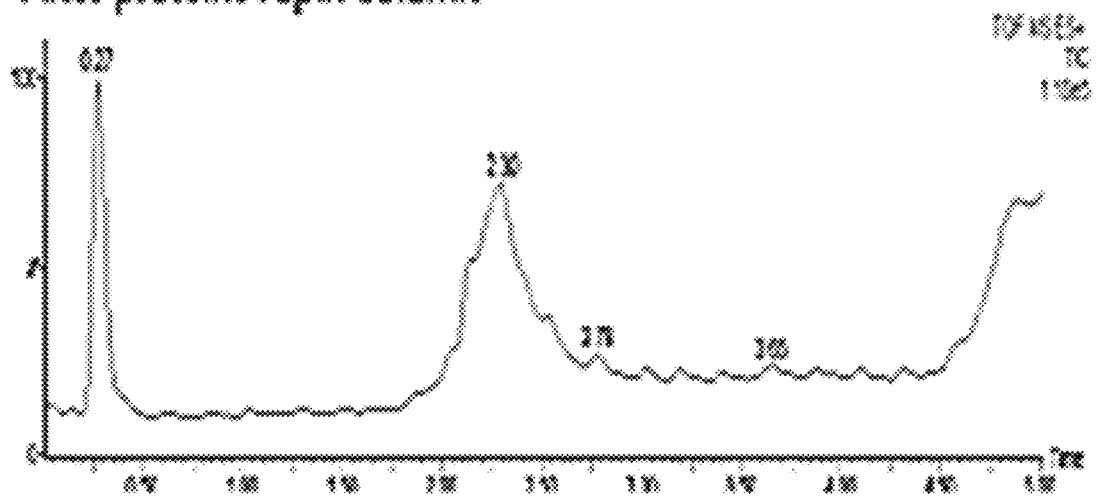
Figure 31G:
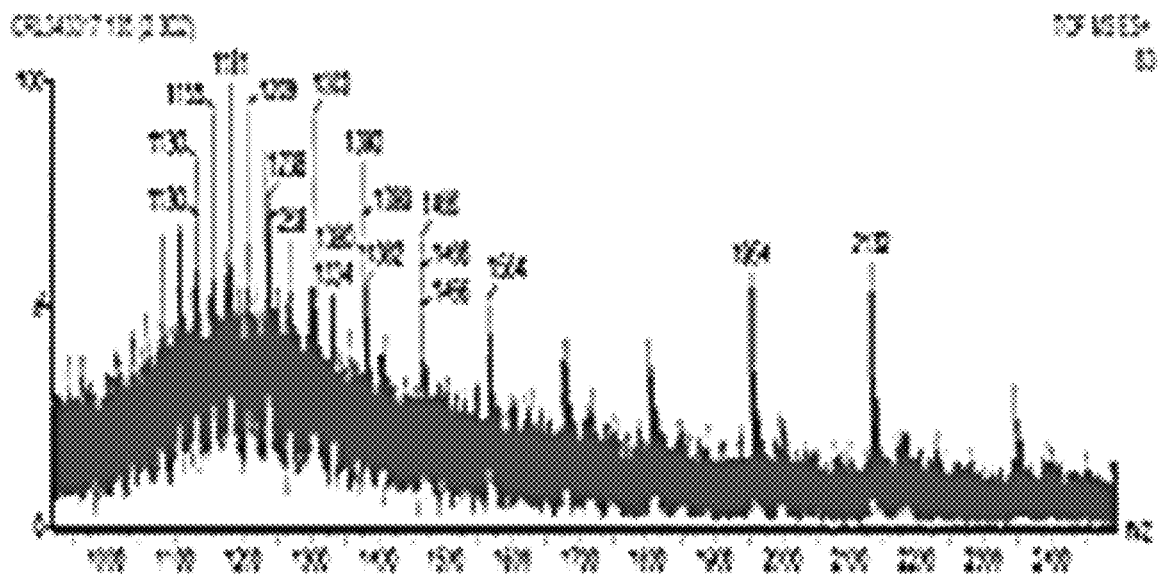
Figure 31H:
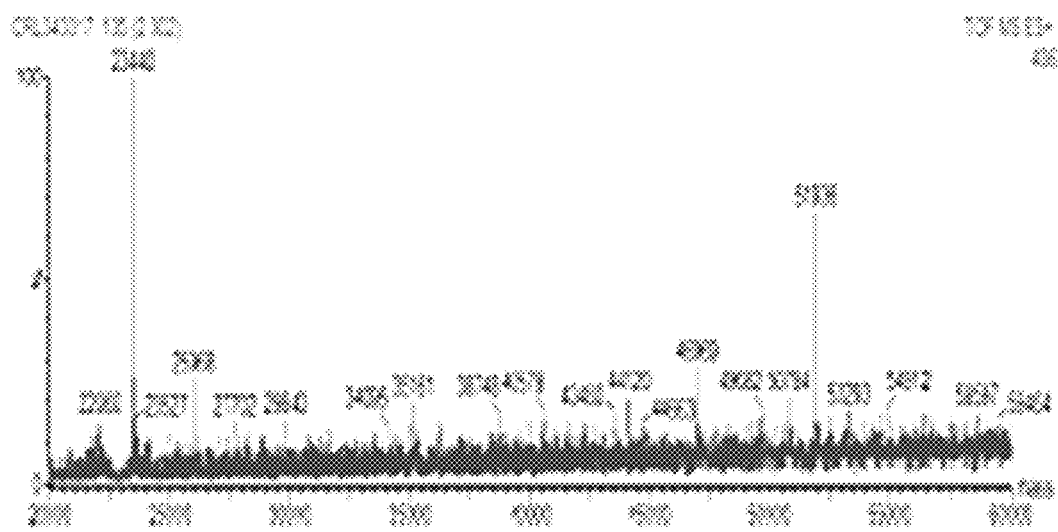
Figure 32A:
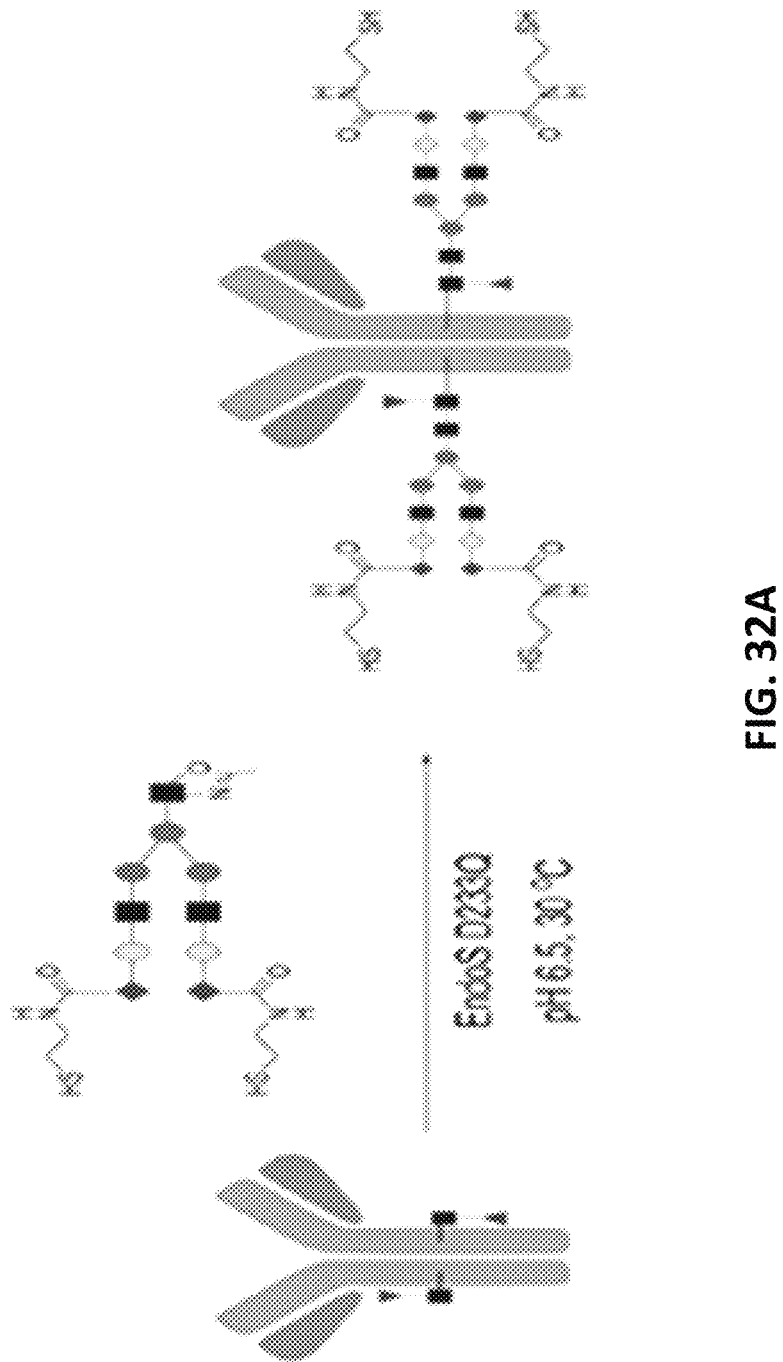
Figure 32B:
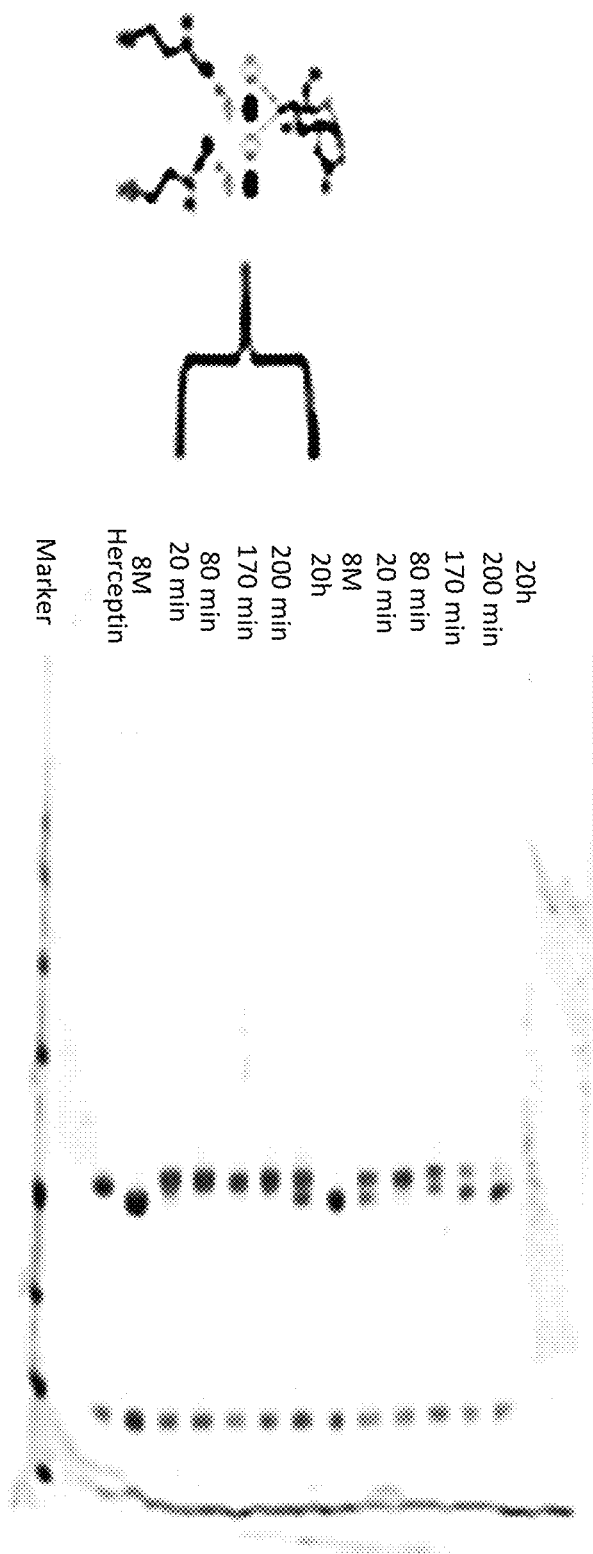
Figure 32C:
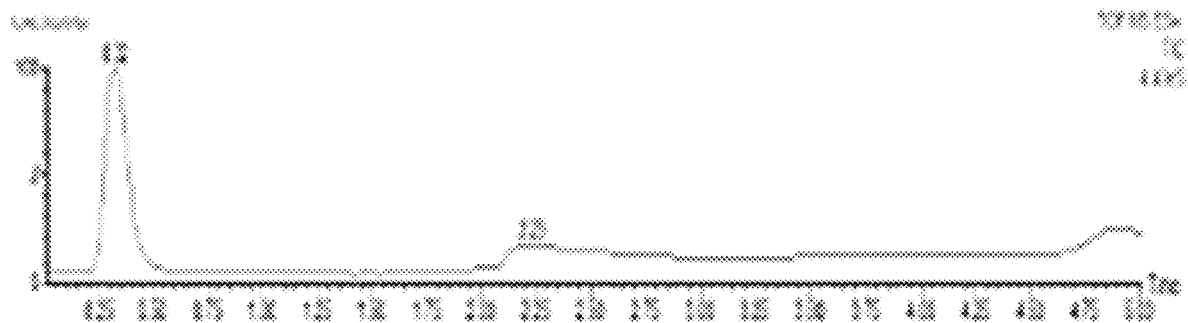
Figure 32D:
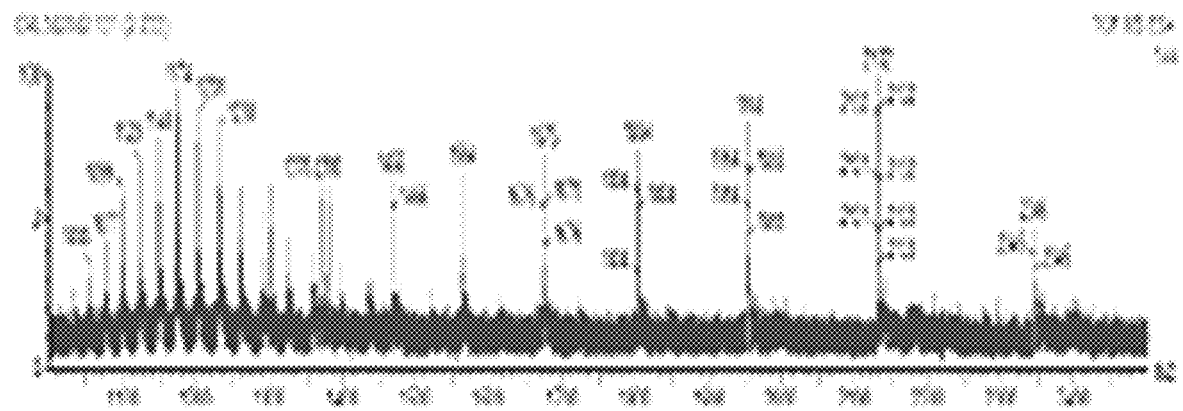
Figure 32E:
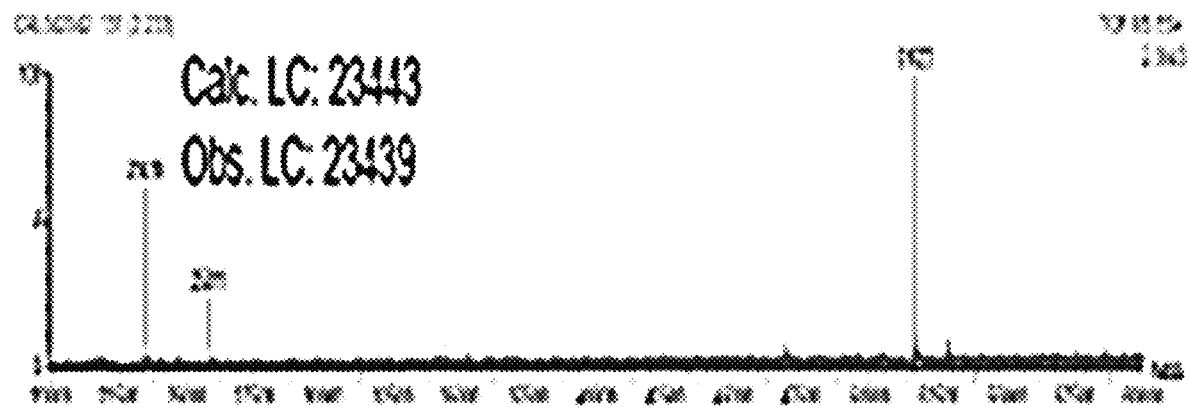
Figure 32F:
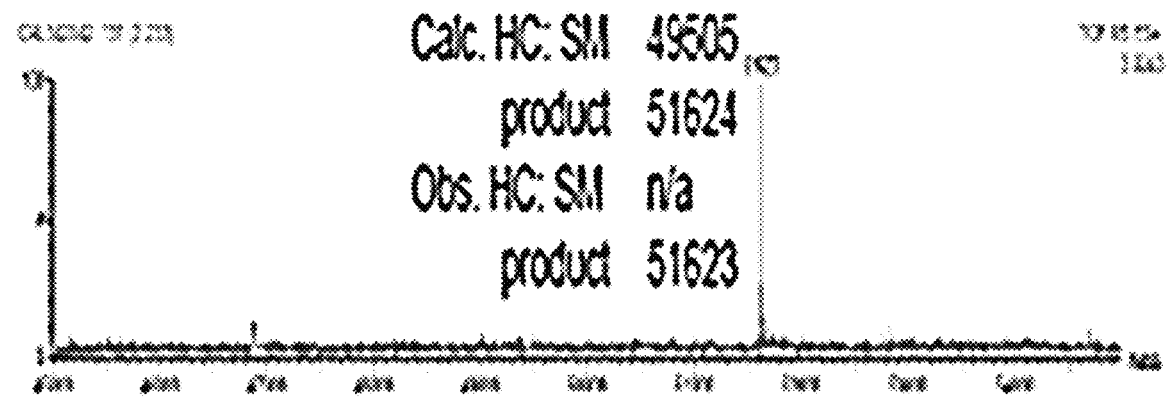
Figure 32G:
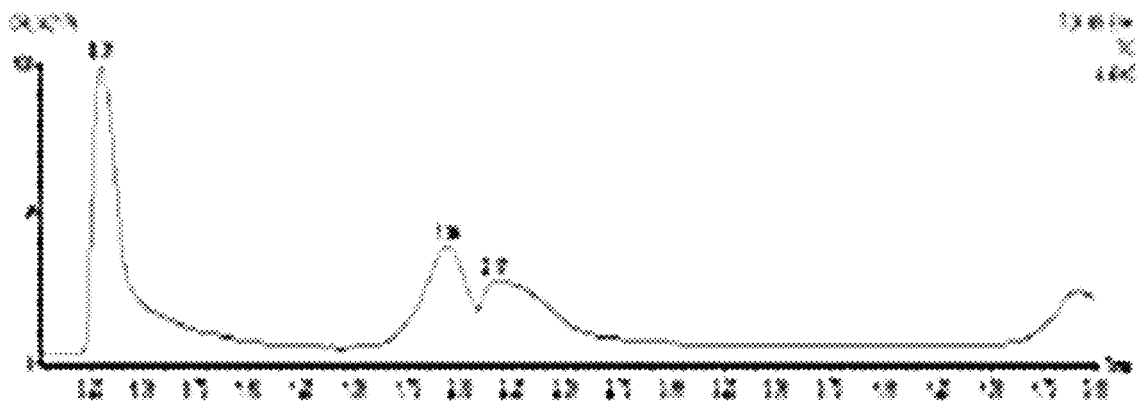
Figure 32H:
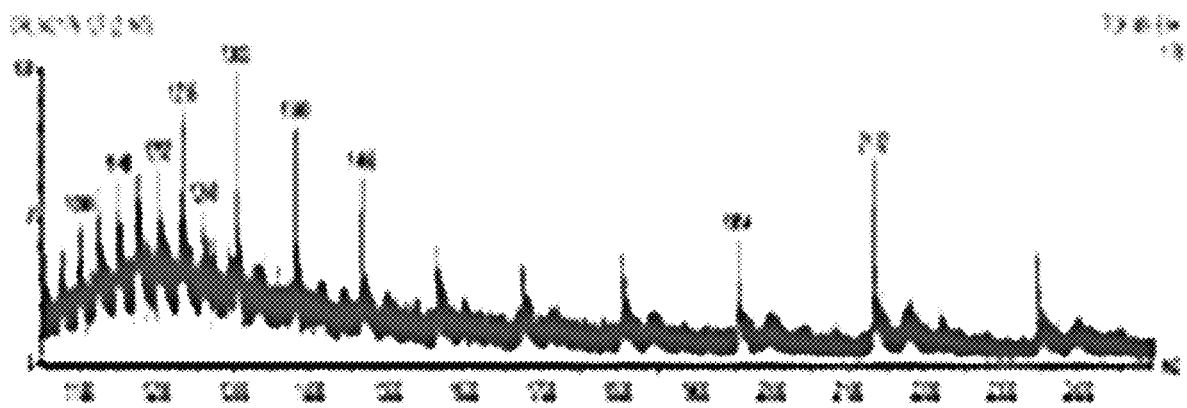
Figure 32I:
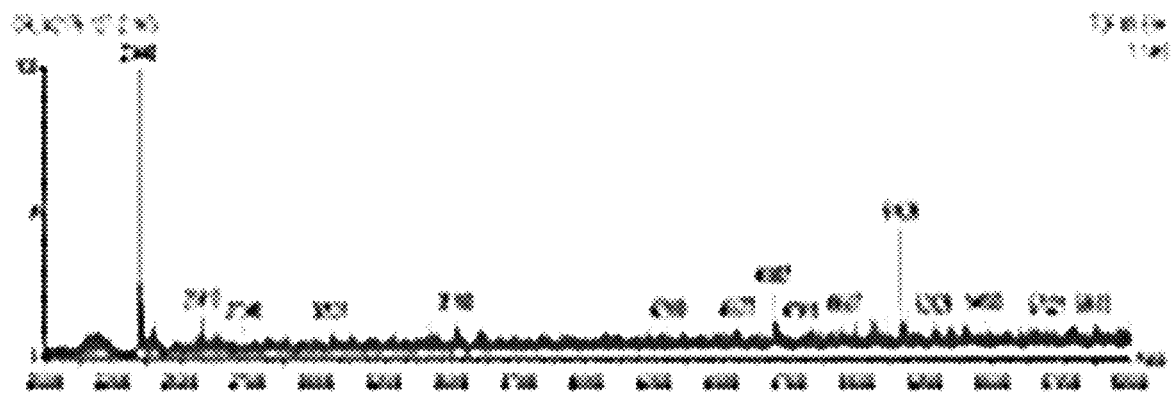
Figure 32J:
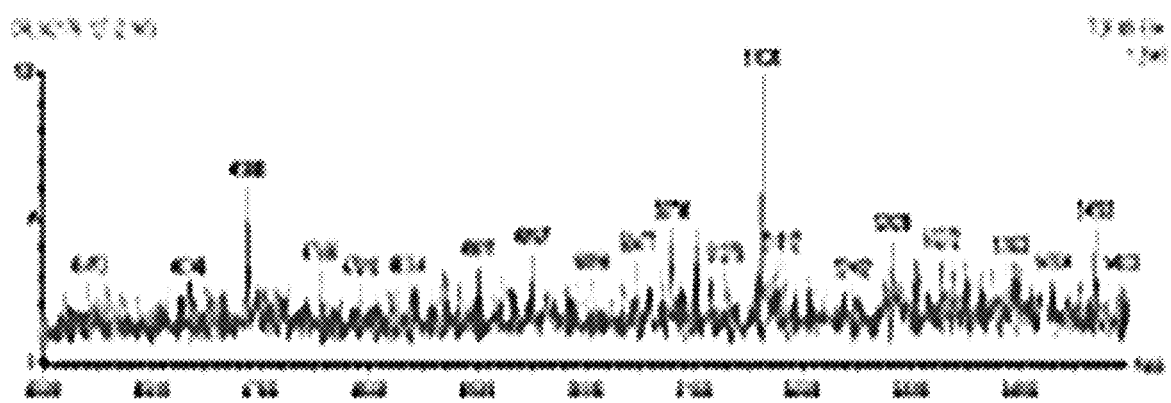
Figure 33A:
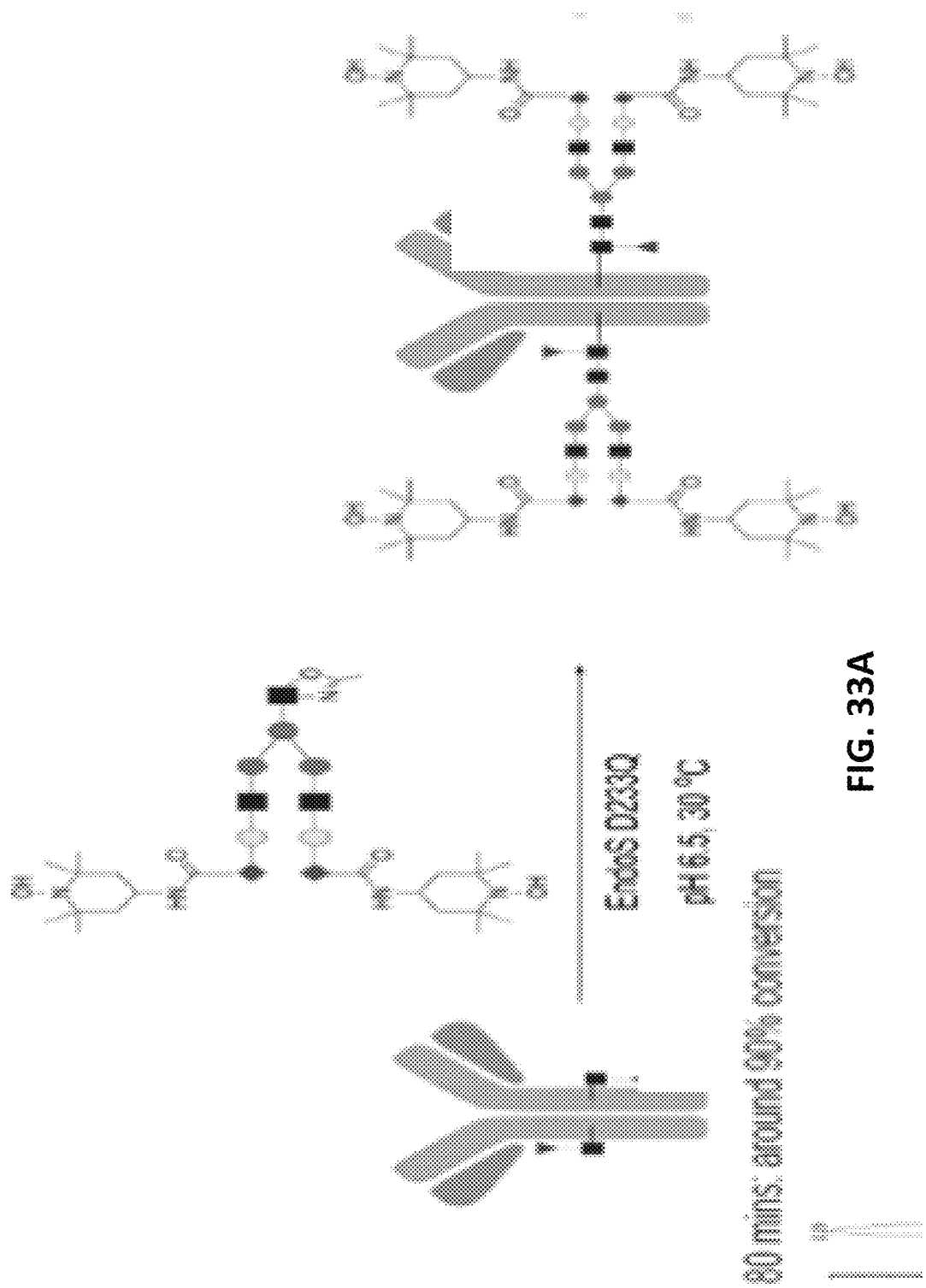
Figure 33B:
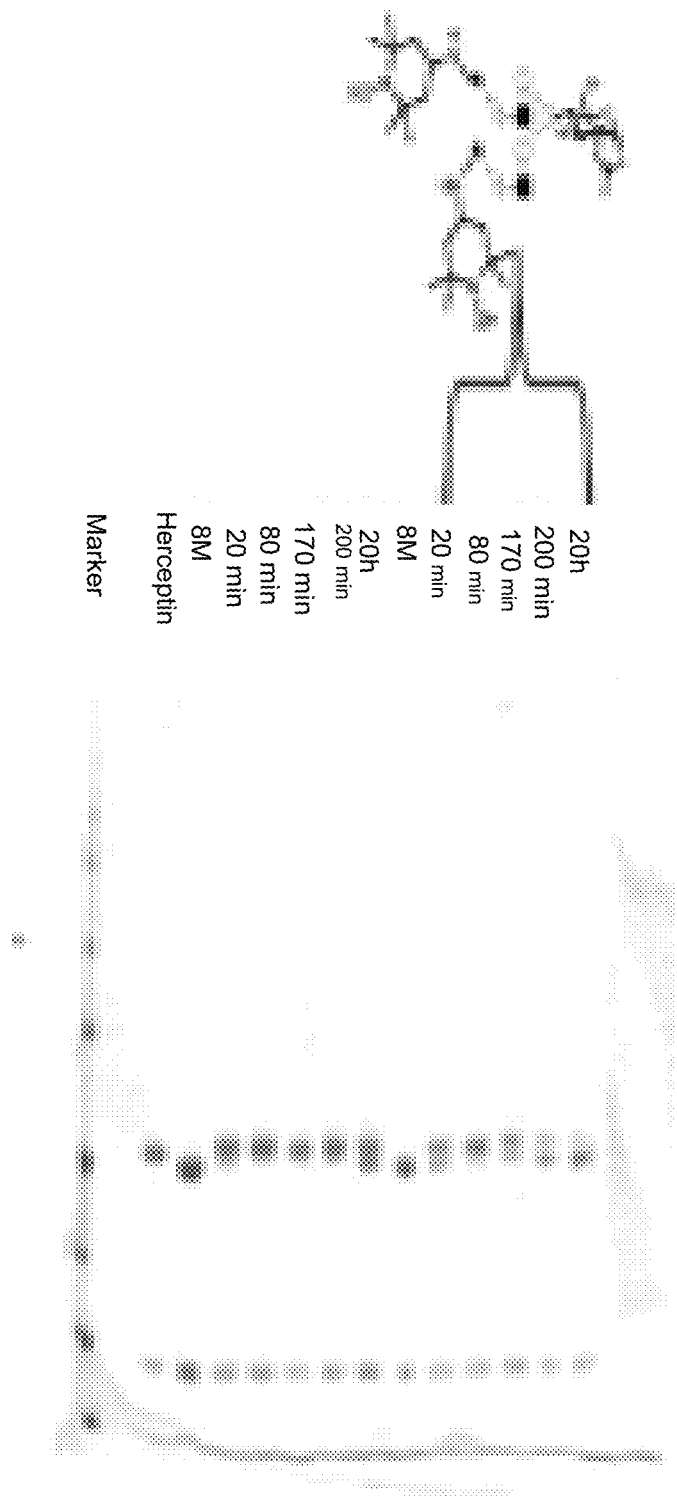
Figure 33C:
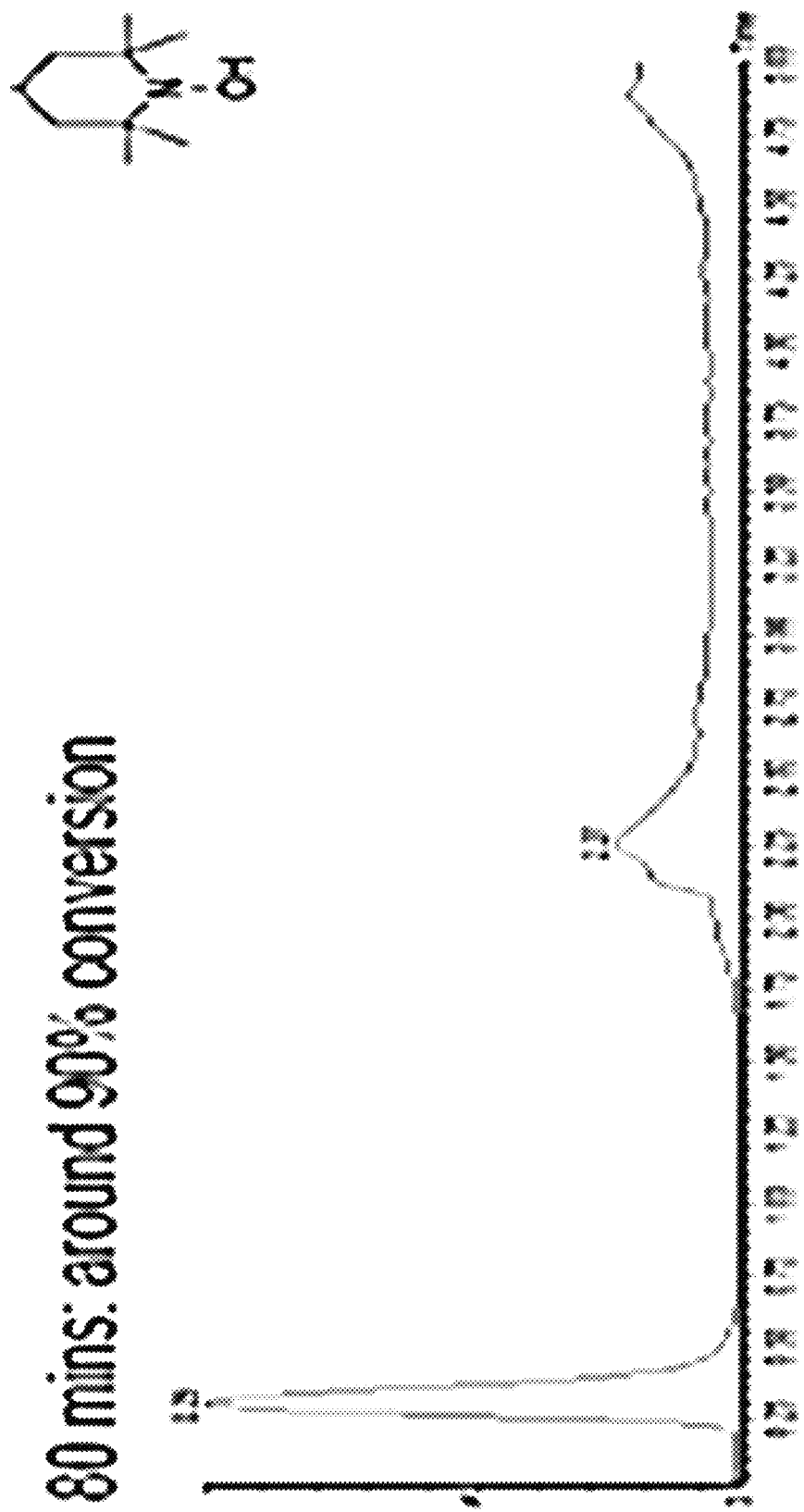
Figure 33D:
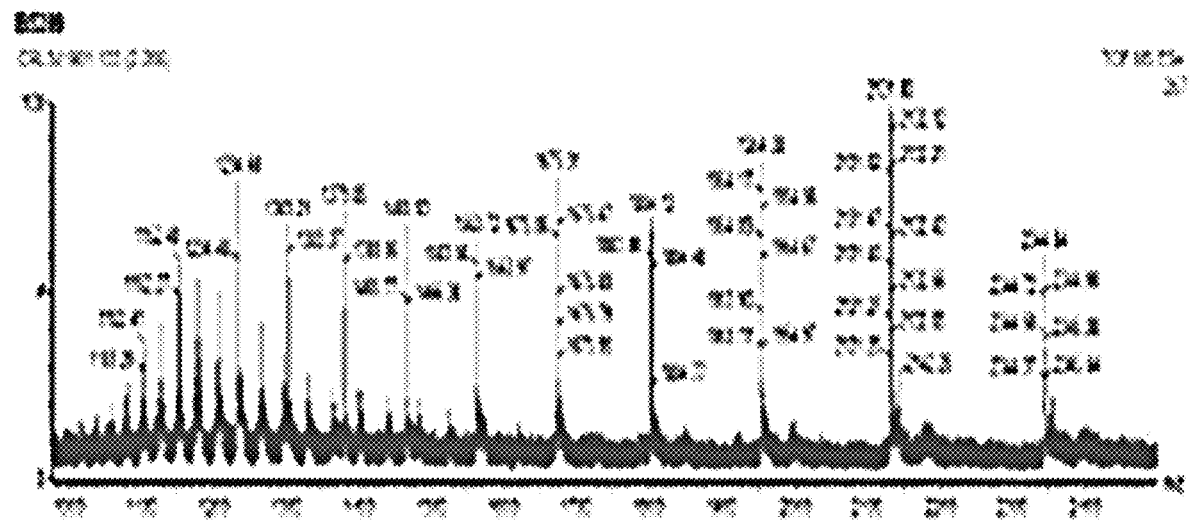
Figure 33E:
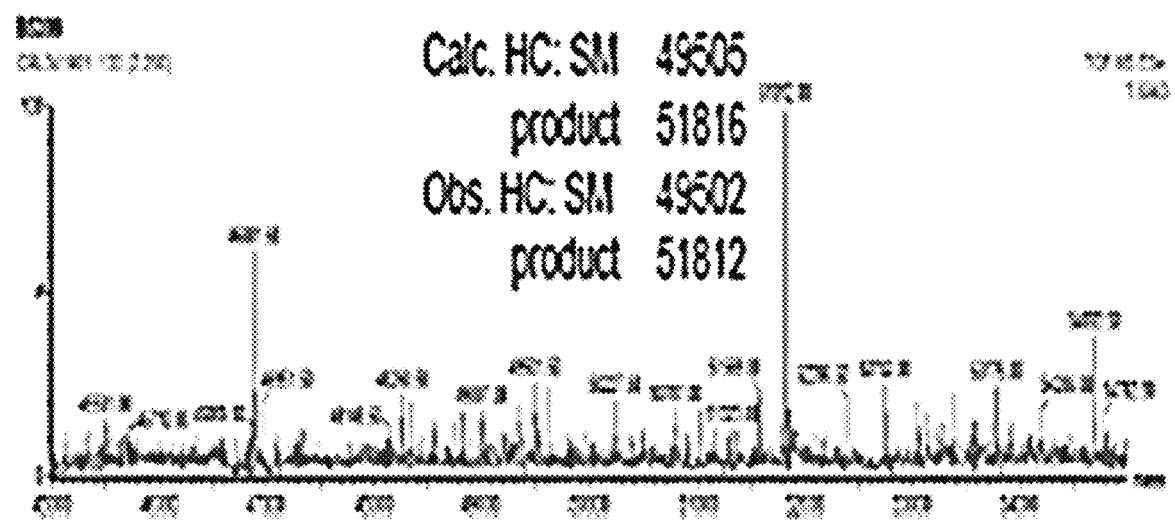
Figure 33F:
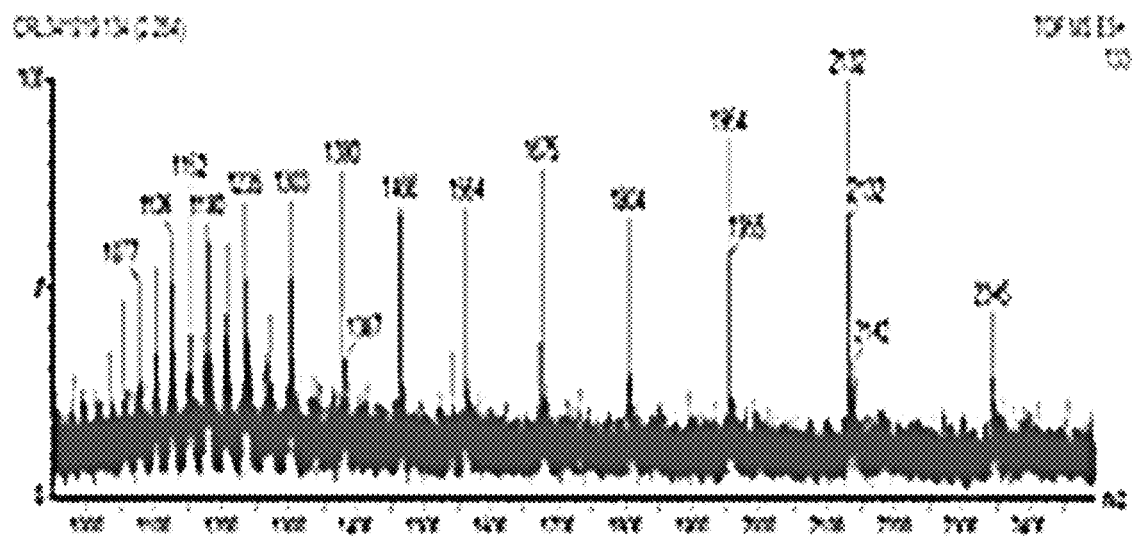
Figure 33G:
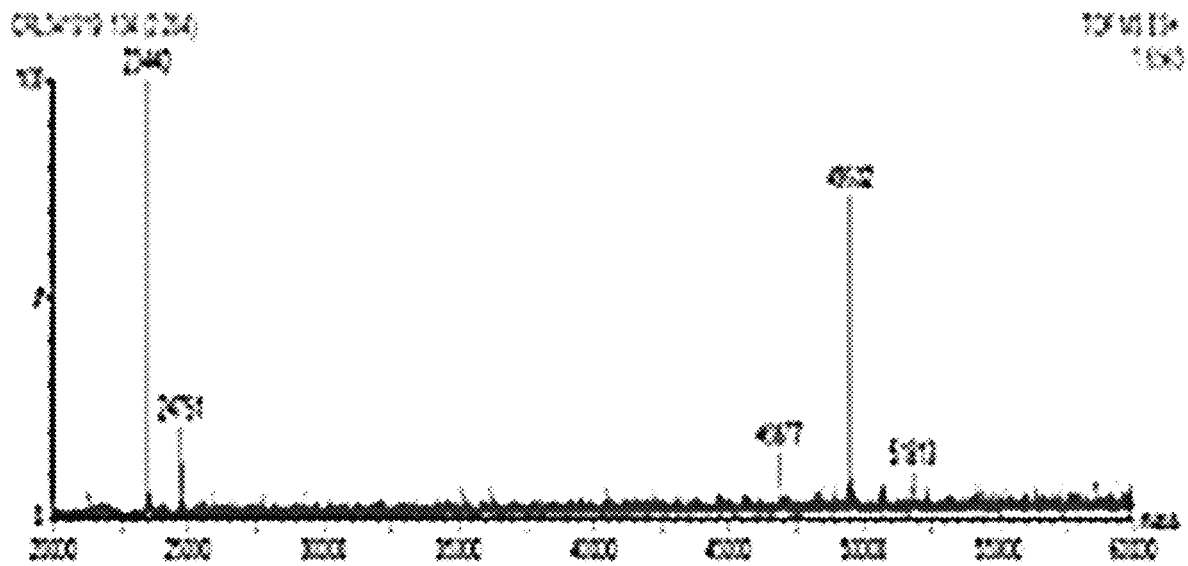
Figure 34A:
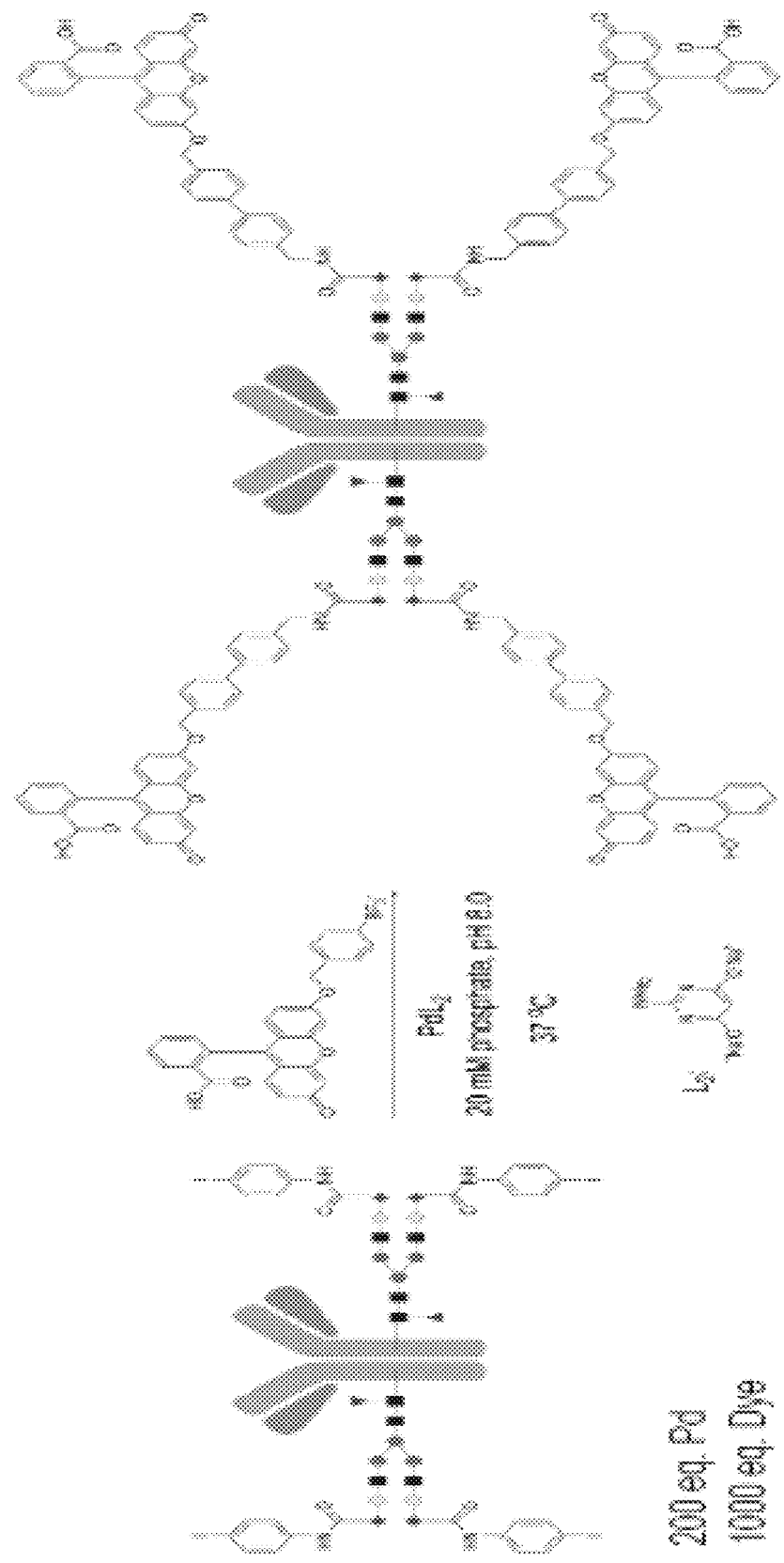
Figures 34B, 34C:
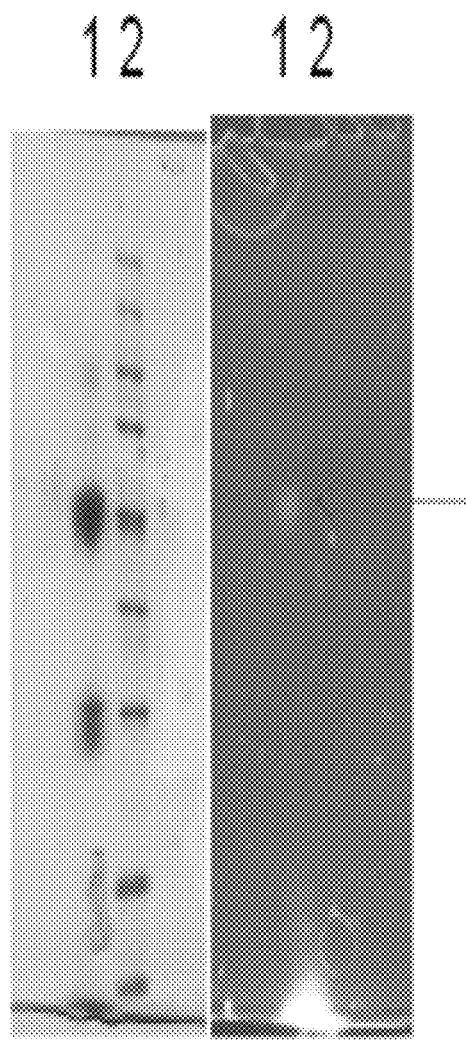
Figure 35A:
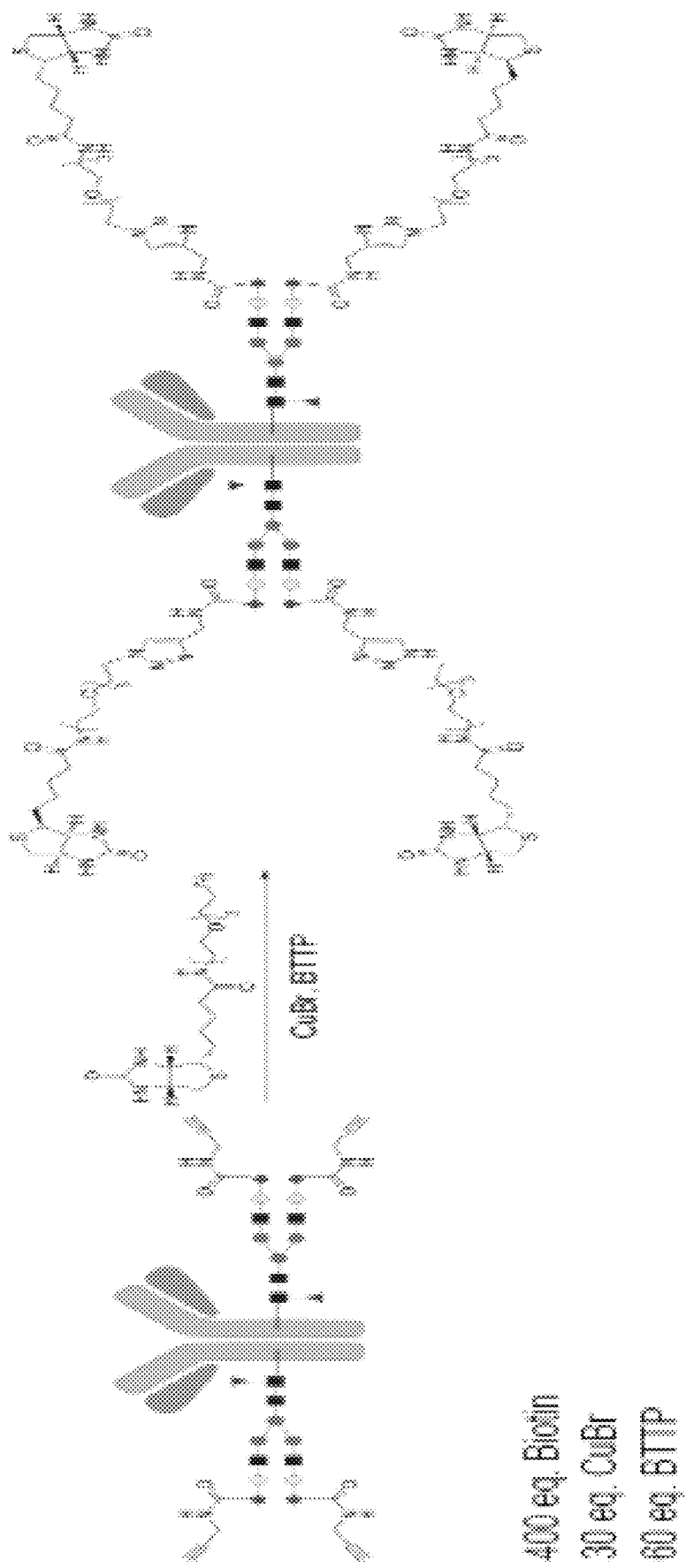
Figures 35B, 35C, 35D, 35E:
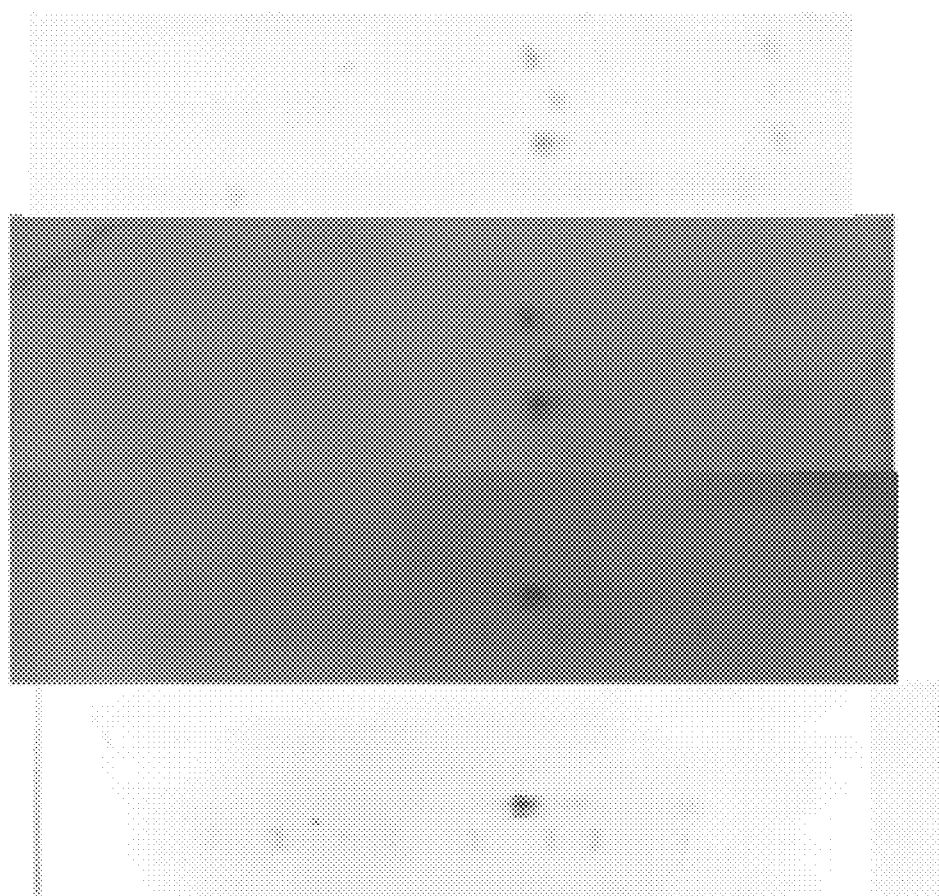
Figure 36A:
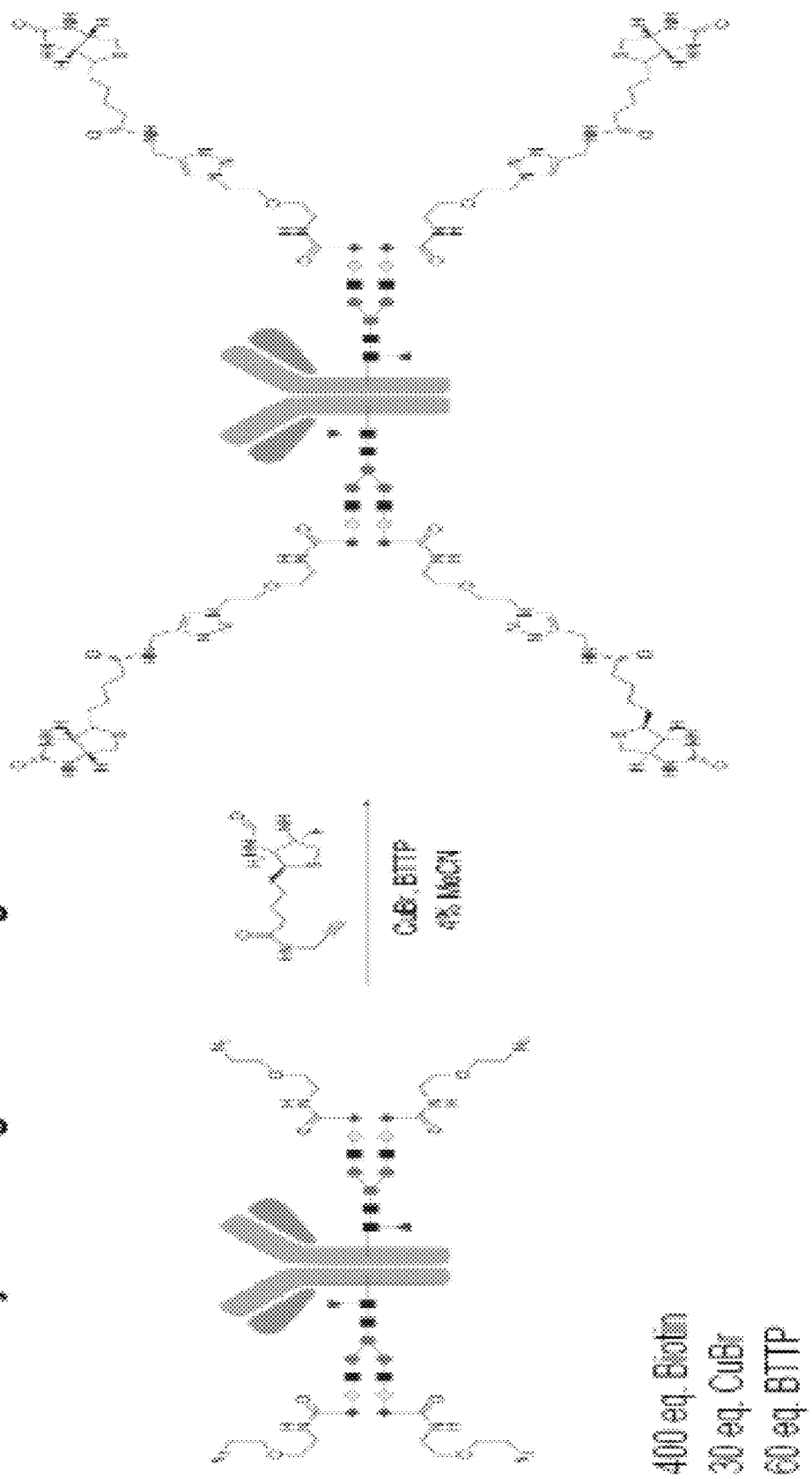
Figures 36B, 36C:
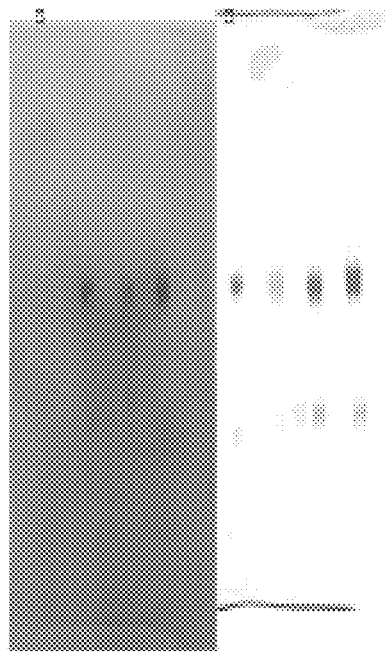
Figure 37A:
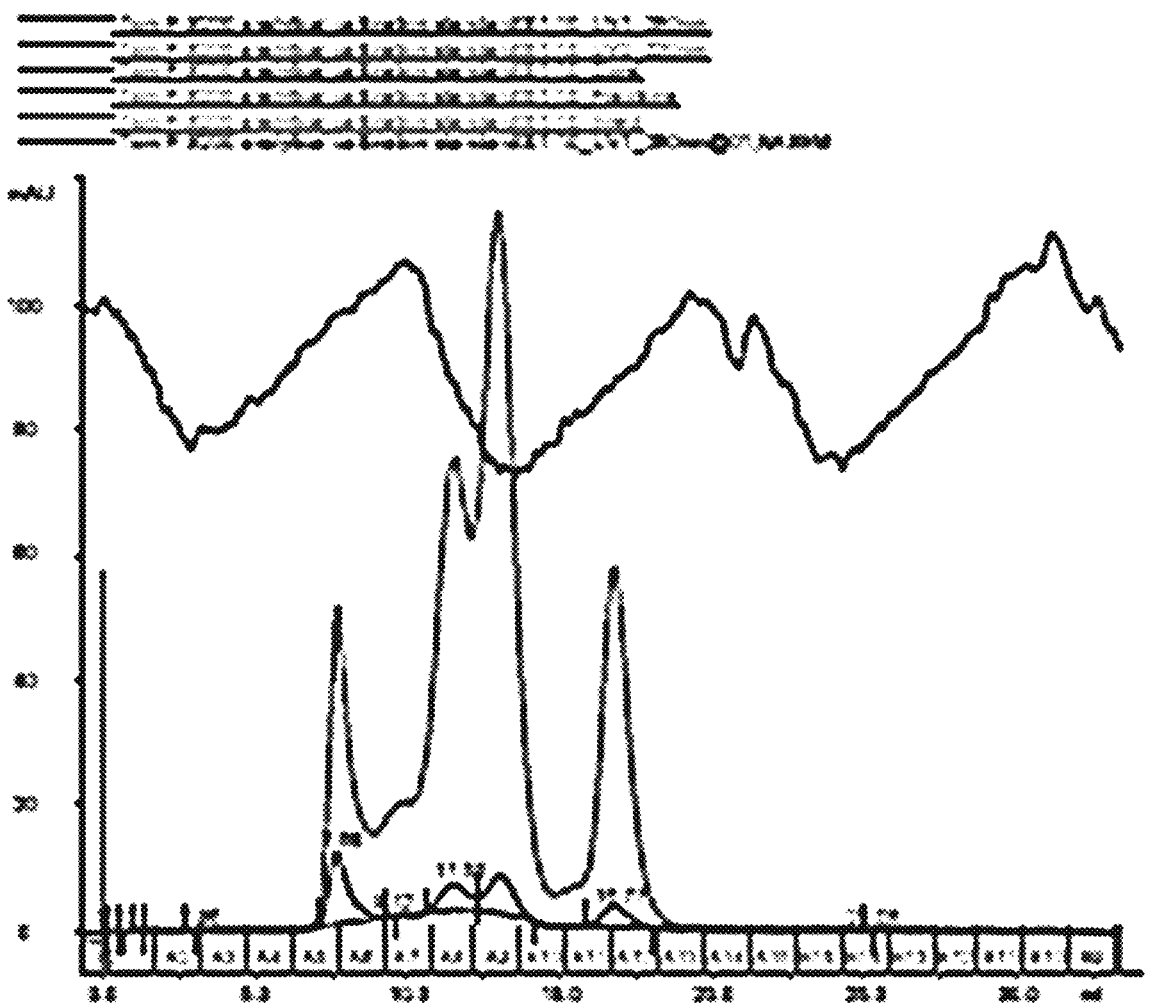
Figures 37B, 37C:
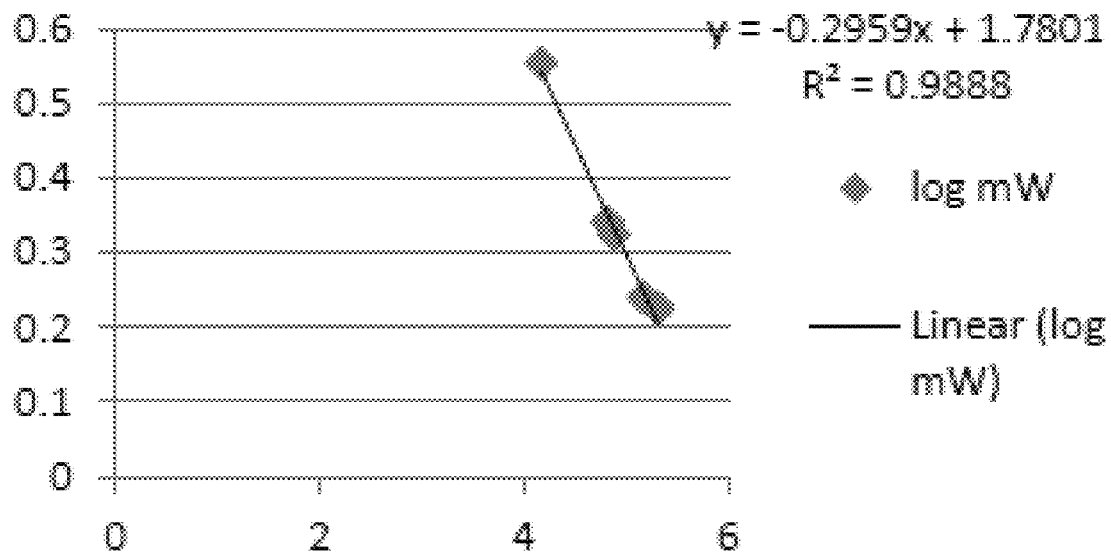
Figure 37D:
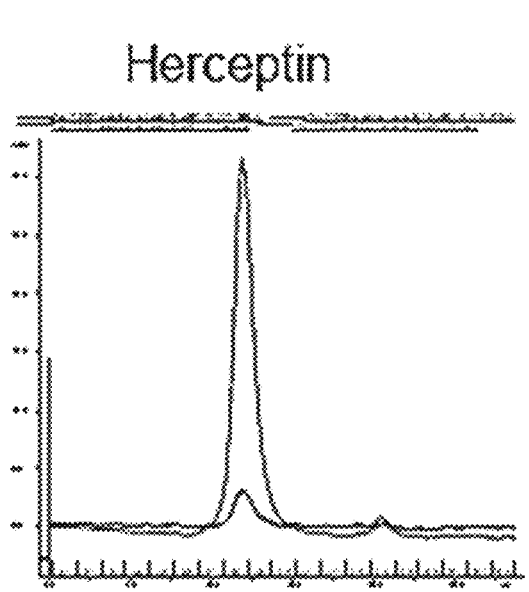
Figure 37E:
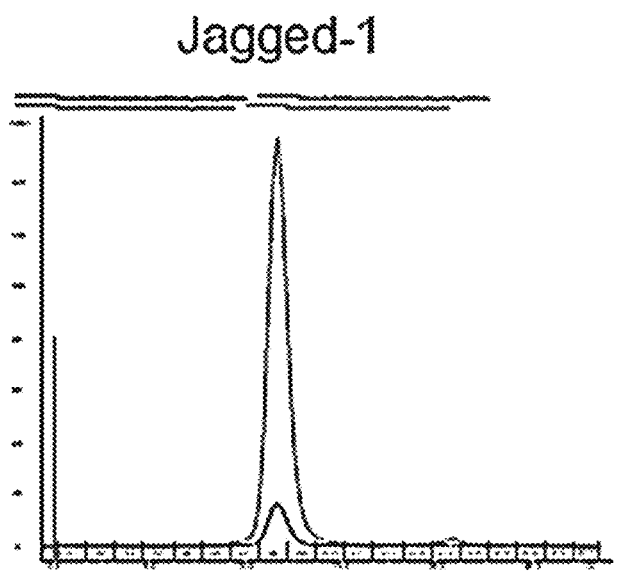
Figure 37F:
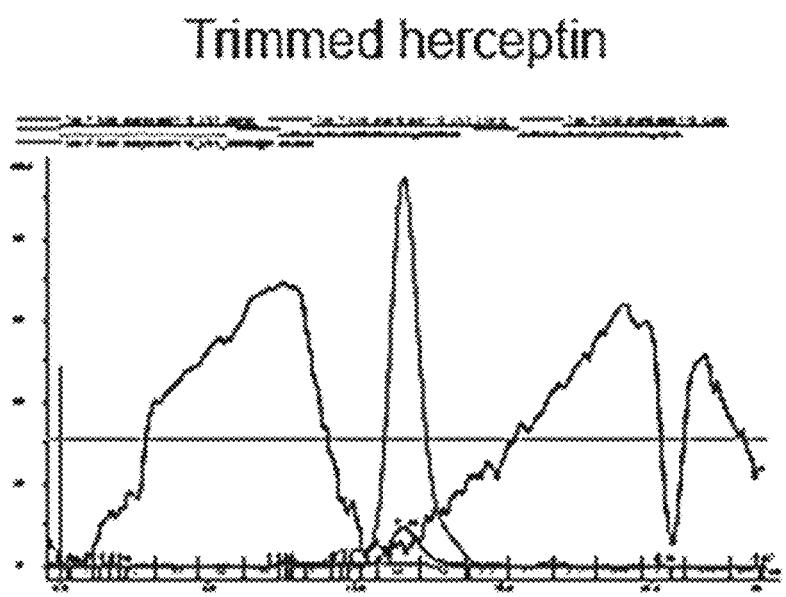
Figure 37G:
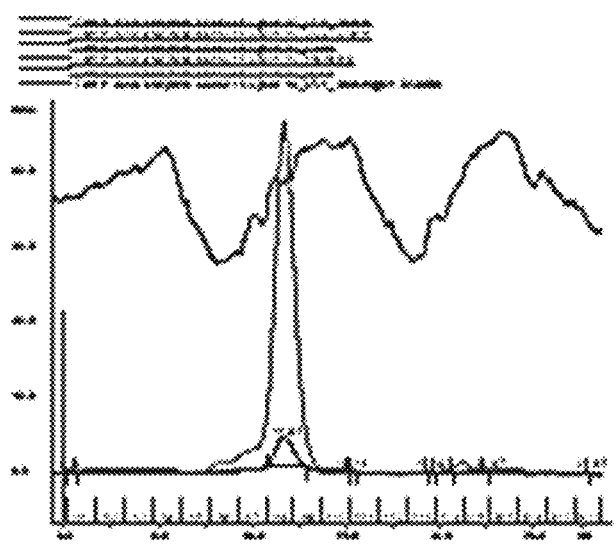
Figure 37H:
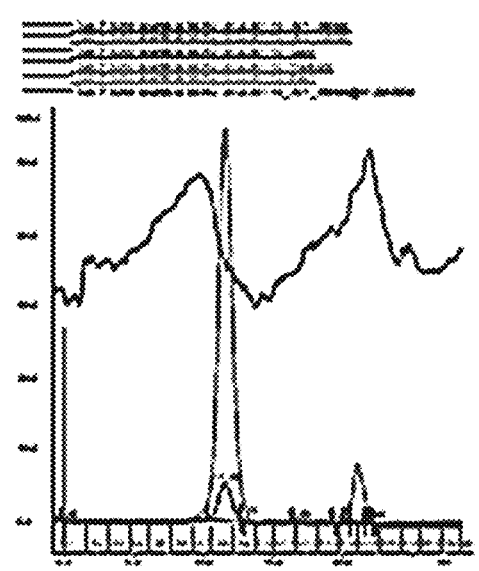
Figure 37I:
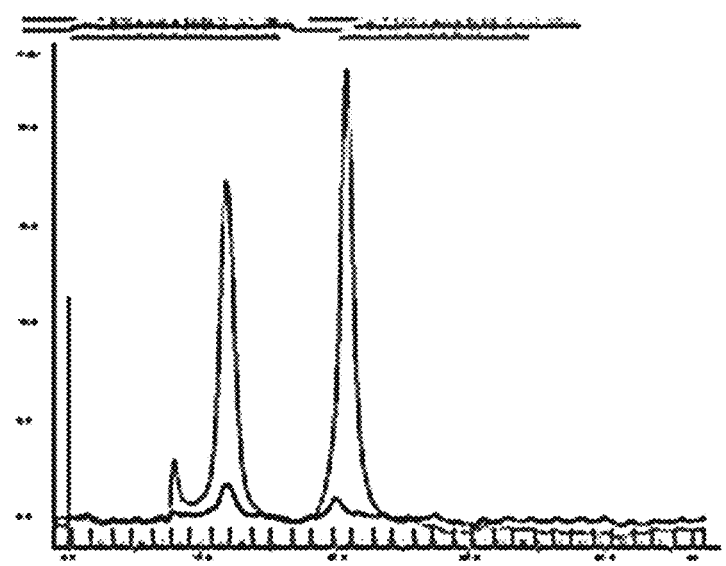

FIGS. 28A-28B demonstrate attachment of a payload molecule to a modified antibody.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this can be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

As used herein, "isolated" means separated from constituents, cellular and otherwise, with which the polynucleotide, peptide, polypeptide, protein, antibody, or fragments thereof, are normally associated in nature. A non-naturally occurring polynucleotide, peptide, polypeptide, protein, antibody, or fragments thereof, does not require "isolation" to distinguish it from its naturally occurring counterpart.

As used herein, "attached" refers to an association between two elements, molecules, compounds, and the like. Types of associations include covalent, polar covalent, ionic, non-polar, non-covalent, metallic, hydrogen bonding, and/or van der Waals interactions, hydrophobic interactions, and hydrophilic interactions. Others will be instantly appreciated by one of ordinary skill in the art.

As used herein, "specific binding," "specifically bound," and the like, refer to binding that occurs between such paired species as nucleotide/nucleotide, enzyme/substrate, receptor/agonist, antibody/antigen, and lectin/carbohydrate that can be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "chemospecifically," "chemospecific," "chemoselective," and the like refer to the control over a reaction such that the reaction or addition/deletion of a molecule only occurs at one position, residue, motif, or functional group on a molecule or compound.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "antibody" refers to a protein produced in response to an antigen and that possesses the ability to specifically bind to that antigen at an epitope.

As used herein, "epitope" refers to the part of an antigen that is recognized by an antibody and that is the part of an antigen that is recognized by the antibody and that can specifically bind an antibody.

As used herein, "separated" refers to the state of being physically divided from the original source or population such that the separated compound, agent, particle, or molecule can no longer be considered part of the original source or population.

As used herein, "peptide" refers to two or more amino acids where the alpha carboxyl group of one amino acid is bound to the alpha amino group of another amino acid. Strings of 10 or more amino acids are also referred to herein as "polypeptides" or "proteins".

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "purified" is used in reference to a nucleic acid sequence, peptide, or polypeptide or other compound described herein that has increased purity relative to the natural environment.

As used herein, "about," "approximately," and the like, when used in connection with a numerical variable, generally refers to the value of the variable and to all values of the variable that are within the experimental error (e.g., within the 95% confidence interval for the mean) or within .+-.10% of the indicated value, whichever is greater.

As used herein, "control" is an alternative subject or sample used in an experiment for comparison purposes and included to minimize or distinguish the effect of variables other than an independent variable. A "control" can be a positive control, a negative control, or an assay or reaction control (an internal control to an assay or reaction included to confirm that the assay was functional). In some instances, the positive or negative control can also be the assay or reaction control.

As used herein, "dosage form" or "unit dosage form" refers to a pharmaceutical formulation that is administered to a subject in need of treatment and generally can be in the form of tablets, capsules, sachets containing powder or granules, liquid solutions or suspensions, patches, and the like.

As used herein, "effective amount" refers to the amount of a compound or molecule that will elicit the biological or medical response of a tissue, system, animal, or human that is being sought by the researcher, veterinarian, medical doctor or other clinician. The effective amount will vary depending on the compound or molecule, the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "diluted" used in reference to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier, diluent, binders, lubricants, glidant, preservative, flavoring agent, coloring agent, and excipient" refers to a carrier, diluent, binder, lubricant, glidant, preservative, flavoring agent, coloring agent, or excipient that is useful in preparing a pharmaceutical formulation that is generally safe, non-toxic, and is neither biologically or otherwise undesirable, and includes a carrier or excipient that is acceptable for veterinary use as well as human pharmaceutical use.

As used herein, "pharmaceutically acceptable salt" refers to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "biocompatible" or "biocompatibility" refers to the ability of a material to be used by a patient without eliciting an adverse or otherwise inappropriate host response in the patient to the material or an active derivative thereof, such as a metabolite, as compared to the host response in a normal or control patient.

As used herein, "therapeutic" refers to curing or treating a symptom of a disease or condition.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

The term "preventing", as used herein includes preventing a disease, disorder or condition from occurring in an animal, which can be predisposed to the disease, disorder and/or condition but has not yet been diagnosed as having it.

The terms "sufficient" and "effective", as used interchangeably herein, refer to an amount (e.g. mass, volume, dosage, concentration, and/or time period) needed to achieve one or more desired result(s). For example, a therapeutically effective amount refers to an amount needed to achieve one or more therapeutic effects.

As used herein, "preventative" refers to hindering or stopping a disease or condition before it occurs or while the disease or condition is still in the sub-clinical phase.

As used herein, "mitigate" refers to reducing a particular characteristic, symptom, or other biological or physiological parameter associated with a disease or disorder.

As used herein, "active derivative" and the like refer to a derivative of an autophagic inhibitor that retains an ability to treat/mitigate plasma cell proliferation and/or secondary complications associated with endometriosis. Assays for testing the ability of an active derivative to perform in this fashion are known to those of ordinary skill in the art.

As used herein, "metabolite" refers to substances that result from metabolism of a compound, such as an active agent of a pharmaceutical formulation.

As used herein, "active metabolite" refers to a metabolite that induces a pharmaceutical or clinical effect in a subject.

As used herein, "primary metabolite" refers to a metabolite that is directly involved in growth, development, and/or reproduction of a cell or organism.

As used herein, "secondary metabolite" refers to a metabolite that is not directly involved in growth, development, and/or reproduction of a cell or organism.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide can differ in amino acid sequence by one or more modifications (e.g., substitutions, additions, and/or deletions). A substituted or inserted amino acid residue can or cannot be one encoded by the genetic code. A variant of a polypeptide can be naturally occurring such as an allelic variant, or it can be a variant that is not known to occur naturally.

As used herein, "wild-type" or "native" refers to the typical and non-mutated form of an organism, variety, strain, gene, protein, or characteristic as it occurs in nature, as distinguished from mutant forms that can result from selective breeding or transformation with a transgene.

As used herein, "emollients" refers to an externally applied agent that softens or soothes skin and are generally known in the art and listed in compendia, such as the "Handbook of Pharmaceutical Excipients", $4^{th}$ Ed., Pharmaceutical Press, 2003.

As used herein, "surfactants" refers to surface-active agents that lower surface tension and thereby increase the emulsifying, foaming, dispersing, spreading and wetting properties of a product.

As used herein, "emulsifiers" refers to surface active substances which promote the suspension of one liquid in another and promote the formation of a stable mixture, or emulsion, of oil and water.

As used herein, "oil" refers to a composition containing at least about 95% wt of a lipophilic substance. Examples of lipophilic substances include but are not limited to naturally occurring and synthetic oils, fats, fatty acids, lecithins, triglycerides and combinations thereof.

As used herein, "emulsion" is a composition containing a mixture of non-miscible components homogenously blended together. The non-miscible components can include a lipophilic component and an aqueous component. "Emulsion" can also refer to a preparation of one liquid distributed in small globules throughout the body of a second liquid. The first liquid is the discontinuous phase and the second liquid is the continuous phase. When oil is first liquid and water or an aqueous solution is the second liquid, it is referred to herein as an "oil in water emulsion". When water or an aqueous solution is the first liquid and oil or oleagionous substance is the second liquid, it is referred to herein as "water-in-oil" emulsion". Either or both of the oil phase and aqueous phase can contain one or more surfactants, emulsifiers, emulsion stabilizers, buffers, and other excipients. Some emulsions can be gels or otherwise include a gel component.

As used herein, "lotion" refers to a low- to medium-viscosity liquid formulation. "Lotions" can contain finely powdered substances that are in soluble in the dispersion medium through the use of suspending agents and dispersing agents. "Lotions" can also have as the dispersed phase liquid substances that are immiscible with the vehicle and are usually dispersed by means of emulsifying agents or other suitable stabilizers.

As used herein, "cream" refers to a viscous liquid or semi-solid emulsion of either the "oil-in-water" or "water-in-oil type".

As used herein, "ointment" refers to a semisolid preparation containing an ointment base and optionally one or more active agents.

As used herein in the context of pharmaceutical formulations, "gel" refers to a semisolid system containing dispersions of the autophagic inhibitor in a liquid vehicle that is rendered semisolid by the action of a thickening agent or polymeric material ("gelling agent") dissolved or suspended in the liquid vehicle. The liquid can include a lipophilic component, an aqueous component or both. "Gels" can also be emulsions. Some gels, however, are not emulsions because they do not contain a homogenized blend of immiscible components.

Discussion

Targeted therapy is a modality of therapy for diseases, including cancer, in which a drug or other compound or molecule is delivered to a pre-determined specific location, cell, or cell type. Targeted therapy seeks to improve treatment of diseases, inter alia, by reducing side effects and toxicity due to interactions with non-diseased cells, increasing efficacy by increasing specificity, and reducing the necessary effective dose amounts.

There have been many approaches to targeted therapy. Some targeted therapies include small molecules that have limited action on one or a few pathways involved in pathogenesis of a disease. In other targeted therapies, small molecule drug conjugates that contain a small molecule drug compound can be conjugated to another small molecule compound that acts as a targeting moiety. In some instances the additional small molecule compound is a substrate for a receptor on a target cell. Additional examples of targeted therapies include antibodies, which are inherently specific for the epitope they are raised against and thus can specifically bind and block mediators of disease. Antibodies raised against immune components, such as interferon, have been developed to treat inflammatory diseases such as arthritis.

Due to their ability to bind epitopes specifically, there have been attempts at utilizing antibodies or fragments thereof as a targeting moiety for targeted delivery of small molecules. While in theory this sounds like an ideal drug conjugate for use in targeted therapy, the full potential for antibody drug conjugates has failed to be realized. Although there are more than 30 antibody drug conjugates currently in clinical trials, to date only three (3) antibody-drug conjugates have received market approval: Gemtuzumab ozogamicin (Mylotarg®), Brentuximab vedoti (Adcetris®), and (Trastuzumab emtansine (Kadcyla®). Recently, Mylotarg® was withdrawn from the market due to increased patient death and no demonstrated benefit over conventional cancer therapies.

Even the two remaining approved antibody-drug conjugates are marked with significant warnings. The boxed warning for Adcetris® states "Progressive multifocal leukoencephalopaty(PML): JC virus infection resulting in PML and death can occur in patients receiving ADCETRIS." The manufacturers of Adcetris® also warns that treatment with Adcetris® can result in peripheral neuropathy, infusion-related reactions, hematologic toxicities, serious infections, opportunistic infections, tumor lysis syndrome, Steven- Johnson syndrome, and fetal harm. The boxed warning for Kadcyla® states that hepatotoxicity, liver failure, and death have occurred due to Kadcyla® treatment, that Kadcyla® may lead to heat damage (reductions in left ventricular ejection fraction), and that Kadcyla® can cause fetal harm. Other warnings provided in the Kadcyla® prescribing information includes that Kadcyla® may result in pulmonary toxicity, fatal hemorrhages, thrombocytopenia, infusion-related reactions, and neurotoxicity.

The high failure rate and undesired off-target effects of current antibody-drug conjugates can be attributed, at least in part, to non-selective attachment of the drug molecule to the antibody, heterogeneous glycoforms of the antibodies in a given drug composition, linker stability, and variation in loading of the drug on the antibody. Non-selective attachment of the drug molecule can result in potentially toxic batch-to-batch variation and/or reduced or variable efficacy. Heterogeneous glycoforms can result in variability in antibody efficacy and effect attachment of the drug to the antibody. Loading variation can result in potentially toxic batch-to-batch inconsistencies in efficacy of the resulting antibody-drug conjugate. Poor linker stability can result in drug action at off-target sites.

With these deficiencies in mind, described herein are antibody conjugates and pharmaceutical formulations thereof that can have a payload molecule, such as a drug compound, chemospecifically attached to an antibody via a linker and bioorthogonal reaction pair, where the glycoform of the antibody can be controlled and loading variation can be minimized. Also described herein are methods of manufacturing the antibody conjugates and components thereof.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Antibody Conjugates

Described herein are antibody conjugates having an oligosaccharide, such as glycan, chemospecifically attached at an acceptor site on the antibody, where the oligosaccharide is attached via linker to a first member of a bioorthogonal reaction handle pair. The first member of the bioorthogonal reaction handle pair can be attached to a second member of the bioorthogonal reaction pair. A payload molecule can be attached to the second member of the bioorthogonal reaction pair via a linker. As demonstrated in FIG. 1, at least 2 payload molecules per oligosaccharide can be loaded onto the antibody. In some embodiments, at least two oligosaccharides linked to a first member of a bioorthogonal reaction handle pair are attached to an antibody.

In some embodiments, the antibody can be conjugated as described above to a single type of payload molecule. These antibody conjugates can be referred to as homogenously loaded antibody conjugates. In other embodiments, the antibody can be conjugated with at least two different types of payload molecules. These antibody conjugates can be referred to as heterogeneously loaded antibody conjugates.

The oligosaccharide can be chemospecifically attached to the antibody. In some embodiments, the oligosaccharide can be attached at a chemospecific acceptor site on the antibody. Antibodies are glycoproteins and contain specific sites (e.g. specific amino acids) that oligosaccharides can attach to. Two such chemospecific acceptor sites on an antibody are N-glycosylation and O-glycosylation sites. The N-glycosylation sites can be asparagine residues. The O-glycosylation sites can be hydroxylysine, hydroxyproline, serine, or threonine. In some embodiments, oligosaccharide(s) can be attached to a conserved chemospecific acceptor site. The conserved chemospecific acceptor sits can be located on the Fc fragment of the antibody. The conserved chemospecific acceptor site can be N-glycosylation site. The conserved chemospecific site can be an asparagine residue. In some embodiments, the chemospecific receptor site can be Asparagine 297. In embodiments where the chemospecific receptor site is Asparagine 297, two oligosaccharides per antibody can be attached to the antibody: one on each heavy chain. In some embodiments, the oligosaccharide(s) is only attached to a conserved chemospecific acceptor site(s). As is described elsewhere herein, the antibody can be engineered to specifically utilize particular chemospecific acceptor and exclude others. In some embodiments, the conserved chemospecific acceptor site(s) can be in the heavy chain constant region of an antibody.

Insofar as the antibody conjugates described herein can be generated using bioorthogonal reaction chemistry, the payload molecules can be attached to the antibody in a chemoselective manner. Further, the modular design of the antibody conjugates herein offer a dynamic antibody platform that can be easily coupled to multiple types of payload molecules based on coordination of bioorthogonal reaction handles attached to the payload molecules and the oligosaccharides. Thus, one antibody with selective addition of an oligosaccharide can serve as a host to a myriad of payload molecules so long as the bioorthogonal reaction handle attached to the payload molecule selectively reacts and attaches to the bioorthogonal reaction handle attached to the oligosaccharide on the antibody.

Antibodies

The antibody conjugates contain an antibody or fragment thereof. The antibody can be a monoclonal antibody (mAb). Methods of engineering, generating, screening, and selecting monoclonal antibodies for a particular target epitope are generally known in the art. See e.g. Antibodies: A laboratory Manual, Second Edition. Ed. Edward A. Greenfield. 2014. Cold Spring Harbor Laboratory Press. The antibody or fragment thereof can be of any isotype. In other words, the antibody can be IgA1, IgA2, IgD, IgE, IgG1, IgG2a, IgG2b, IgG3, IgG4, or IgM heavy chain. The antibody can have either a lambda or kappa light chain. As previously discussed, the antibody can have one or more chemospecific acceptor sites. The antibody can be humanized or otherwise optimized for the subject being treated. Methods to humanize or optimize antibodies are generally known in the art.

Figure 3:
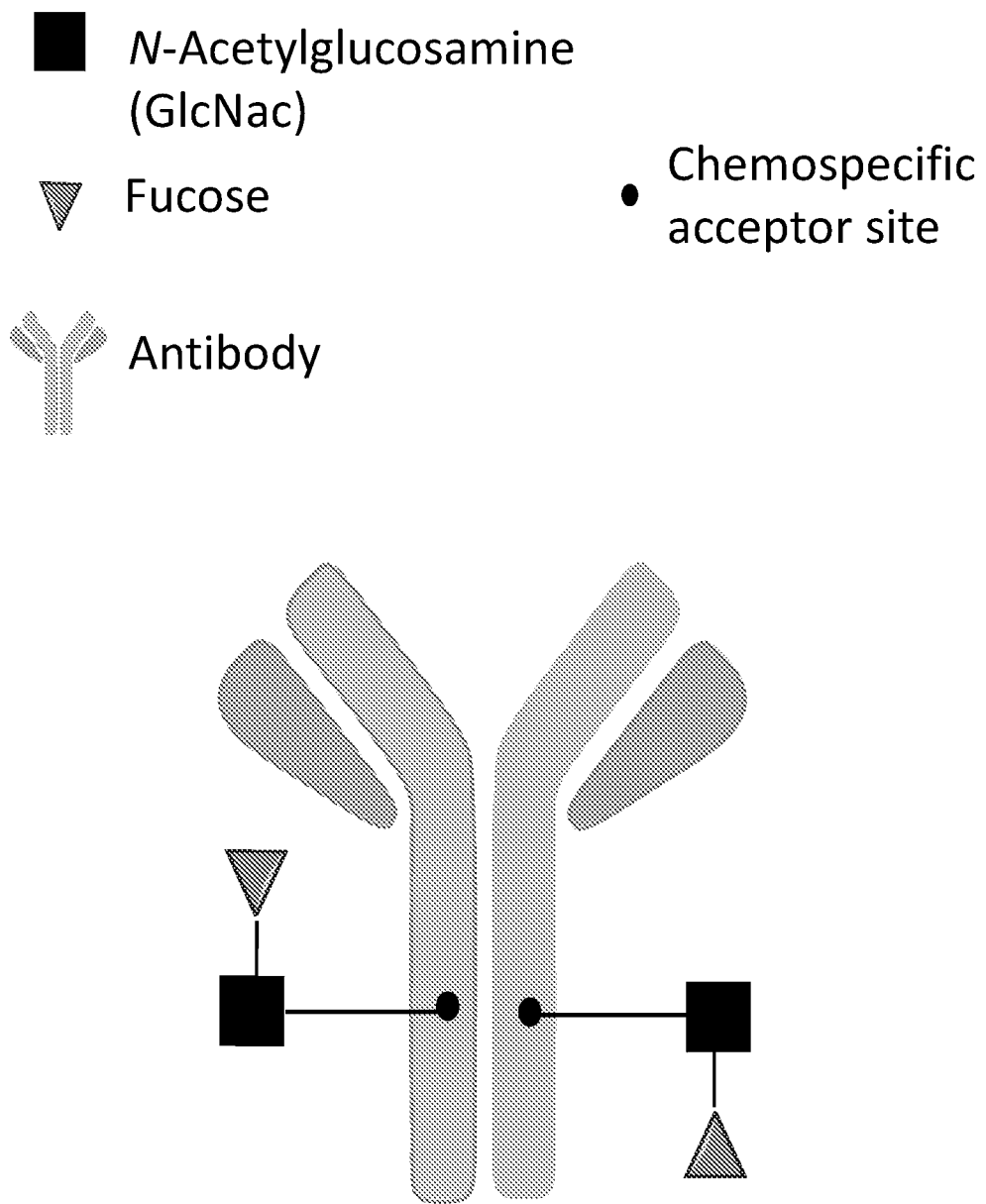
FIG. 3 shows one embodiment of a modified antibody for use in the antibody conjugate as described herein.

In some embodiments, the antibody can be modified to alter the glycosylation pattern on the antibody. The modified antibody can be completely devoid of glycans or fragments thereof. The modified antibody can contain only a N-acetylglucosamine and a fucose attached to one or more of the N-linked chemospecific acceptor sites on the antibody. In some embodiments, the glycans present on the two (2) conserved N-linked glycosylation sites on the Fc portion of the antibody can be modified to each contain only a N-acetylglucosamine and a fucose. Embodiments of a modified antibody are shown in FIG. 3. The modified antibody can then be reacted with an oligosaccharide that is attached to one member of a bioorthogonal reaction handle pair. Methods of modifying the antibody are described elsewhere herein.

Figure 4:
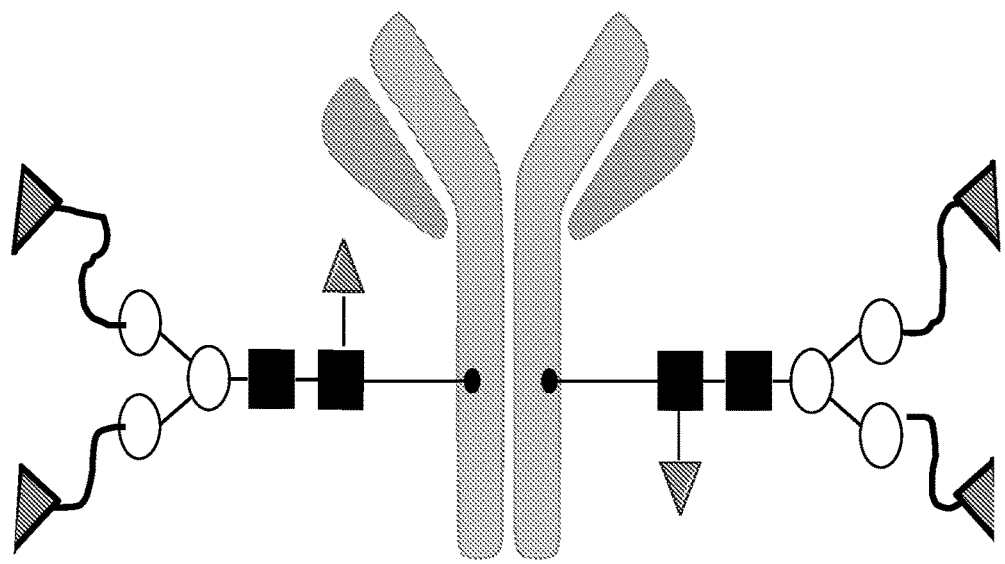
FIG. 4 shows one embodiment of a modified and remodeled antibody for use in the antibody conjugate as described herein.

In some embodiments, the antibody can be modified to alter the glycosylation pattern on the antibody and subsequently remodeled to include specific oligosaccharides at specific acceptor sites on the antibody. Methods of modifying and remodeling the antibody are described elsewhere herein. One embodiment of a modified and remodeled antibody is demonstrated shown in FIG. 4.

Oliqosaccharides

Figure 1:
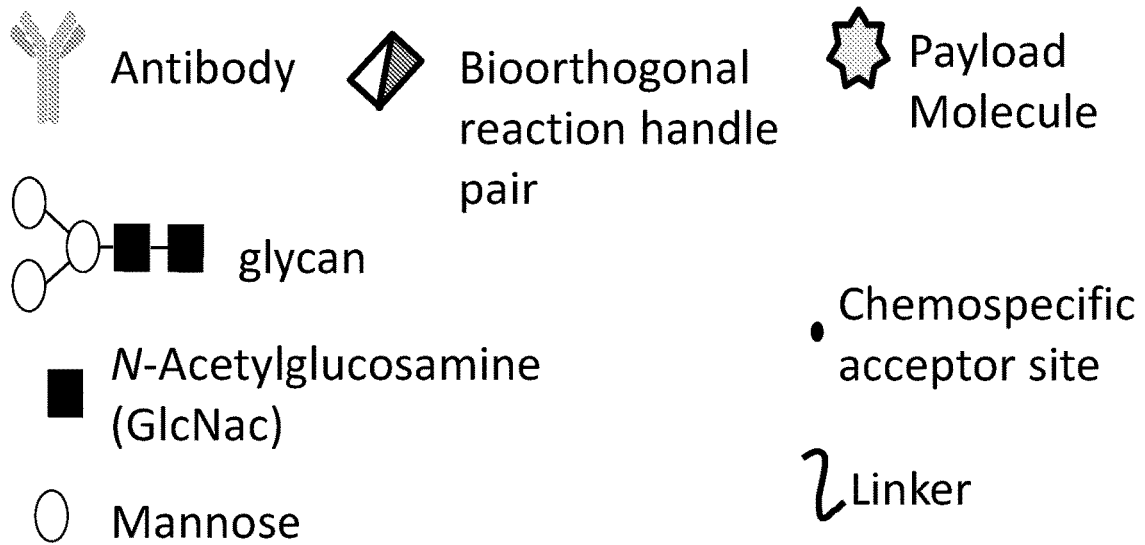
FIG. 1 shows one embodiment of an antibody conjugate as described herein.
Figure 1:
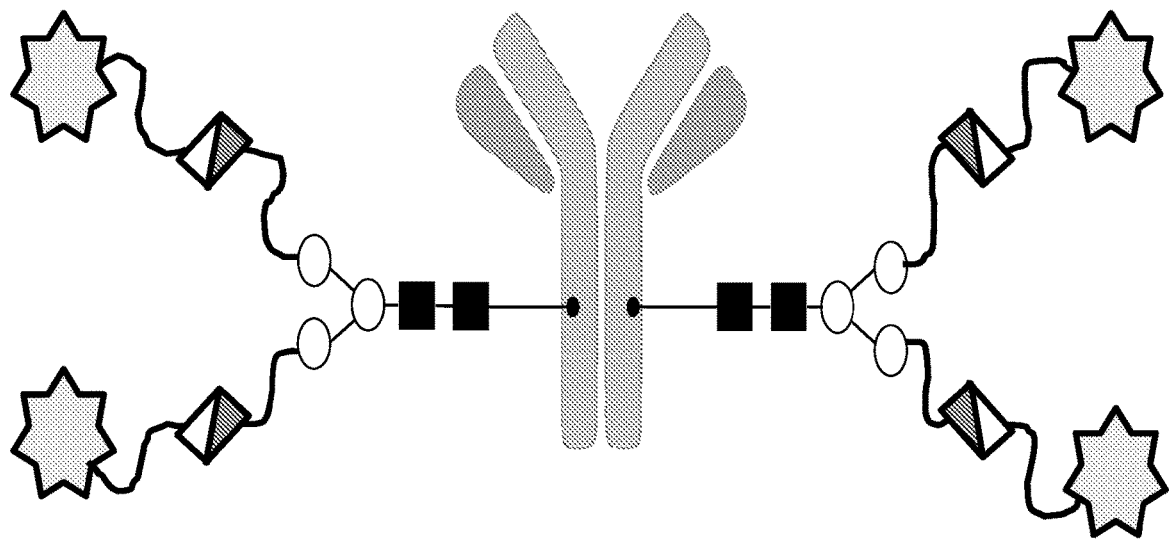
Figure 2:
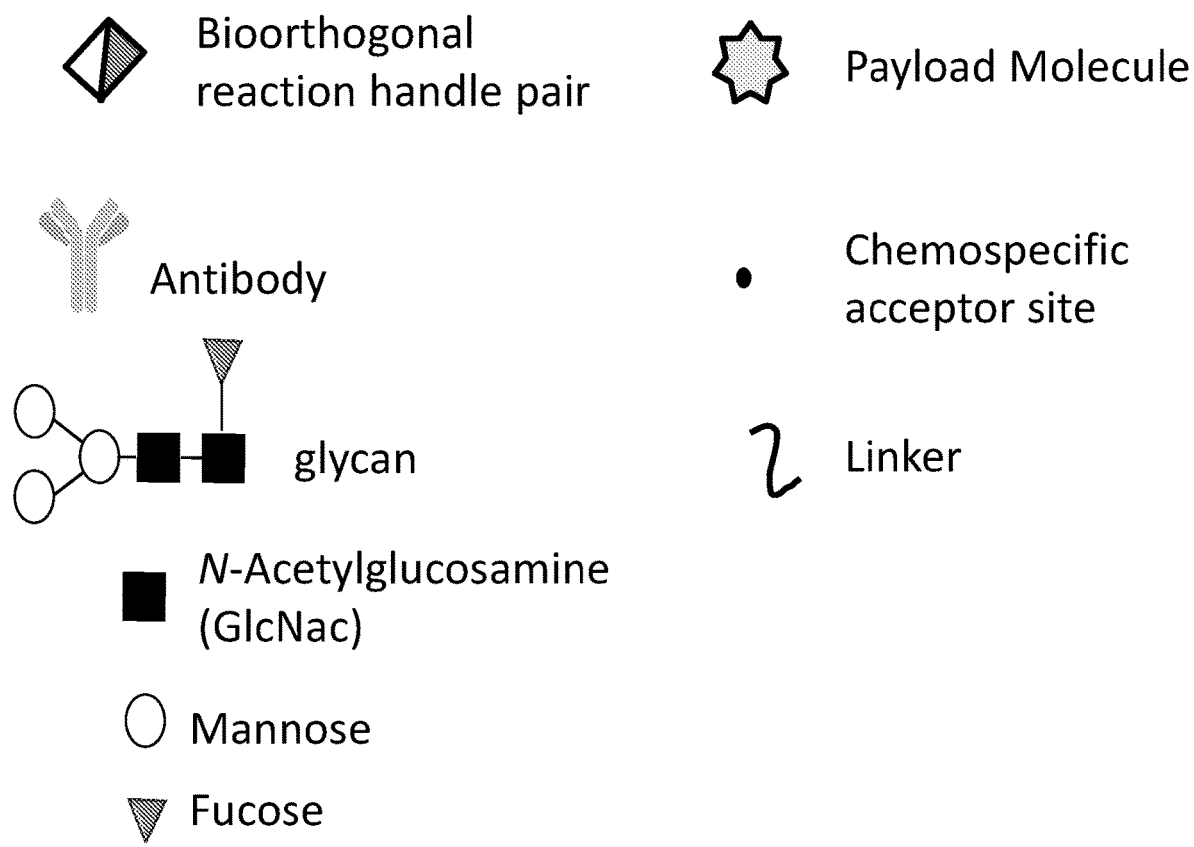
FIG. 2 shows another embodiment of an antibody conjugate as described herein.
Figure 2:
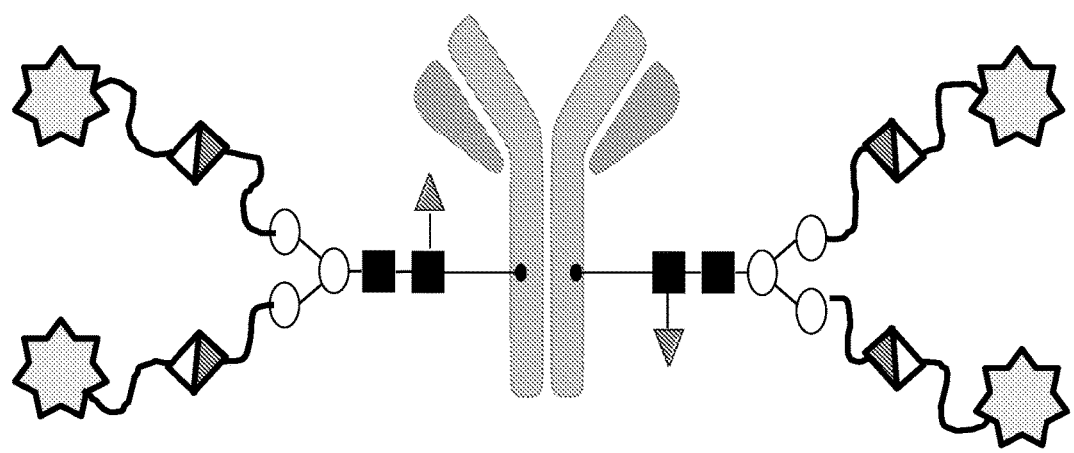

The antibody conjugates described herein contain at least one oligosaccharide attached to the antibody. The oligosaccharide can be any oligosaccharide. In some embodiments the oligosaccharide is a glycan. FIG. 1 shows the basic core glycan structure, which is common to all N-linked glycans. The core glycan structure can be oxazoline, a tetrasaccharide. In some embodiments the innermost N-acetylglucoasmine of the basic core N-linked glycans can be modified with a fucose. FIG. 2 demonstrates an antibody conjugated incorporating a N-linked glycan with a core modified by fucose. It will be appreciated by one of ordinary skill in the art that N-linked glycans contain variable terminal structures. The glycan(s) that can be attached to the antibody as described herein can contain any such variable terminal structure. In some embodiments, the oligosaccharide is a N-linked glycan. In one embodiment, the N-linked glycan can be a decasaccharide. The oligosaccharide can be the oligosaccharide oxazoline.

Payload Molecules

The payload molecule can be attached to a member of a bioorthogonal reaction handle pair via a linker. In some embodiments, the payload molecule is attached to an antibody through a bioorthogonal reaction handle pair and linkers as described elsewhere herein and as demonstrated in FIGS. 1-2. The payload molecule can be any small molecule, DNA, RNA, amino acids, peptides, polypeptides, antibodies, aptamers, ribozymes, guide sequence for ribozymes that inhibit translation or transcription of essential tumor proteins and genes, hormone, immunomodulator, antipyretic, anxiolytic, antipsychotic, analgesic, antispasmodic, anti-inflammatory, anti-histamine, anti-infective, radiolabel, fluorophore, imaging agent, and chemotherapeutics.

Suitable hormones include, but are not limited to, aminoacid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and (β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, maytansine, monomethyl auristatin E, duocarmycin, calicheamicin, cemadotin, monomethyl auristatin F, and all-trans retinoic acid.

The payload molecule can also be a suitable label to allow for visualization, monitoring, or otherwise detecting the antibody conjugate. Suitable labels include, but are not limited to, isotopic labels, radiolabels, fluorescent labels, colorimetric labels, or biomaterial label.

Suitable isotopic labels include, but are not limited to, stable isotopes of carbon, nitrogen, hydrogen, and iodine. These stable isotopes can be incorporated into any molecule containing non-isotopic versions of these elements. For example, a nitrogen isotope can be incorporated into a polypeptide, thus making the polypeptide traceable. The polypeptide with the isotopic element can then be used as a payload molecule. Other compounds or molecules that incorporate a measureable isotopic element will be appreciated by those of skill in the art.

Suitable radiolabels include, but are not limited to, radioactive (unstable) isotopes of carbon (e.g. and $^{11}C$, $^{13}C$, and $^{14}C$), hydrogen (e.g. $^{3}H$), iodine (e.g. $^{124}I$ and $^{123}I$), fluorine ((e.g. $^{18}F$), oxygen (e.g. $^{15}O$ and $^{17}O$), bromine (e.g. $^{76}Br$), nitrogen (e.g. $^{13}N$ and $^{15}N$), sulfur (e.g. $^{33}S$) or other radiolabel. Like the suitable isotopic labels, the radioactive isotopes of elements can be incorporated into a compound or protein, which then can be used as the payload molecule.

Suitable fluorescent labels include, but are not limited to, isothiocyanate derivatives (e.g. fluorescein isothiocyanate, tetramethylrhodamine isothiocyanate, fluorescein, rhodamine, fluorescein derivatives (e.g. fluorescein isothiocyanate, NHS-fluorescein, carboxyfluorescein, carboxyfluorescein succinimidyl ester, 6-FAM phosphoramidite, 2',7'-difluorofluorescein, carboxyseminaphthofluorescein, and carboxynapthofluorescein), rhodamine derivatives (e.g. rhodamine 6G, rhodamine B, rhodamine 123, carboxytetramethylrhodamine, tetramethylrhodamine, tetramethylrhodamine isothiocyanate, sulforhodamine 101, NHS-rhodamine), maleimide activated fluorphores (e.g. fluorescein-5-maleimide), cyanines (e.g. Cy3 and Cy5).

Suitable colorimetric labels include, but are not limited to, para-Nitorphenylphosphate, coomassie Blue, 3,3',5,5'-tetramethylbenzidine, 3,3'-diaminobenzidine, 2,2'-azinobis [3-ethylbenzothiazoline-6-sulfonic acid], o-phenylenediamine dihydrochloride, combination of nitro blue tetrazolium chloride and 5-bromo-4-chloro-3-indolyl phosphate, p-Nitrophenyl phosphate.

Suitable biomaterial labels include, but are not limited to, horseradish peroxidase, alkaline phosphotase, biotin, avidin, glucose oxidase, beta-galactosidase, 3,3'-diaminobenzidine, horseradish peroxidase substrates (e.g. 3,3',5,5'-tetramethylbenzidine, 2,2'-azinobis [3-ethylbenzothiazoline-6-sulfonic acid], o-phenylenediamine dihydrochloride), alkaline phosphatase substrates (e.g. a combination of nitro blue tetrazolium chloride and 5-bromo-4-chloro-3-indolyl phosphate, p-nitrophenyl phosphate), glucose oxidase substrates (e.g. nitro blue tetrazolium chloride), beta-galactosidase substrates (e.g. 5-bromo-4-chloro-3-indoyl-β-D-galactopyranoside), chemiluminescent substrates (e.g. luminol), bioluminescent reactants (e.g. luciferin, aequorin, and luciferase).

Linkers

The antibody conjugate, oligosaccharaides, members of the bioorthogonal reaction handle pair, and/or payload molecules described herein can be attached to a linker. The linker can be any molecule that can be attached to the oligosaccharaides, members of the bioorthogonal reaction handle pair, and/or payload molecules described herein. The linkers described herein can reversibly attach to the oligosaccharaides, members of the bioorthogonal reaction handle pair, and/or payload molecules described herein. In other embodiments the linkers described herein can irreversibly attach to the oligosaccharaides, members of the bioorthogonal reaction handle pair, and/or payload molecules described herein. In further embodiments, the linker can be cleavable. In other embodiments, the linker can be uncleavable. It will be appreciated that the antibody conjugate, oligosaccharide(s), member(s) of the bioorthogonal reaction handle pair, and/or payload molecules can be attached to the linker at either end of the linker or any region between the ends of the linker.

Suitable linkers include, but are not limited to, amides, hydrazones, disulfides, thioethers, and peptides.

Bioothogonal Reaction Handle Pairs

Bioorthogonal reactions, as used herein, refers to chemical reactions that can take place in chemically complex environments or involving chemically complex molecules, such as those found in biologic systems or on biologic molecules, and provide the ability to control chemical reactivity and selectivity. The antibody conjugates described herein can include a bioorthogonal reaction handle pair that can provide selective attachment of a payload molecule to an oligosaccharide attached to an antibody.

The bioorthogonal reaction handle pair contains two (2) members (or bioorthogonal reaction handles), which can selectively react with one another. In some embodiments, the bioorthogonal reaction handles can irreversibly react with each other such that they are stably attached to one another. In other embodiments, the bioorthogonal reaction handles can reversibly react with each other. In some embodiments, the reaction between the bioorthogonal reaction handles can be reversed under reducing conditions. In other embodiments, the reaction between the bioorthogonal reaction handles can be reversed under acidic conditions.

Figure 5:
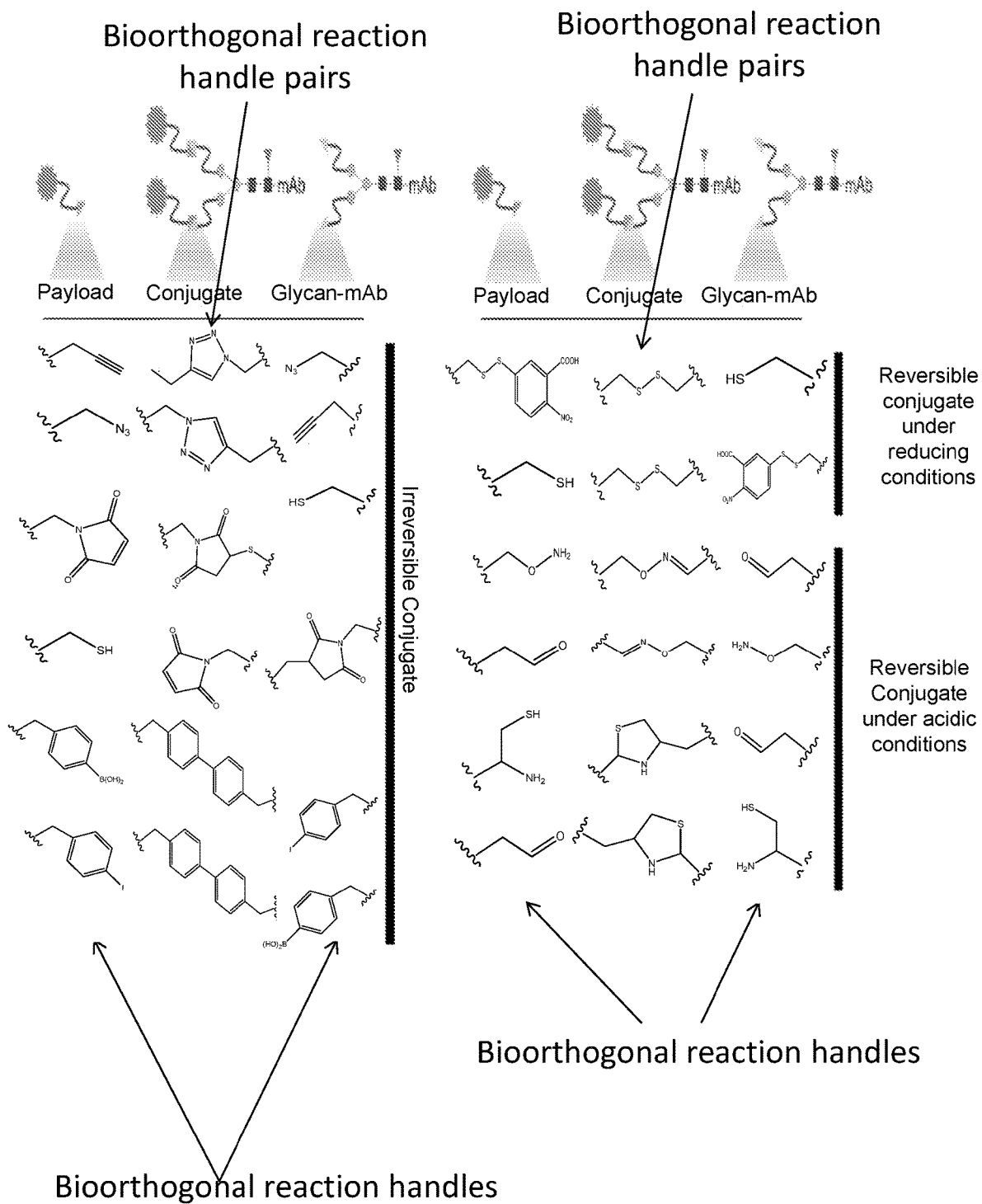
FIG. 5 shows several embodiments of the bioorthogonal reaction handles and bioorthogonal reaction handle pairs.

Suitable bioorthogonal reaction handles and the bioorthogonal reaction handle pairs they can form are shown in FIG. 5. Suitable bioorthogonal reaction handles also include, but are not limited to, strained alkynes, cyclopropenes, nitrile oxides, nitrile imines, and strained alkenes, norbornenes.

Pharmaceutical Formulations Containing the Antibody Conjugates

Provided herein are pharmaceutical formulations that can contain an amount of an antibody conjugate as described herein in a pharmaceutical carrier appropriate for administration to an individual in need thereof. The individual in need thereof can have or can be suspected of having a disease, disorder, syndrome, or symptom thereof. In some embodiments, the individual has cancer or symptom thereof. In some instances the cancer is a breast or ovarian cancer. In some embodiments, the breast cancer is HER2+ breast cancer. In other embodiments, the individual has an autoimmune disease, disorder, or symptom thereof. In some embodiments, the individual has an infectious disease, such as viral or bacterial infection. In further embodiments, the individual has an inflammatory disease, disorder, or symptom thereof. Formulations can be administered orally, intravenously, intramuscularly, intravaginally, intraperitoneally, rectally, perenterally, topically, intranasally, or subcutaneously.

Parenteral Formulations

The antibody conjugate can be formulated for parenteral delivery, such as injection or infusion, in the form of a solution or suspension. The formulation can be administered via any route, such as systemically via the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the antibody conjugate can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of antibody conjugate.

The formulation can be buffered to a pH of 3-8 for parenteral administration upon reconstitution. Suitable buffers include, but are not limited to, phosphate buffers, acetate buffers, and citrate buffers Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the antibody conjugate in the required amount in the appropriate solvent or dispersion medium with one or more of the excipients listed above, as required, followed by filtered sterilization. Dispersions can be prepared by incorporating a sterilized antibody conjugate into a sterile vehicle which contains the basic dispersion medium and the required other ingredients from those listed above. Sterile powders for the preparation of sterile injectable solutions can be prepared by vacuum-drying and freeze-drying techniques, which yields a powder of the antibody conjugate thereof plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more antibody conjugates. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol. In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes. Solutions, suspensions, or emulsions for parenteral administration can also contain one or more preservatives to prevent bacterial contamination of the preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for parenteral administration can also contain one or more excipients, such as dispersing agents, wetting agents, and suspending agents Topical Formulations The antibody conjugate can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the antibody conjugate can be administered as a liquid formulation, such as a solution or suspension, a semi-solid formulation, such as a lotion or ointment, or a solid formulation. In some embodiments, the antibody conjugate is formulated as liquids, including solutions and suspensions, such as eye drops, or as a semi-solid formulation, such as ointment or lotion for topical application to the skin, to the mucosa, to the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers can include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions can include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing an antibody conjugate are also described herein. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing an antibody conjugate are also described herein. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Also described herein are ointments containing an antibody conjugate as described herein and a suitable ointment base. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing an antibody conjugate as described herein, a gelling agent, and a liquid vehicle. Suitable gelling agents include, but are not limited to, modified celluloses, such as hydroxypropyl cellulose and hydroxyethyl cellulose; carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that include the antibody conjugate. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine. Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The antibody conjugate can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing an antibody conjugate are prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing an antibody conjugate can be prepared using one or more pharmaceutically acceptable excipients, including diluents, preservatives, binders, lubricants, disintegrators, swelling agents, fillers, stabilizers, and combinations thereof.

The formulation containing an antibody conjugate can be a delayed release dosage formulation. Delayed release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing an antibody conjugate as described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug or antibody conjugate decomposition reactions which include, by way of example, oxidative reactions. Suitable stabilizers include, but are not limited to, antioxidants, butylated hydroxytoluene (BHT); ascorbic acid, its salts and esters;

Vitamin E, tocopherol and its salts; sulfites such as sodium metabisulphite; cysteine and its derivatives; citric acid; propyl gallate, and butylated hydroxyanisole (BHA).

Additional Active Agents

In some embodiments, one or more additional active agents are included in the pharmaceutical formulation. Suitable additional active agents include, but are not limited to, antipyretics, immunomodulators, chemotherapeutics and analgesics.

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

METHODS OF MAKING THE ANTIBODY CONJUGATES

Figure 6:
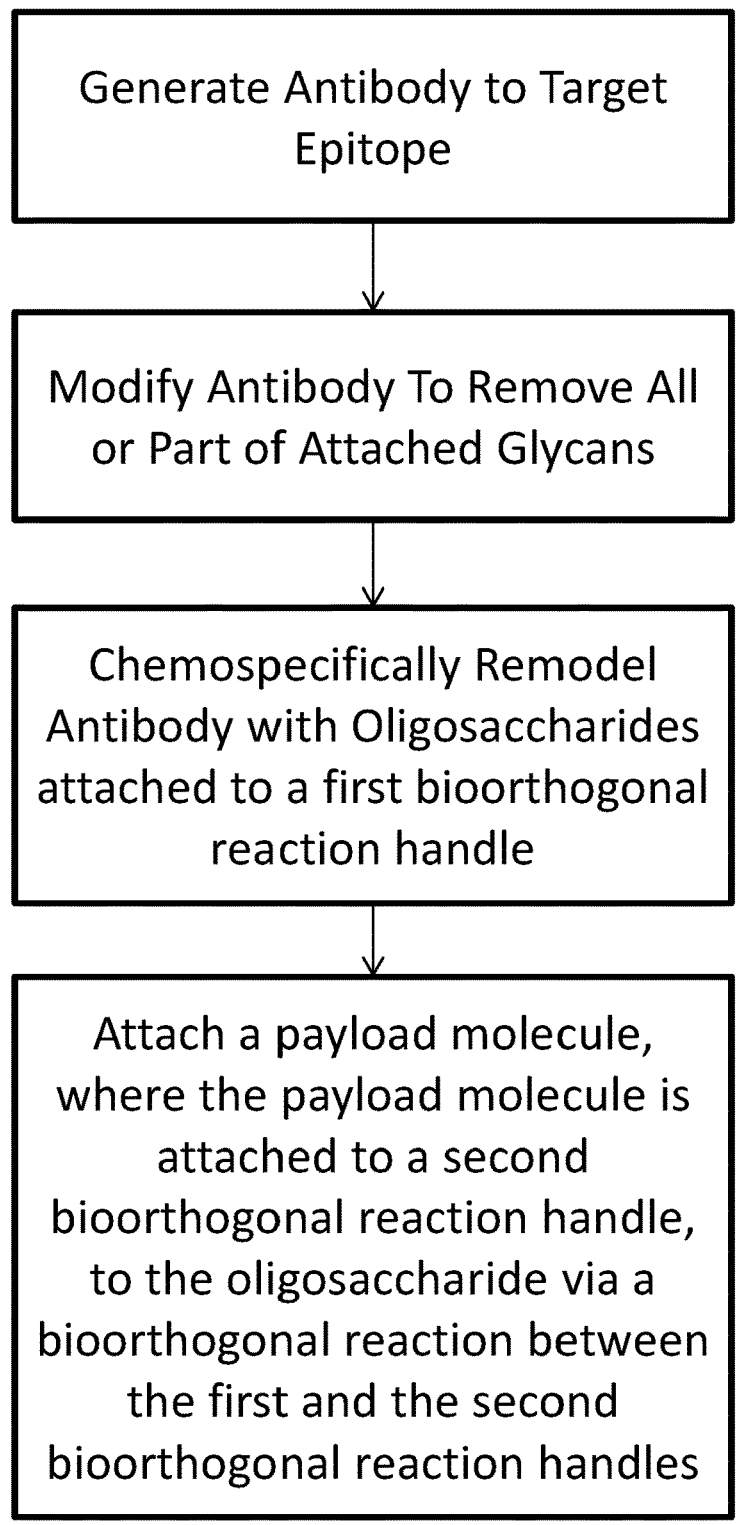
FIG. 6 generally shows one embodiment of a method of making the antibody conjugates described herein.

Provided herein are methods of making the antibody conjugates and modular components described herein. FIG. 6 generally shows one embodiment of a method of making the antibody conjugates described herein. To begin, antibodies that can specifically bind a target epitope can be generated, optionally optimized, and selected. Methods of making antibodies are described elsewhere herein. To produce a population of antibodies having a substantially homogenous glycoform, the antibodies are modified to remove all or part of the glycans attached to the antibodies. After the antibody has been modified, the antibody can be chemospecifically remodeled with oligosaccharides, where the oligosaccharides have an attached first bioorthogonal reaction handle. Finally, a payload molecule can be attached to the oligosaccharide via a bioorthogonal reaction. The payload molecule can be attached to a second bioorthogonal reaction handle. The first bioorthogonal reaction handle can react with the second bioorthogonal reaction to conjugate the two bioorthogonal reaction handles.

Oligosaccharide Scaffold Synthesis

Suitable oligosaccharides can be synthesized using methods generally known in the art. In some embodiments, the oligosaccharides can be glycans. The glycan scaffold, which includes a bioorthogonal reaction handle, can be semi-synthesized from chicken egg yolk. After collection of the egg yolks, lipids can be removed, glycopeptides can be extracted and precipitated. The peptide portion can be removed via protease digestion. Oligosaccharides can be obtained via gel filtration, such as via FPLC gel filtration. The oligosaccharides can be purified via a purification method such as HPLC. Oligosaccharides can be synthesized via protecting group manipulation and glycosylations (See e.g. schemes I-VI). Oligosaccharides can be synthesized to include at least one member of a bioorthogonal reaction handle pair. Synthesis of oligosacchradies with at least one member of a bioorthogonal reaction handle pair can include protecting group manipulation and glycosylations. In other embodiments, the oligosaccharides already contain at least one member of a bioorthogonal reaction handle pair without the need for further synthesis.

Oligosaccharide Functionalization

The semi-synthesized oligosaccharide scaffold, oligosaccharide, or other oligosaccharide scaffold can be functionalized. The oligosaccharide scaffold (semi-syntheszed or otherwise obtained) or oligosaccharide, can be a glycan. During functionalization, a bioorthogonal reaction handle can be attached to the oligosaccharide. The oligosaccharide can be modified during functionalization to an oligosaccharide oxazoline. Thus functionalization can produce a modified oligosaccharide or modified glycan.

Antibody Modification

Antibodies are produced in a variety of glycoforms. Any given population of antibodies raised against the same antigen produced may all bind the same target epitope but each antibody in a population may have a different native glycosylation profile, barring any other intervention to control glycosylation. In other words, the antibody population has a heterogeneous glycoform. It is well known that the particular glycoform can drastically affect the ability an antibody to bind with its target epitope or otherwise affect its efficacy. The antibody modification described herein can remove or trim the native oligosaccharides attached to the antibody after production, thus providing a clean slate to chemospecifically attach oligosaccharides so that a population of antibodies having a substantially homogeneous glycoform can be obtained.

In some embodiments, native glycans can be completely removed from the antibody using PNGase F, which is an amidase that can cleave glycans between the innermost GlcNAc and asparagine residues of high mannose, hybrid, and complex oligosaccharides from N-linked glycoproteins. PNGase F is commercially available. PNGase F can be used to remove oligosaccharides from the antibodies under denaturing or non-denaturing conditions. Protocols for removing oligosaccharides from N-linked glycoproteins are generally known in the art.

In other embodiments, native oligosaccharides can be trimmed from the antibodies using native EndoS or a mutant EndoS, including but not limited to, EndoS D233A, EndoS D233Q, EndoS D235E, and EndoS Y305F, which can trim oligosaccharides on glycoproteins such that only a single GlcNa residue remains. In some instances, the remaining GlcNAc is bound to a fucose in the 6-position. Methods of trimming N-linked glycoproteins using native EndoS are generally known in the art. Trimming of antibodies using EndoS D233A and D233Q was previously reported not to be possible.

Antibody Remodeling

After the antibody has been modified, oligosaccharides can be added to the antibody. The oligosaccharides can be added in chemospecific manner. In some embodiments, the oligosaccharides are chemospecifically added to the conserved asparagine 297 residues on the Fc portion of the antibody. In embodiments where the native oligosaccharides can be trimmed using native EndoS or EndoS D233A, oligosaccharides can be chemospecifically added to the remaining GlcNAc residue. The oligosaccharide can be any oligosaccharide or modified oligosaccharide including, but not limited to, a glycan or modified glycan as described herein. In other embodiments, the oligosaccharide substrate used in the EndoS catalyzed reaction can be a decasaccharide. In some embodiments, the decasaccharide is a decasaccharide oxazoline. In some embodiments, the oligosaccharide is activated during antibody remodeling. For example, oligosaccharide 9 of the decasaccharide oxazoline is activated.

Figure 15A:
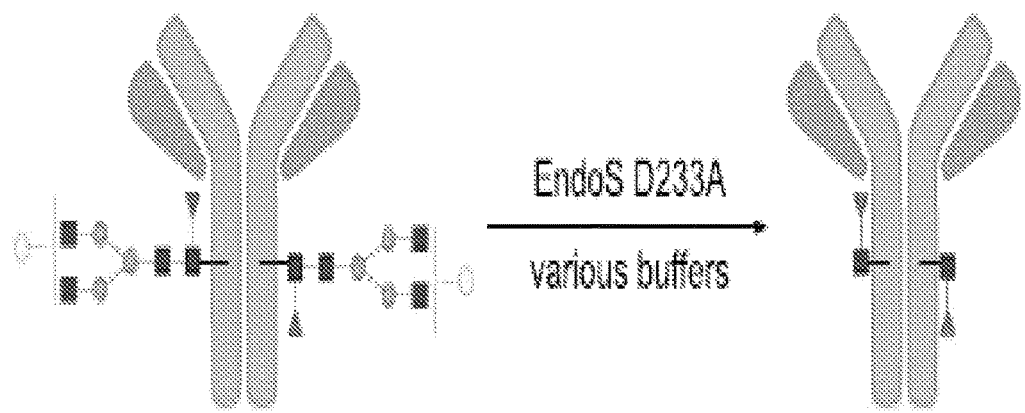
FIGS. 15A-15B demonstrate embodiments of a general reaction scheme for deglycosylation (FIG. 15A) and glycosylation (FIG. 15B) of an antibody with an EndoS mutant.
Figure 15B:
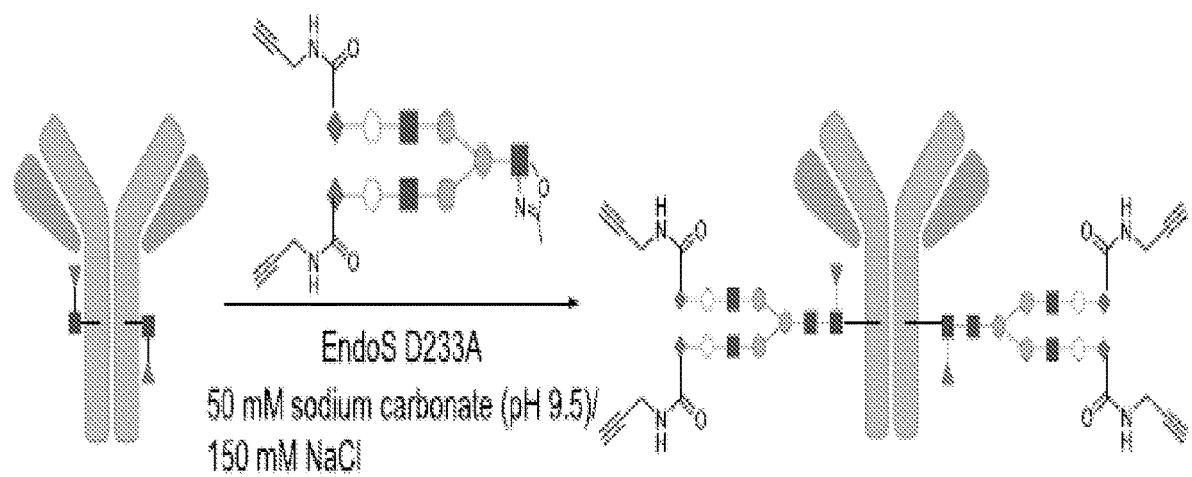

FIG. 15B demonstrates one embodiment of a reaction where an oxazoline donor is used in a glycosylation reaction. "Activated" as used herein refers to the instance where a donor is activated towards a glycosylation, i.e. a reaction with an acceptor (a nucleophile). One of ordinary skill in the art will appreciate that an oxazoline is a mimic of the transition state of the enzyme-catalyzed hydrolysis reaction and that this can be the primary source of activation. During this reaction the oxazoline can be opened by acting as a leaving group at the anomeric position.

In some embodiments, addition of the oligosaccharide to the modified antibody can be catalyzed by native EndoS a mutant EndoS, including but not limited to, EndoS D233A, EndoS D233Q, EndoS D235E, and EndoS Y305F. Prior to addition to the modified antibody, the oligosaccharide can be modified to an oligosaccharide oxazoline. In some embodiments, the oligosaccharide oxazoline is attached to the remaining GlcNAc residue via a reaction catalyzed by native EndoS or EndoS D233Q. In some embodiments, the reaction catalyzed by native EndoS or a mutant EndoS, including but not limited to, EndoS D233A, EndoS D233Q, EndoS D235E, and EndoS Y305F, is carried out in a suitable buffer. Suitable buffers can include, but are not limited to, phosphate buffered saline, sodium carbonate, sodium phosphate, Tris-HCl, or NaCl buffer. In some embodiments, the buffer can have a pH less than 7. In other embodiments, the buffer can have a pH greater than 7. In further embodiments, the buffer can have a pH of 7. The reaction can be carried out at a temperature ranging from about 4° C. to about 40° C. The reaction can be carried out for about 30 min to about 5 hours. The concentration of antibody used in the reaction can range from about 0.1 mg/mL to about 3.0 mg/mL.

Payload Molecule Preparation

A suitable linker can be attached to a payload molecule using methods generally known in the art. A suitable bioorthogonal reaction handle can be attached to the suitable linker or the payload molecule, using methods generally known in the art.

Bioorthogonal Conjugation

A payload molecule that is attached to a bioorthogonal reaction handle can be attached to an oligosaccharide on an antibody that is attached to a bioorthogonal reaction handle via bioorthogonal conjugation between the reaction handles under suitable reaction conditions. In some embodiments, the bioorthogonal reaction handle is attached to the oligosaccharide via an amidation reaction. In some embodiments, about 15-25 molar equivalents of a salt of an amine attached to a bioorthogonal reaction handle, 15 molar equivalents of DMTMM and a decasaccharide lactol diacid can be incubated for about 18 to about 72 hours at about 35° C. to about 50° C. One of ordinary skill in the art will appreciate that the exact conditions will vary depending on substrate.

In some embodiments, the payload molecule and the oligosaccharide can be bioorthogonally conjugated prior to attachment of the oligosaccharide to the antibody. In other embodiments, the payload molecule is bioorthogonally conjugated to the oligosaccharide after the oligosaccharide has been attached to the antibody.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Tetrasaccharide Assembly

A tetrasaccharide bearing a bioorthogonal reaction handle is an example of how a bioorthogonal handle may be introduced to the antibody using EndoS. As described above for the decasaccharide oxazoline, the tetrasaccharide may be reacted with the core GlcNAc remaining on the antibody in a reaction catalyzed by EndoS D233Q.

Tetrasaccharide GlcNAc Unit Preparation

Figure 7:
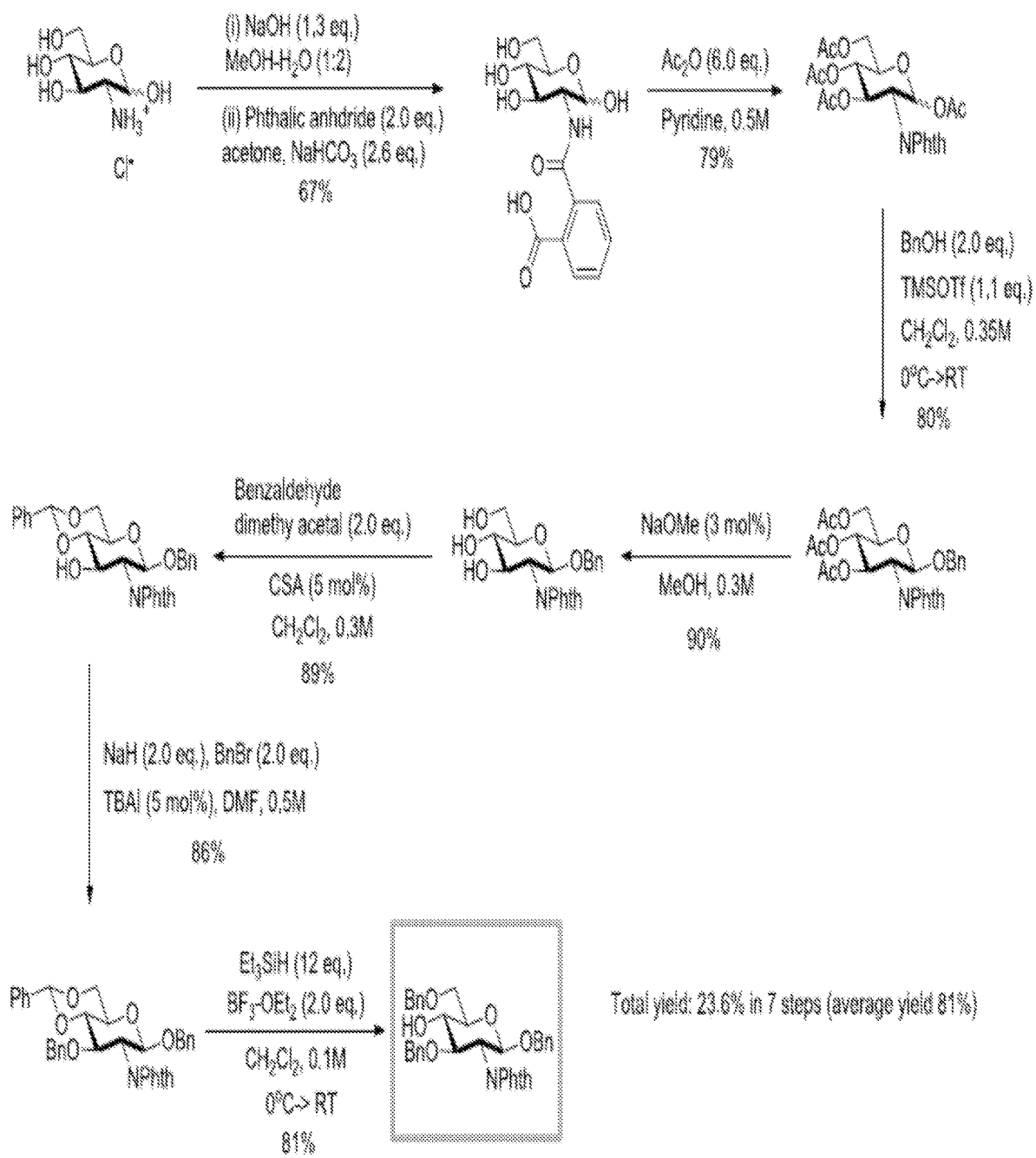
FIG. 7 demonstrates a tetrasaccharide GlcNAc unit prepared according to Scheme (1).

A tetrasaccharide GlcNAc unit was prepared according to Scheme (I), which is shown in FIG. 7.

Tetrasaccharide β-Man Unit Preparation

Figure 8:
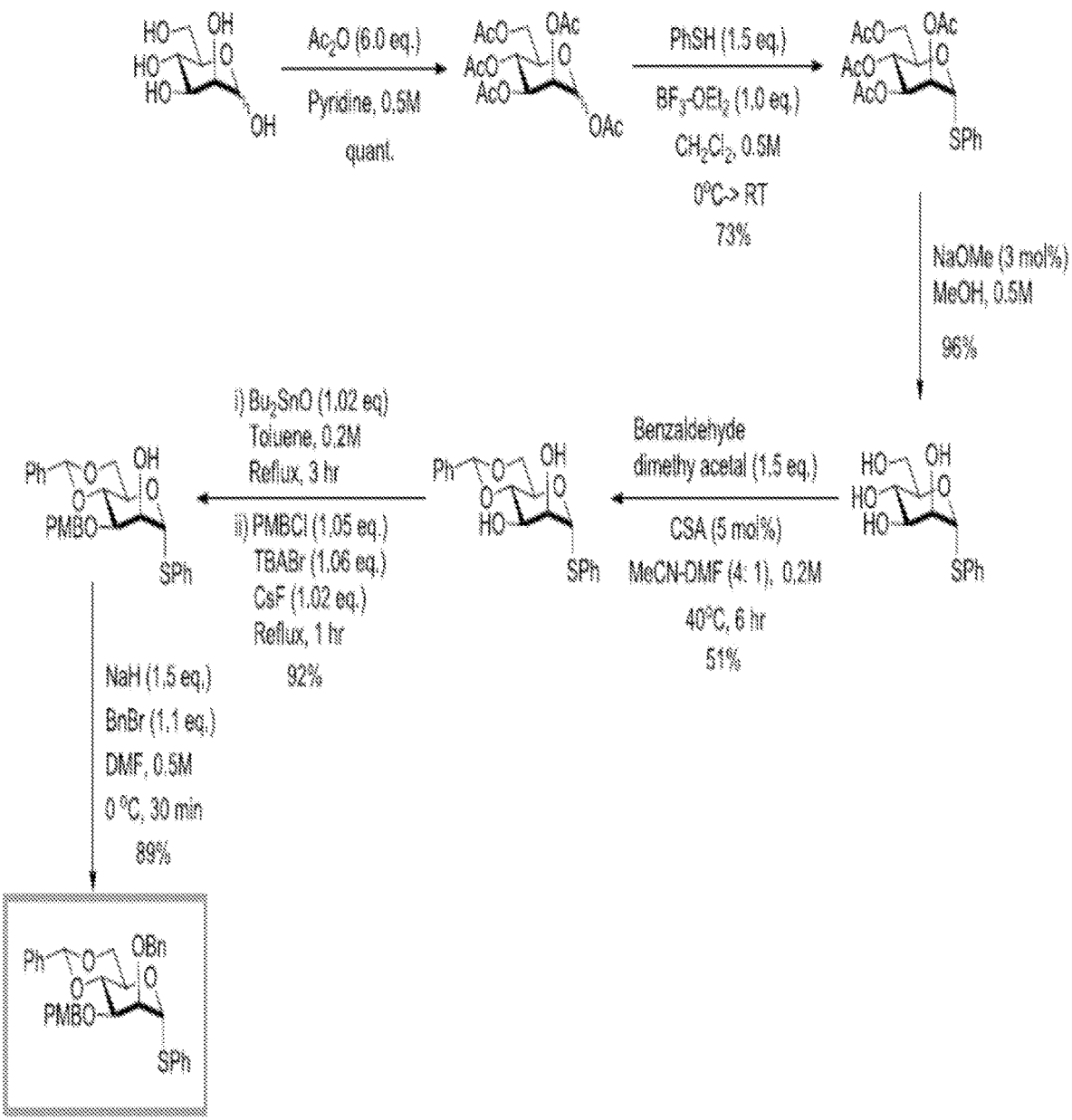
FIG. 8 demonstrates a tetrasaccharide β-Man unit prepared according to Scheme (II).

A tetrasaccharide β-Man unit was prepared according to Scheme (II), which is shown in FIG. 8.

Tetrasaccharide α-Man Unit Preparation

Figure 9:
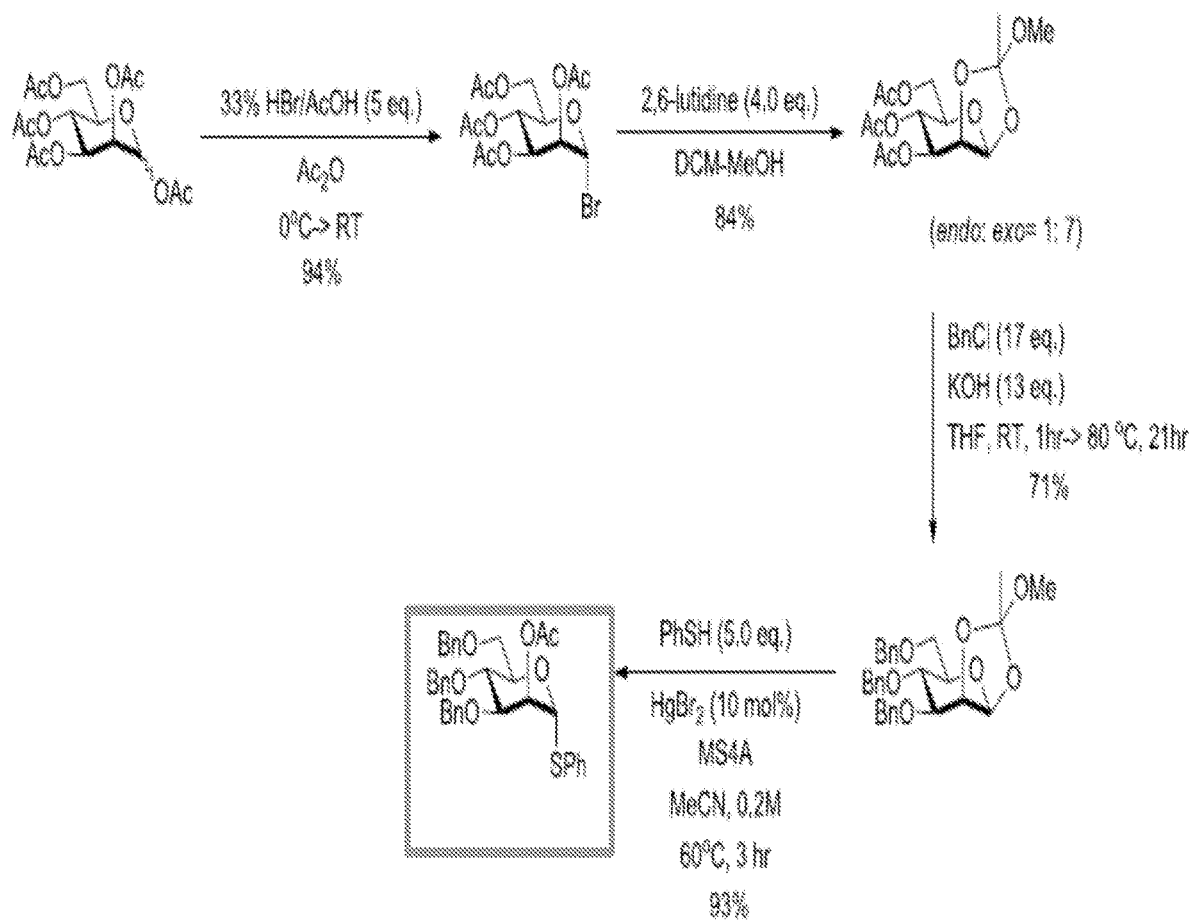
FIG. 9 demonstrates a tetrasaccharide α-Man unit prepared according to Scheme (III).

A tetrasaccharide α-Man unit was prepared according to Scheme (III), which is shown in FIG. 9.

Tetrasaccharide Assembly

Figure 10:
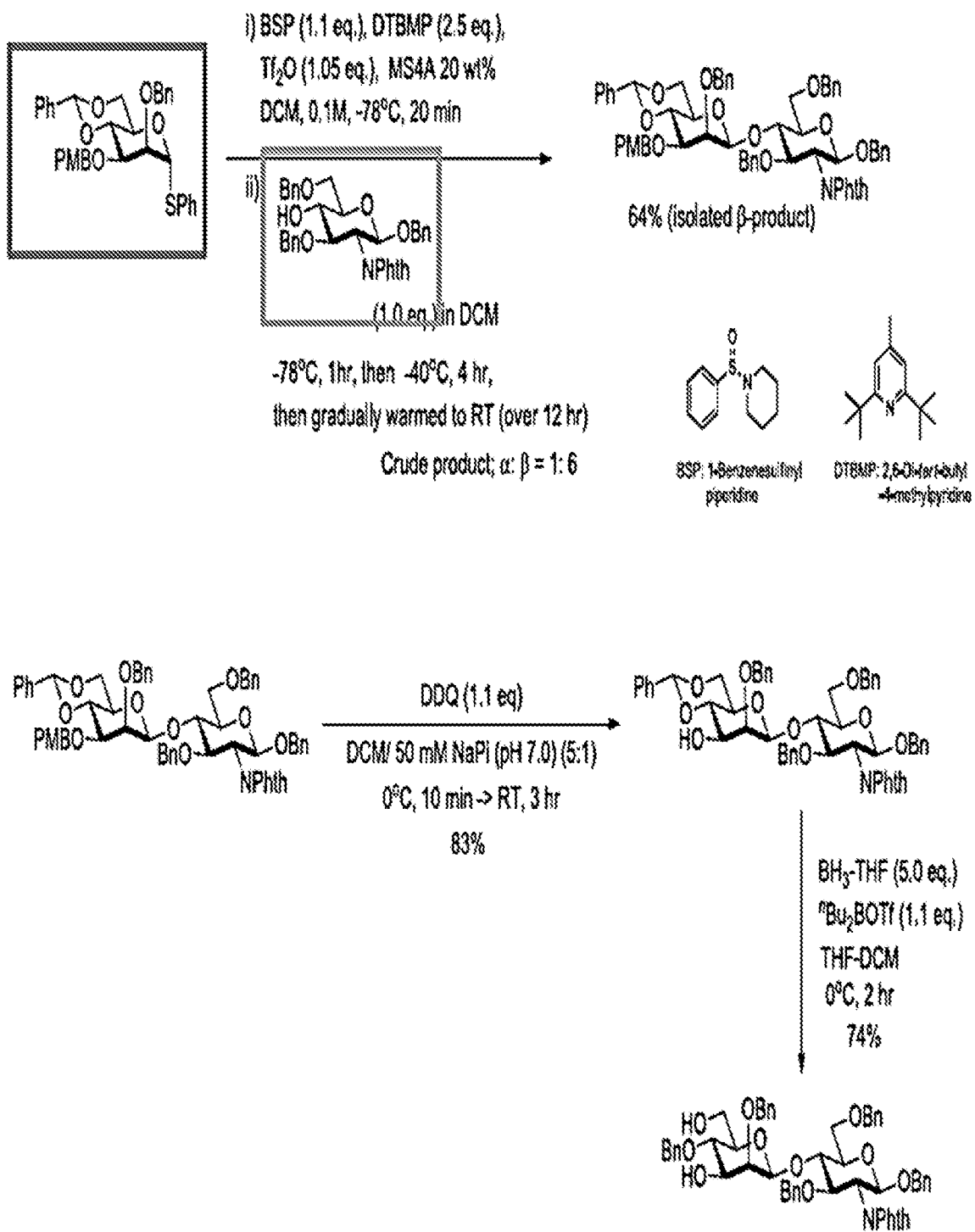
FIG. 10 demonstrates a tetrasaccharide assembly according to Scheme (IV).
Figure 11:
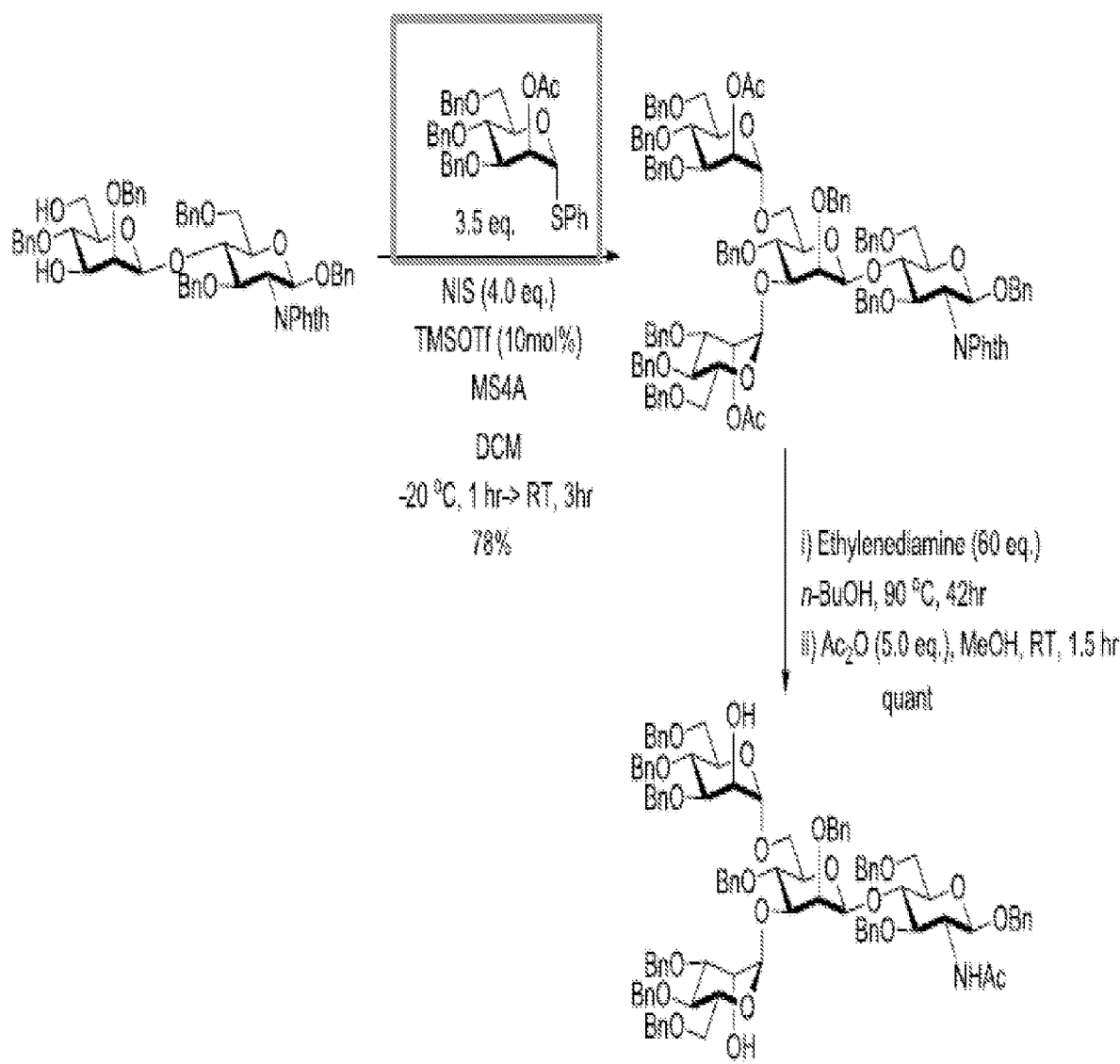
FIG. 11 demonstrates a tetrasaccharide assembly according to Scheme (V).

A tetrasaccharide was assembled from the tetrasaccharide units prepared according to Schemes (IV) and (V), which is shown in FIGS. 10 and 11.

Azide Addition to the Tetrasaccharide

Figure 12:
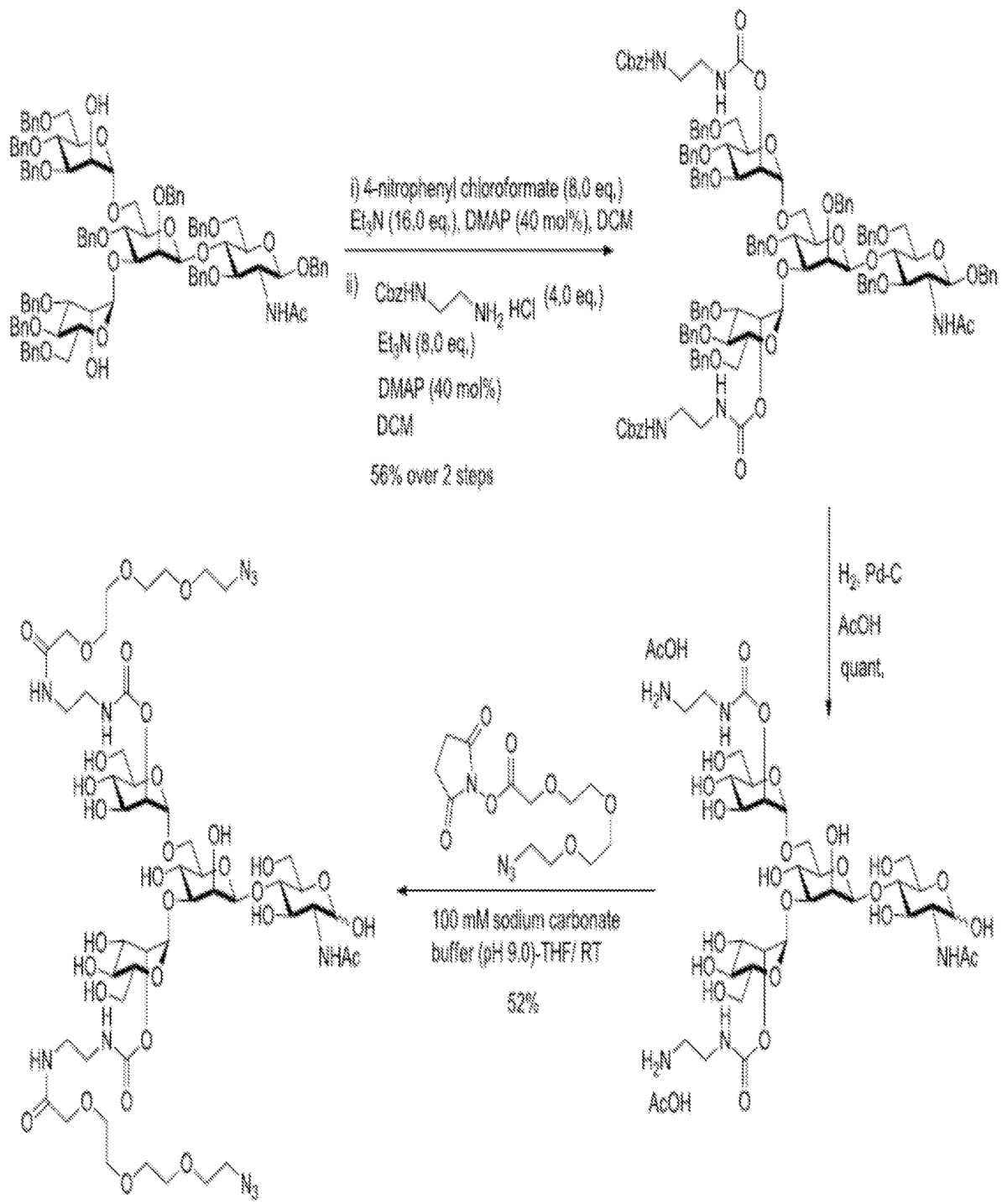
FIG. 12 demonstrates azide addition to a tetrasaccharide according to Scheme (VI).

An azide was added to the tetrasaccharide according to Scheme (VI) as shown in FIG. 12.

Example 2: Decasaccharide Semi-Synthesis from Egg Yolk

Figure 13:
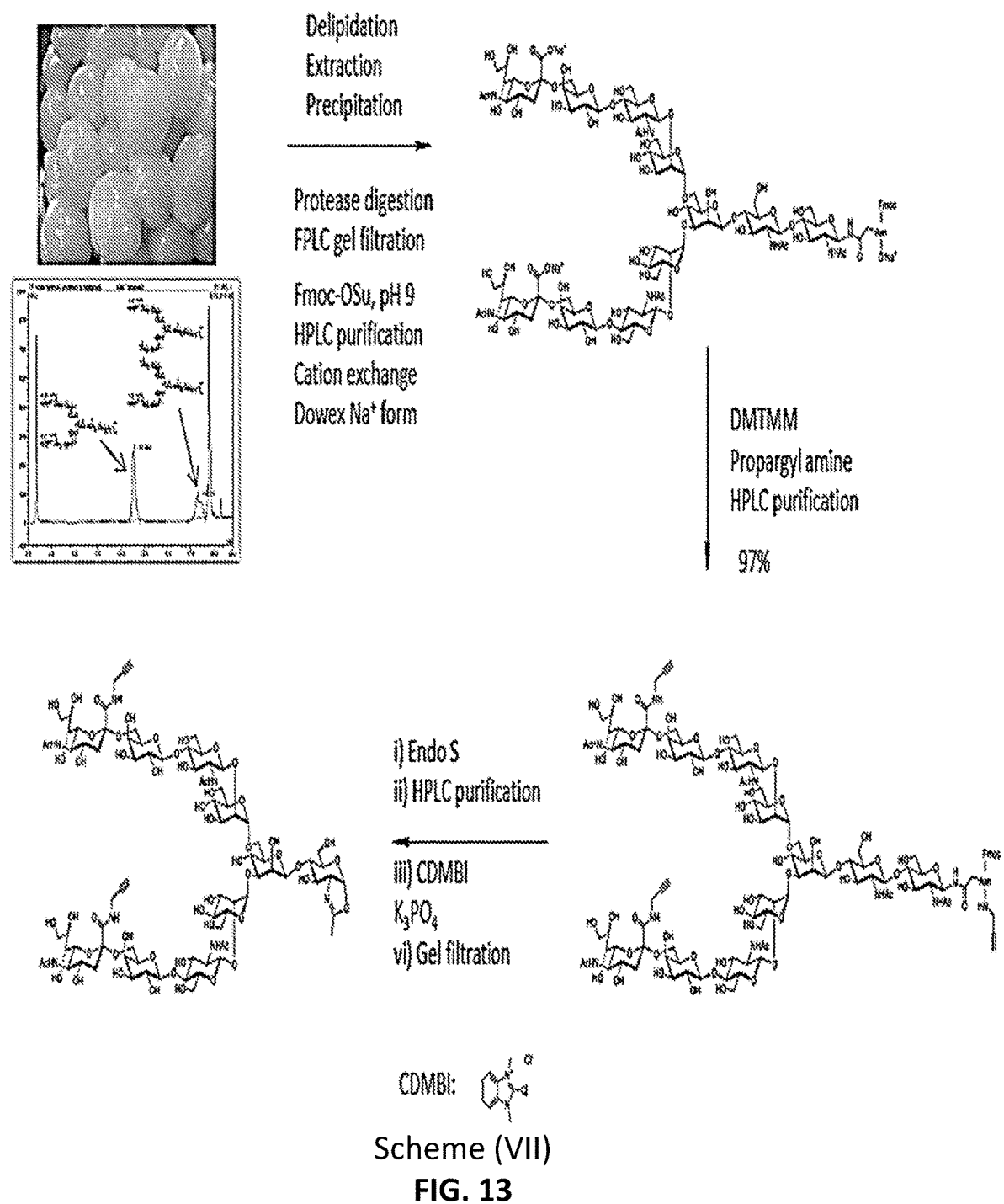
FIG. 13 demonstrates a method of semi-synthesis of a decasaccharide from egg yolk according to Scheme (VII).
Figure 23:
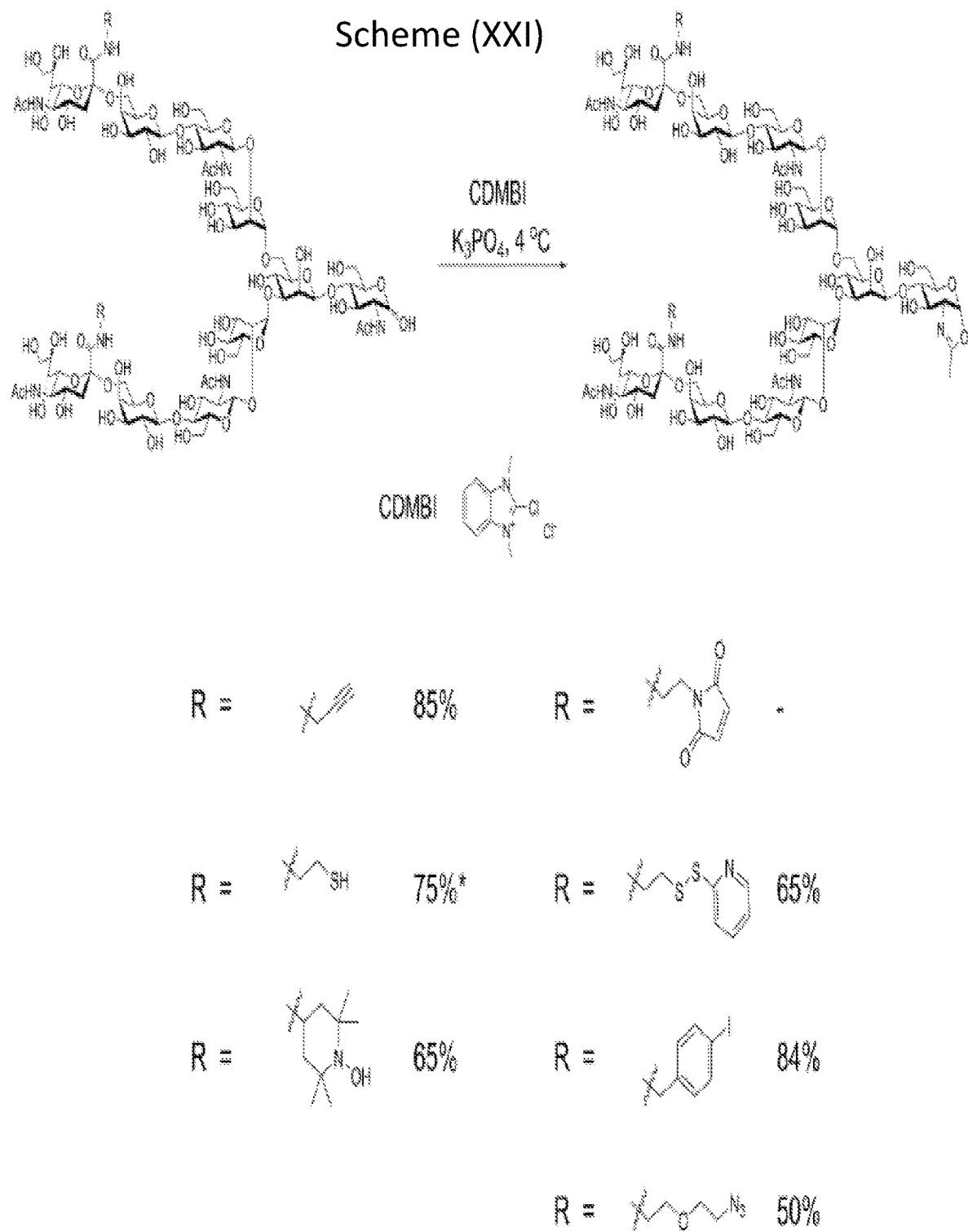
FIG. 23 demonstrates forming an oxazoline decaasaccharide using CDMBI according to Scheme (XXI).

A decasaccharide was semi-synthesized from egg yolk according to the method and Scheme (VII), which are shown in FIG. 13. Forming the oxazoline tetrasaccharide using CDMBI was as according to Scheme (XXI), which is shown in FIG. 23.

Figure 14A:
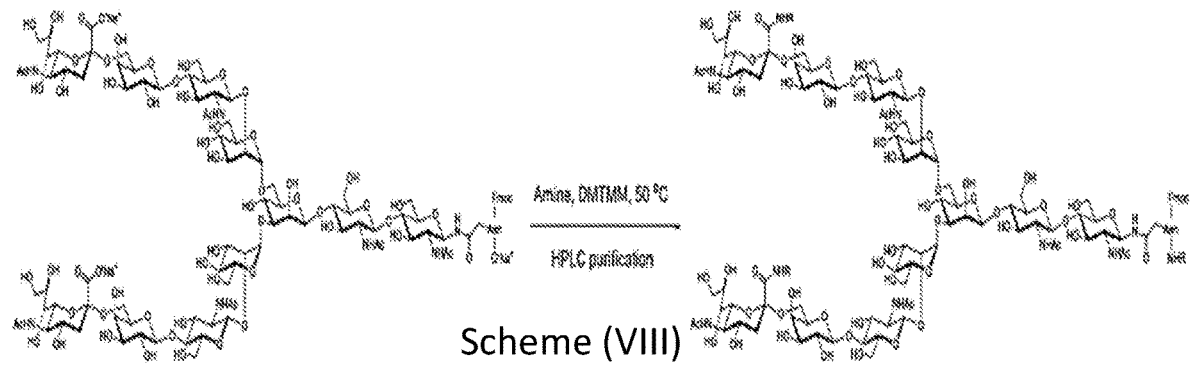
FIGS. 14A and 14B demonstrate various Schemes for addition of a bioorthogonal reaction handle to an oligosaccharide.
Figure 14A:
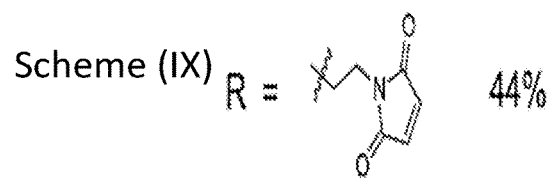
Figure 14A:
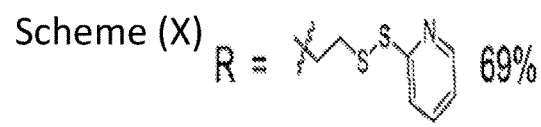
Figure 14A:
Figure 14A:
Figure 14B:
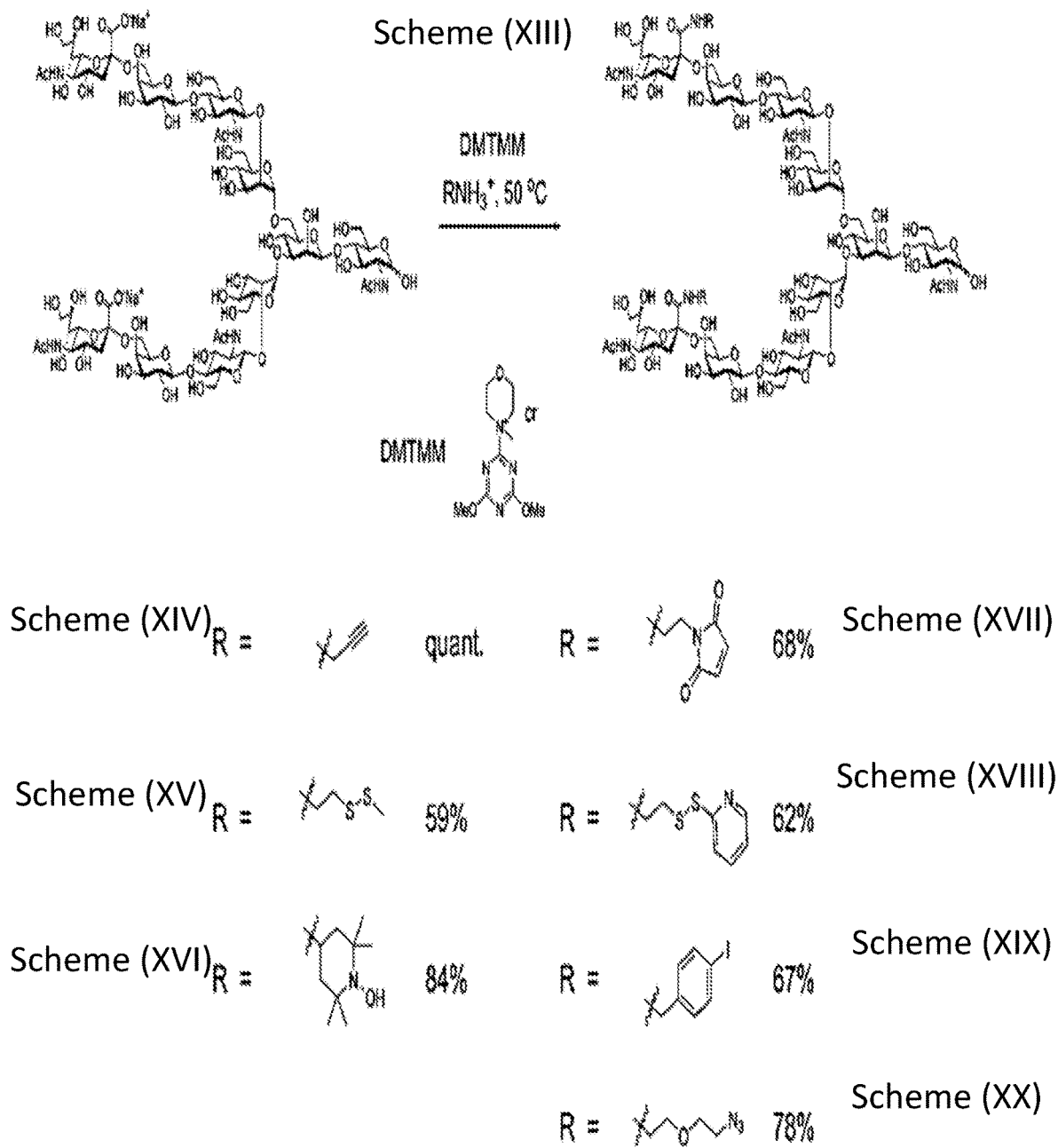

Example 3: Addition of a Bioorthogonal Reaction Handle to an Oligosaccharide Bioorthogonal reaction handle was added to deccasaccharides of Example 2 according to Schemes (VIII) through (XX), which are shown in FIGS. 14A and 14B. Here, the bioorthogonal reaction handle was added to the oligosaccharide via an amidation reaction. Briefly, about 20 molar equivalents of the salt (HCl or Trifluoroacetic acid) of the amine attached to the bioorthogonal reaction handle, about 15 molar equivalents of DMTMM (Sigma), and the decasaccharide lactol diacid was incubated together at about 35° C. to about 50° C. for about 18-72 hours. The exact incubation temperature and time varied depending on substrate.

Example 4: Cemadotin with a Cleavable Dipeptide Linker

Cemadotin was prepared with a cleavable dipeptide linker, as shown in Formula 1 below.

Figure 16:
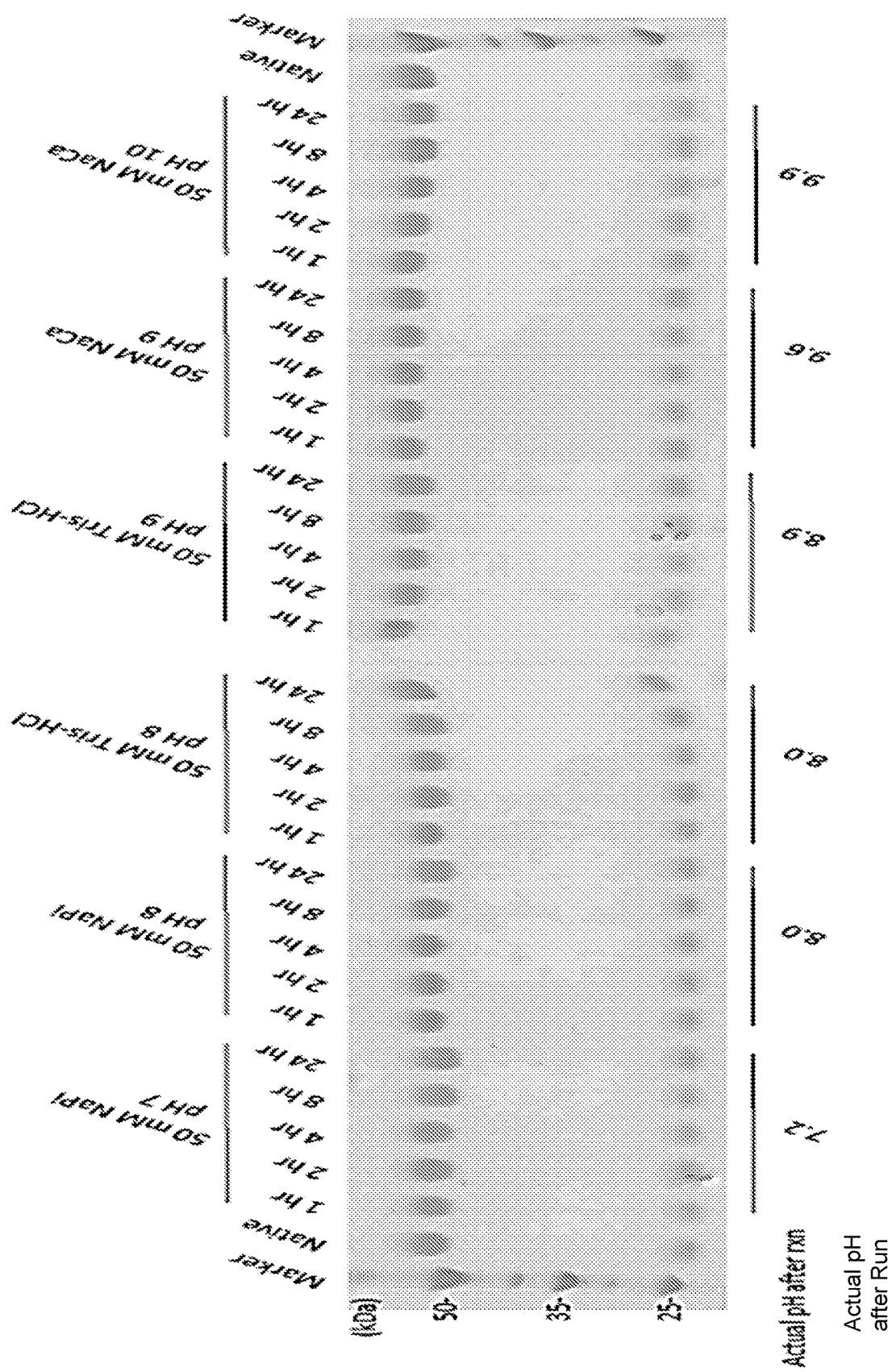
FIG. 16 demonstrates the results from glycosylation of a modified antibody according to the reaction Scheme of FIG. 15A.
Figure 17:
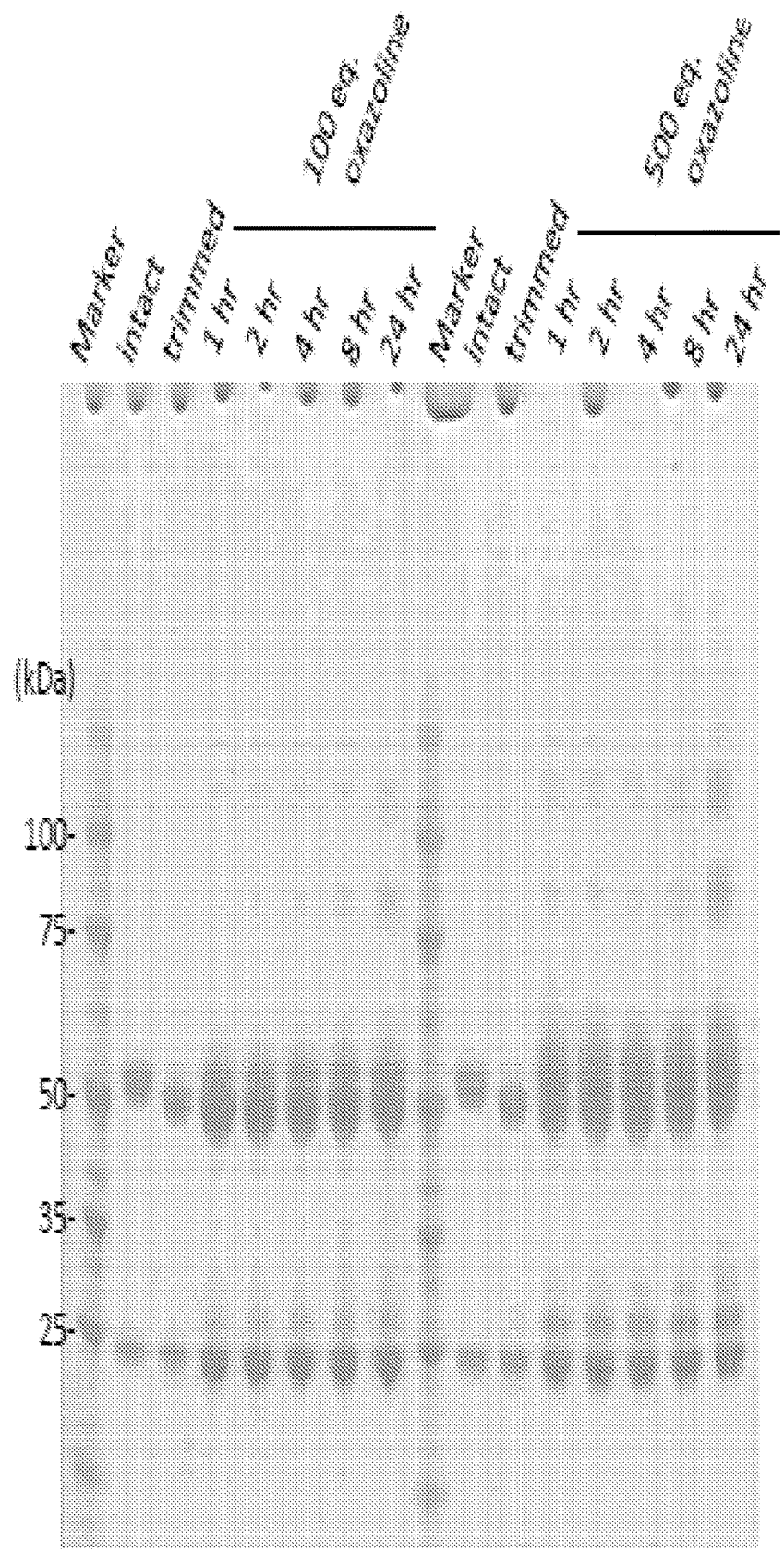
FIG. 17 demonstrates the results from glycosylation of a modified antibody according to the reaction Scheme of FIG. 15B.

Example 5: Antibody Glycoform Modification and Remodeling Using Mutant EndoS Glycans attached to antibodies were trimmed in a reaction catalyzed by EndoS in the presence of various buffers. Between about 50 μg and about 20 mg of antibody was treated with EndoS in a ratio between about 1:10 and about 1:500 EndoS:antibody. Reaction was conducted at temperatures between 20° C. and 40° C. for between 4 and 24 hours. The trimmed antibodies (human IgG, Sigma) were then remodeled via glycosylation with an oxazoline oligosaccharide. The general reaction scheme is shown in FIGS. 15A and 15B. Results are shown in FIGS. 16 and 17. During glycosylation, hydrolysis of the remodeled product and of the oxazoline starting material was reduced when the pH of the buffer was greater. Some non-specific glycosylation was observed at basic pHs. Non-specific glycosylation was observed during remodeling at higher pHs. Therefore, the optimal pH identified for the glycosylation reaction was about 6.5. In some instances, glycosylation of the light chain was observed. This may have been due to activation of lysine residues. Therefore, although the reaction can be carried out at any pH, the optimal pH identified for the glycosylation reaction was about 6.5.

Example 6: Deglycosylation and Remodeling of an Antibody

Deglycosylation

Figure 18:
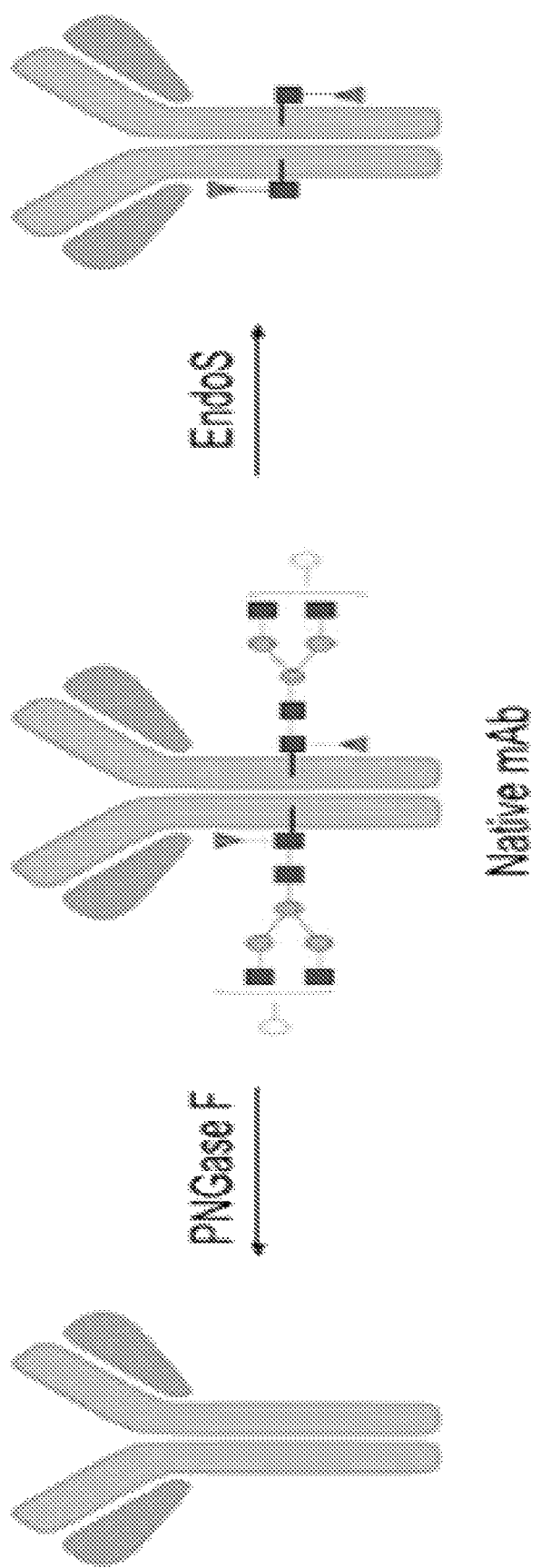
FIG. 18 demonstrates the general reaction scheme for modifying an antibody to alter the glycosylation of the antibody using PNGase F or EndoS (or an EndoS mutant).

Herceptin, an antibody, was deglycosylated completely using PNGase F or trimmed using native Endo S. The general scheme is shown in FIG. 18. Between about 20 μg and about 200 μg of antibody was treated with PNGase F in a ratio between about 1:10 and about 1:500 PNGase F:antibody. Reaction was conducted at 37° C. for between 8 and 24 hours. MALDI-ToF mass spectrometry was used to determine the glycoforms produced. The major glycoforms observed were G1F and G0F. The antibody was analyzed by electrospray ionization (ESI). Prior to ESI analysis, antibody samples were reduced (DTT, 60° C., 3 min).

Remodeling

The trimmed herceptin was remodeled using EndoS D233Q. The reaction was carried out at a pH of about 6.5 and at a temperature of about 30° C. Between about 20 μg and about 1 mg of antibody was treated with oligosaccharide oxazoline and with EndoS D233Q. Between 100 and 500 molar equivalents of oxazoline were used; optimal conditions vary but typical conditions were 70 molar equivalents Formula (1)

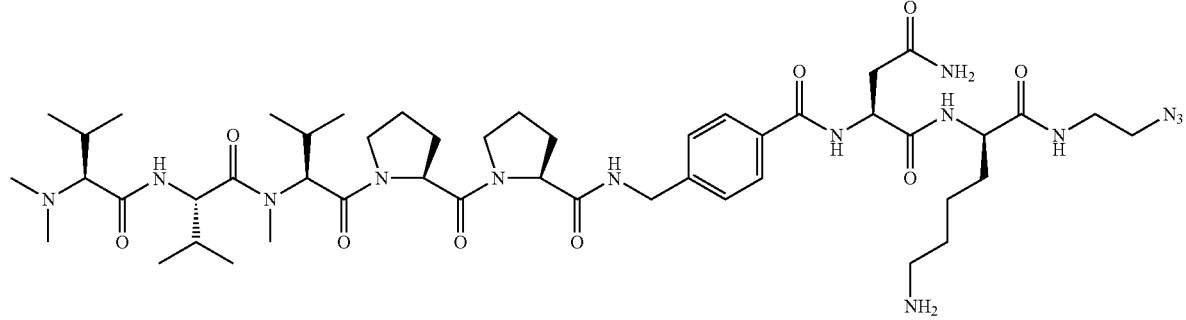

of oxazoline added at the start of the reaction and a further 70 equivalents added after between 40 minutes and one hour reaction time. Between 1:5 and 1:100 EndoS D233Q:antibody was used (weight:weight; the optimal amount of EndoS D233Q was around 1:20). Reaction was conducted at 30° C. for between 2 and 5 hours. About 30 minutes after the addition of the second aliquot of oxazoline, ESI analysis indicates about 55% glycosylation. After about 90 minutes about 80% conversion was observed and after about 3 hours complete conversion was observed. No double glycosylation of the heavy chain was observed. No glycosylation of the light chain was observed.

Figure 19:
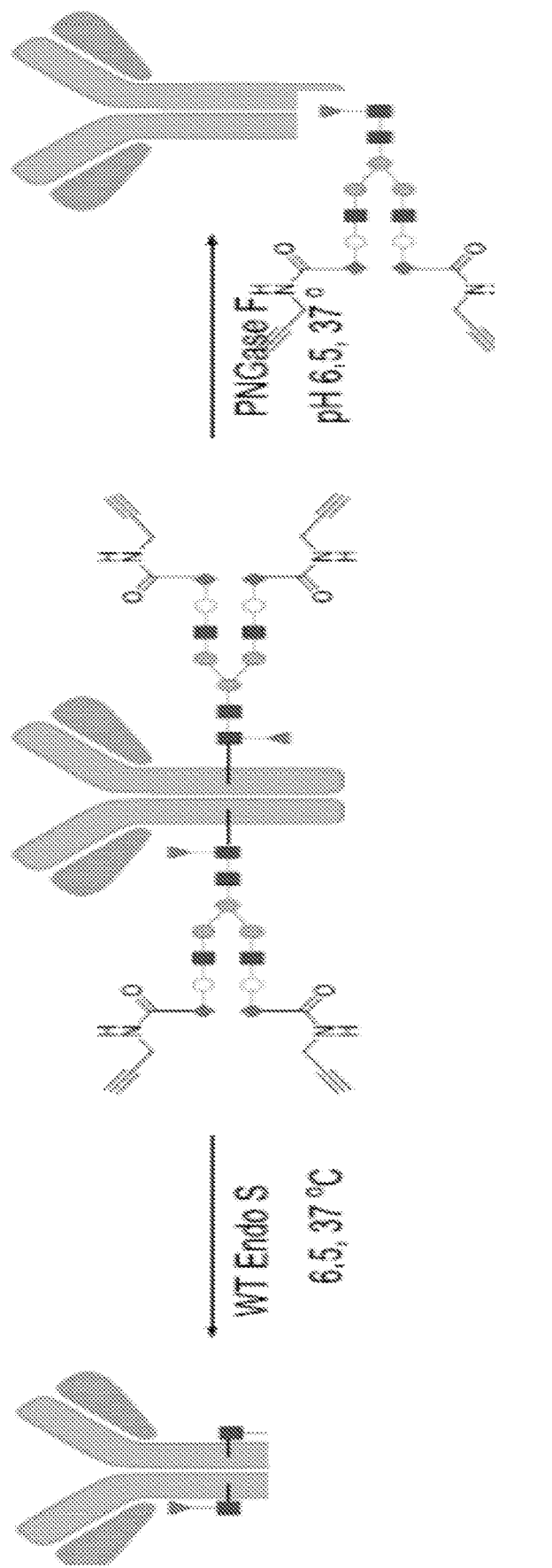
FIG. 19 demonstrates the general scheme for confirming selectivity of glycosylation by EndoS D233Q.
Figure 20A:
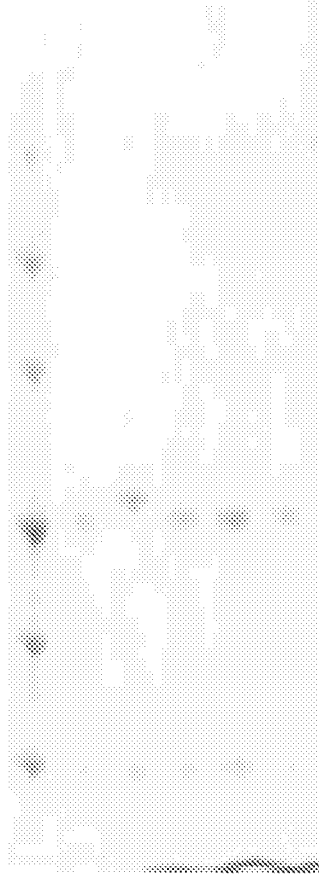
FIGS. 20A and 20B demonstrate the gel electrophoresis (FIG. 20A) and MALDI-ToF mass spectrometry (FIG. 20B) results confirming selectivity of glycosylation by EndoS D233Q.
Figure 20B:
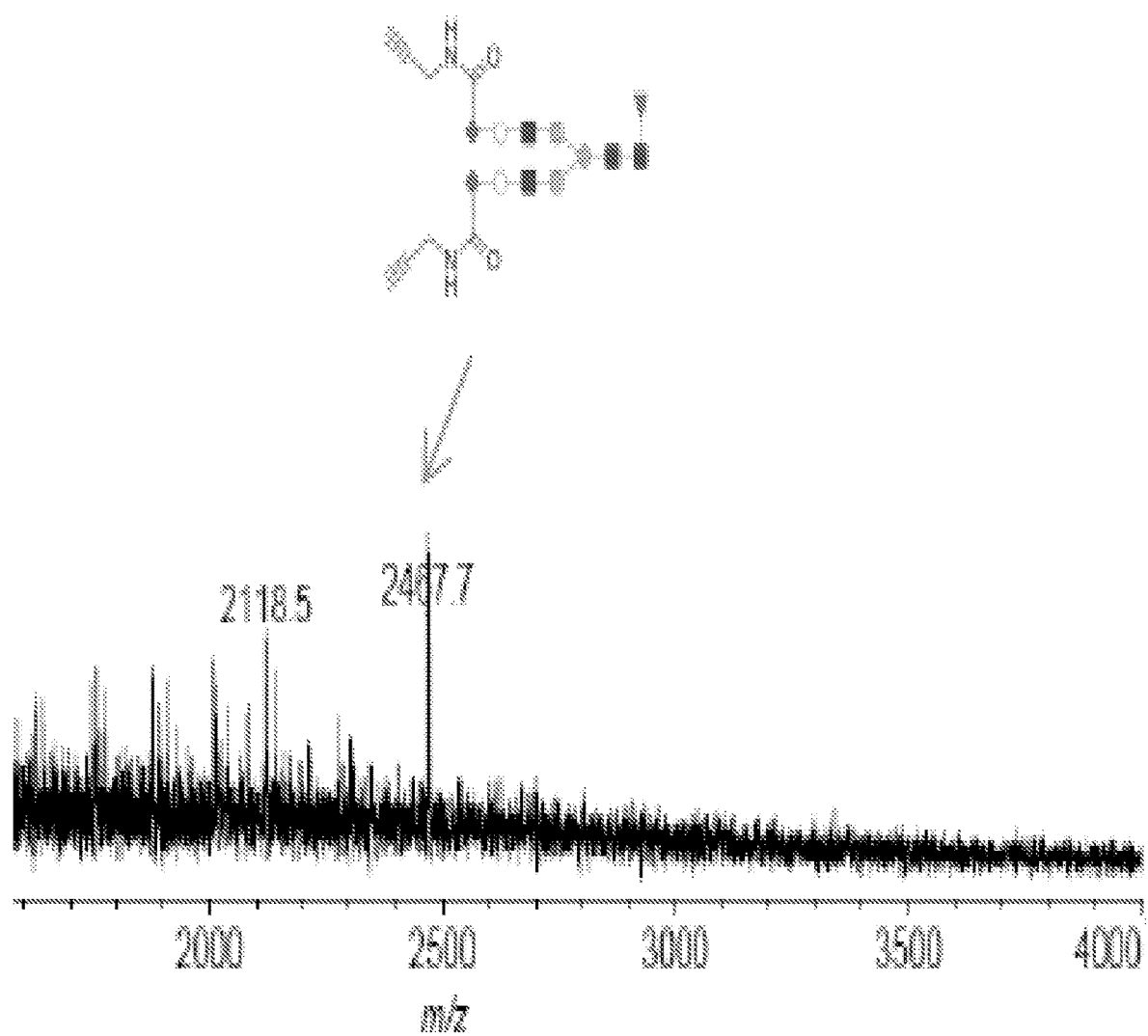
Figure 21A:
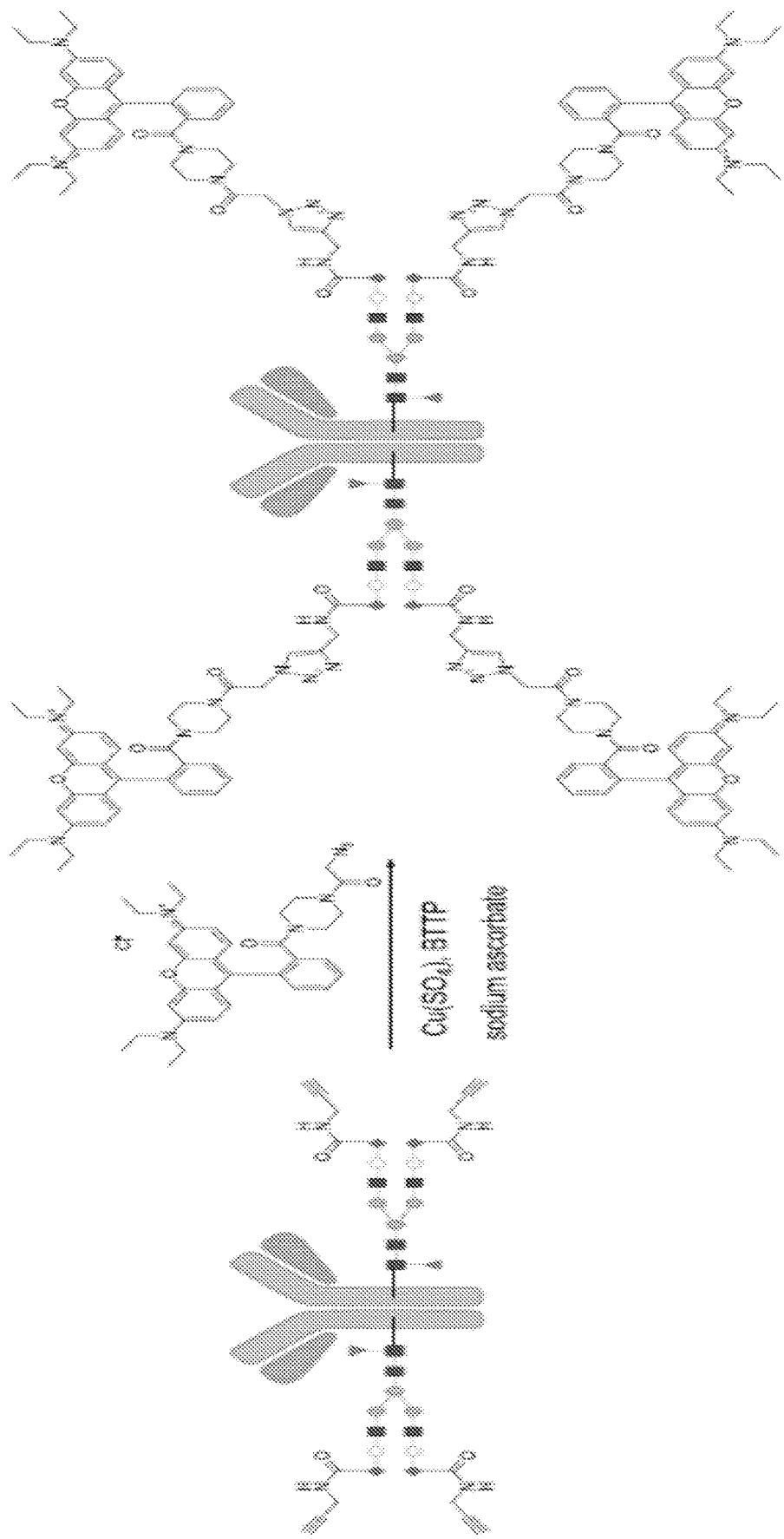
FIGS. 21A-21D demonstrate attachment of a payload molecule to a modified antibody.
Figures 21B, 21C, 21D:
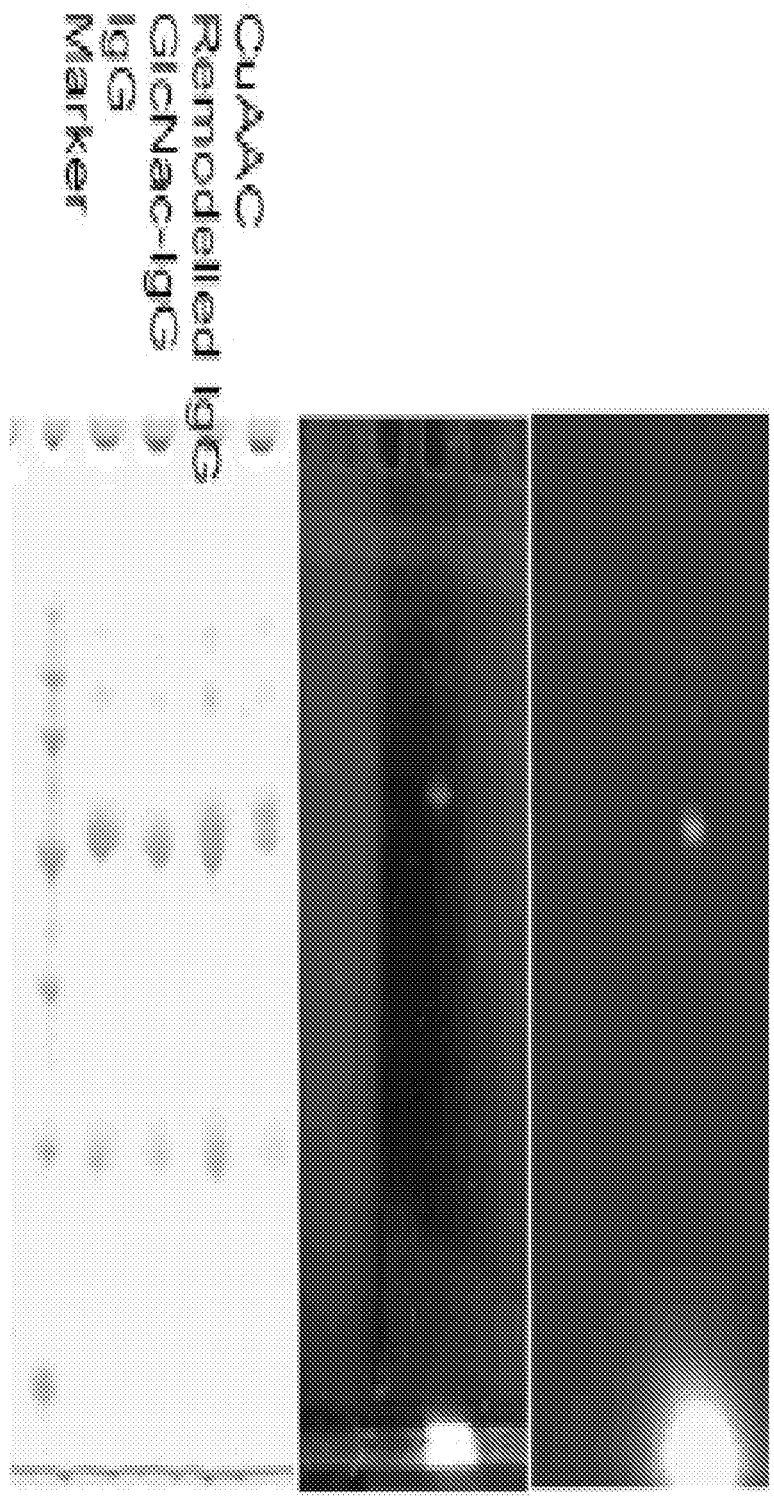

Selectivity of glycosylation was confirmed by deglycosylation using PNGase F and native EndoS deglycosylation followed by ESI and gel electrophoretic analysis. The general scheme is shown in FIG. 19. EndoS trimming was conducted at a pH of about 6.5 at about 37° C. for around 4 hours. PNGase F deglycosylation was performed at a pH of about 6.5 at about 37° C. for between about 16 and about 24 hours. The results are shown in FIGS. 20A and 20B.

Figure 25:
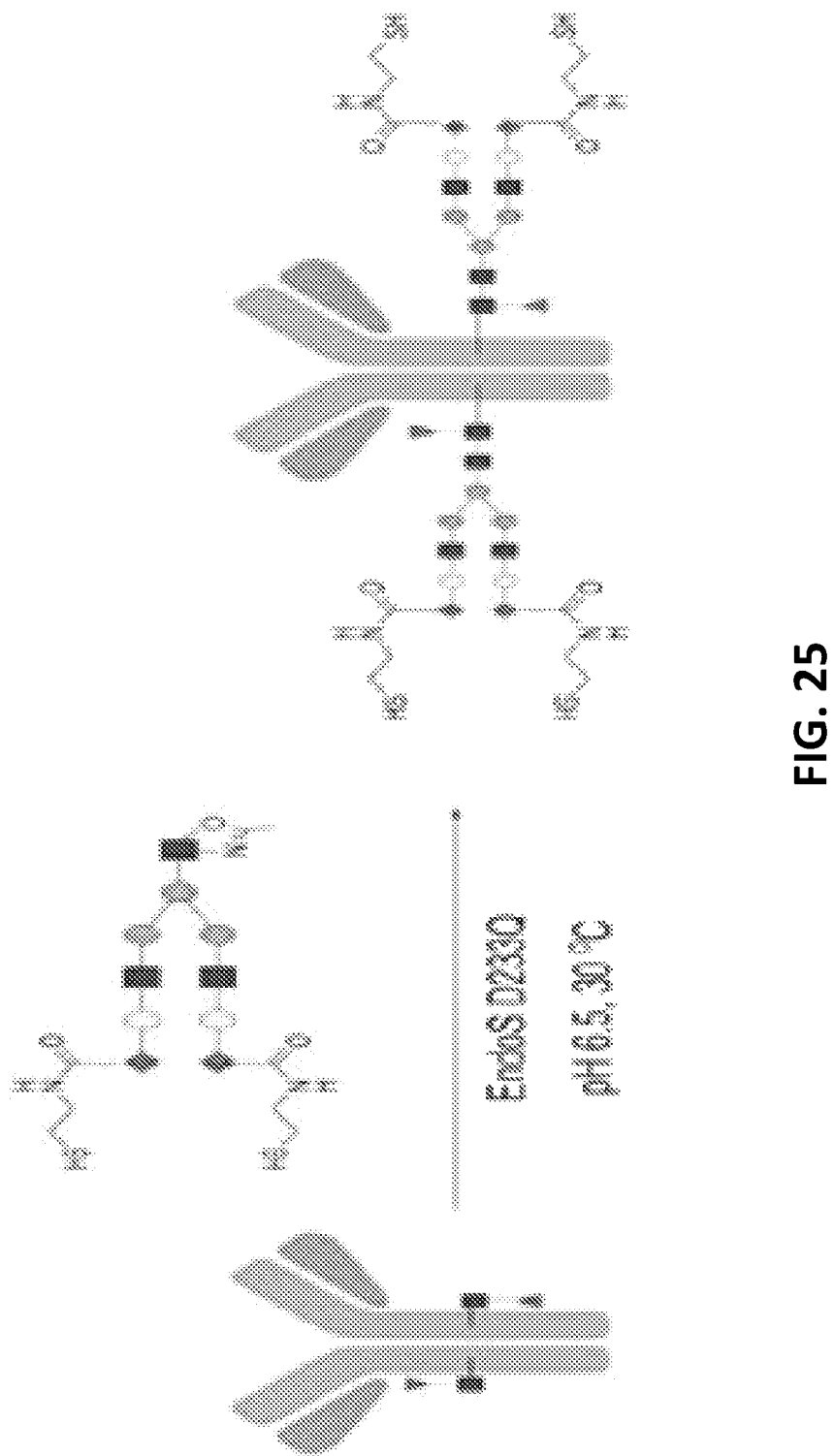

Remodeling of a trimmed antibody with different oxazoline oligosaccharides was also conducted and analyzed by ESI. Remodeling with was conducted using EndoS D233Q at a pH of about 6.5 at a temperature of about 30° C. for between about 2 and about 5 hours as described above. In some cases the oligosaccharide oxazoline was added in 3 portions. The general scheme is shown in FIG. 25.

Example 7: Attachment of a Payload to a Modified and Remodeled Antibody

Figures 22A, 22B:
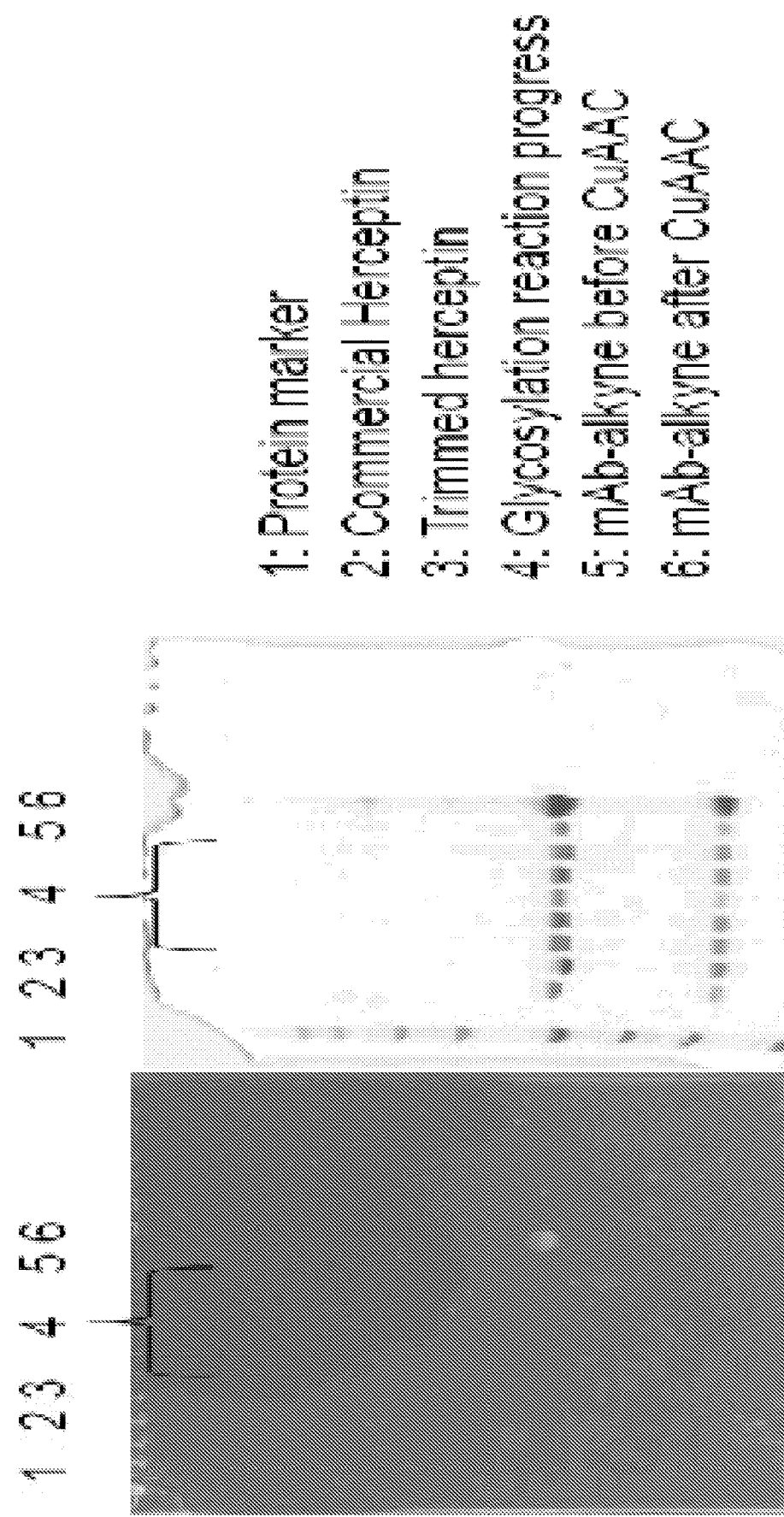
FIGS. 22A-22B demonstrate attachment of a payload molecule to a modified antibody.

A payload molecule was attached to the modified antibody remodeled with an oxazoline glycan of Example 6. The general schemes and the corresponding results are shown in FIGS. 21A-D; FIGS. 22A-B (Rhodamine azide: Fluorescent label—4%MeCN, 400 eq. Dye, 30 eq. CuBr, 60 eq. BTTP); FIGS. 26A-B (Fluorescein boronate: fluorescent label—PdL2, 20 mM phosphonate, pH 8.0, 37+C, 200 eq. Pd, 1000 eq. Dye); FIGS. 27A-D (biotin azide: biological label/tage—CuBr, Bttp, 400 eq. Biotin, 30 eq. CuBr 60 eq. BTTP); FIGS. 28A-D (Biotin alkyne: biological label/tag—CuBr, BTTP, 4& MeCN, 400 eq. Biotin, 30 eq. CuBr, 60 eq. BTTP).

Figure 24:
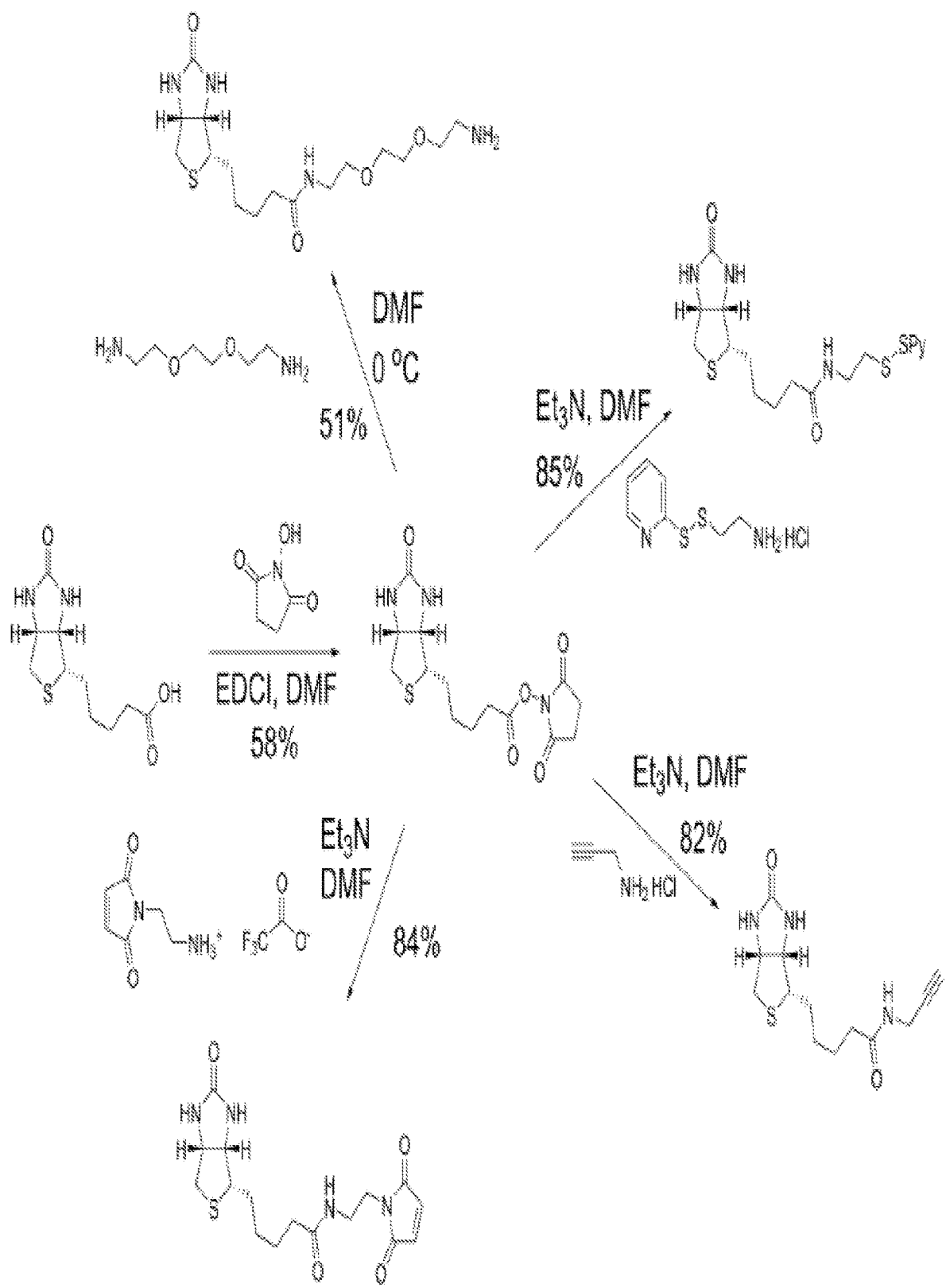
FIG. 24 demonstrates various reactions for attaching a bioorthogonal reaction handle to biotin.

Example 8: Addition of Bioorthogonal Reaction Handles to Biotin, a Payload Molecule Biotin was modified to contain a bioorthogonal reaction handle. Biotin was modified according to the reactions shown in FIG. 24.

Example 9: Analytical Size Exclusion

Samples were analyzed using an S200 10-300 size exclusion column (GE Healthcare) attached to an FPLC instrument. Eluent was analyzed by UV absorbance at 280 nm (blue line) and 220 nm (red line). Top left chart shows a calibration run using proteins of known molecular weights. Chart shows tabulation of log(MVV) v Kw (Kw=[observed elution volume minus column void volume] divided by [column volume minus column void volume]. Top right shows the graph of this data.

The size exclusion runs show Herceptin (single peaks with no asymmetry indicate no dimers or higher aggregates forming), another antibody, trimmed Herceptin (slight asymmetry with hump on left of main peak indicates some aggregation may be occurring), Herceptin remodeled with decasaccharide which has an alkyne attached, Herceptin remodeled with decasaccharide which has an azide attached and finally the product obtained after bioorthogonal reaction between antibody which has alkynes attached and biotin with an azide attached The data demonstrates that only very slight aggregation occurs during the various steps of antibody modification.

It should be emphasized that the above-described embodiments and Examples are merely examples of possible implementations. Many variations and modifications may be made to the above-described embodiments without departing from the principles of the present disclosure. All such modifications and variations are intended to be included herein within the scope of this disclosure and protected by the following claims.

The invention claimed is:

1. A method comprising:
modifying an antibody by reacting an antibody with a native EndoS or a mutant EndoS to form a modified antibody with a trimmed oligosaccharide;
glycosylating the modified antibody with an oligosaccharide using a mutant EndoS; and
attaching a first bioorthogonal reaction handle to the oligosaccharide, wherein the bioorthogonal reaction handle attached to the oligosaccharide is decasaccharide azide oxazoline having the following structure:

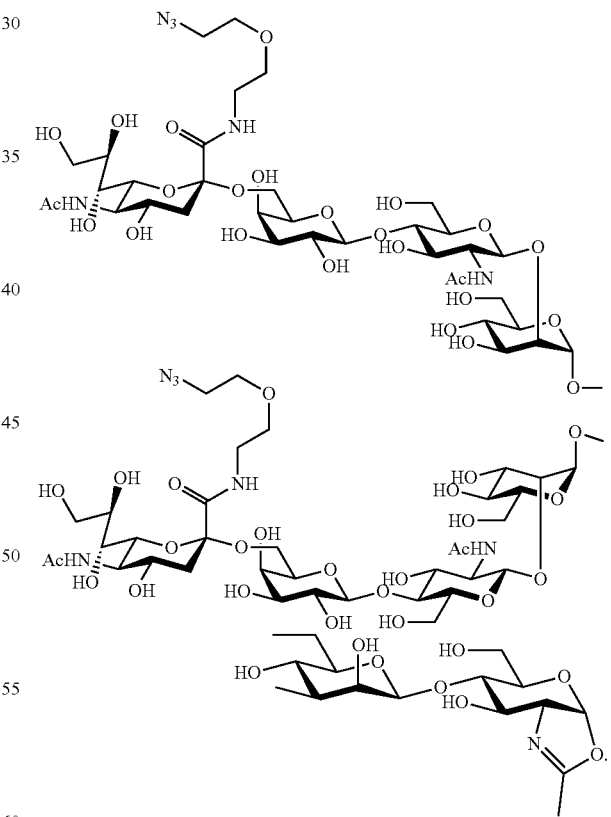

2. The method of claim 1, further comprising attaching a payload molecule to the oligosaccharide, where the payload molecule has a second bioorthogonal reaction handle, where attaching the payload molecule comprises:
attaching the first bioorthogonal reaction handle to the second bioorthogonal reaction handle.

3. The method of claim 2, wherein the payload molecule is at least one compound selected from the group consisting of: any small molecule, DNA, RNA, amino acid, peptide, polypeptide, antibody, aptamer, ribozyme, guide sequence for a ribozyme that inhibits translation or transcription of an essential tumor proteins or gene, hormone, immunomodulator, antipyretic, anxiolytic, antipsychotic, analgesic, antispasmodic, anti-inflammatory, anti-histamine, anti-infective, radiolabel, fluorophore, imaging agent, and chemotherapeutic.

4. The method of claim 2, further comprising attaching a second linker between the payload molecule and the second bioorthogonal reaction handle.

5. The method of claim 1, further comprising attaching a first linker between the first bioorthogonal reaction handle and the oligosaccharide.

6. The method of claim 1, wherein the antibody is Herceptin.

7. The method of claim 2, wherein the second bioorthogonal reaction handle attached to the payload molecule selectively reacts and attaches to the first reaction attached to the oligosaccharide on the modified antibody.

8. The method of claim 5, wherein the first linker is selected from the group consisting of amides, hydrazones, disulfides, thioethers and peptides.

9. The method of claim 4, wherein the second linker is selected from the group consisting of amides, hydrazones, disulfides, thioethers and peptides.

10. The method of claim 4, wherein the second bioorthogonal reaction handle is selected from the group consisting of strained alkynes, cyclopropenes, nitrile oxides, nitrile imines, strained alkenes and nonbornenes.

11. The method of claim 1, wherein the first bioorthogonal reaction handle is attached to the oligosaccharide via an amidation reaction.

* * * * *